US009315785B2

(12) United States Patent
Anzai et al.

(10) Patent No.: US 9,315,785 B2

(45) **Date of Patent: *Apr. 19, 2016**

(54) PYRIPYROPENE A BIOSYNTHETIC GENE

(71) Applicant: Meiji Seika Pharma Co., Ltd., Tokyo-to (JP)

(72) Inventors: Hiroyuki Anzai, Ibaraki-Ken (JP); Kentaro Yamamoto, Kanagawa-ken (JP); Mariko Tsuchida, Tokyo-To (JP); Kazuhiko Oyama, Tokyo-To (JP); Masaaki Mitomi, Kanagawa-Ken (JP)

(73) Assignee: MEIJI SEIKA PHARMA CO., LTD., Tokyo-to (JP)

( * ) Notice: Subject to any disclaimer, the term of this patent is extended or adjusted under 35 U.S.C. 154(b) by 117 days.

This patent is subject to a terminal disclaimer.

(21) Appl. No.: 14/022,778

(22) Filed: Sep. 10, 2013

(65) Prior Publication Data

US 2014/0142289 A1 May 22, 2014

Related U.S. Application Data

(63) Continuation of application No. 13/055,532, filed as application No. PCT/JP2009/063293 on Jul. 24, 2009, now Pat. No. 8,557,550.

(30) Foreign Application Priority Data

Jul. 24, 2008 (JP) ................................ 2008-190862
Oct. 20, 2008 (JP) ................................ 2008-270294
Jan. 30, 2009 (JP) ................................ 2009-020591

(51) Int. Cl.

| | |
|---|---|
| ***C12N 9/00*** | (2006.01) |
| ***C12N 9/10*** | (2006.01) |
| ***C12N 15/52*** | (2006.01) |
| ***C12P 17/18*** | (2006.01) |

(52) U.S. Cl.

CPC ................ *C12N 9/1029* (2013.01); *C12N 9/00* (2013.01); *C12N 9/1085* (2013.01); *C12N 15/52* (2013.01); *C12P 17/181* (2013.01); *Y02P 20/52* (2015.11)

(58) Field of Classification Search

CPC ......... C12N 9/00; C12N 9/1085; C12N 15/52
USPC ........................................................ 435/119
See application file for complete search history.

(56) References Cited

U.S. PATENT DOCUMENTS

| | | | |
|---|---|---|---|
| 5,807,721 A | 9/1998 | Omura et al. | |
| 8,557,550 B2 * | 10/2013 | Anzai et al. | 435/119 |
| 2006/0135664 A1 | 6/2006 | Glassel et al. | |
| 2006/0281780 A1 | 12/2006 | Goto et al. | |
| 2009/0182014 A1 | 7/2009 | Kim et al. | |
| 2010/0160640 A1 | 6/2010 | Goto et al. | |

FOREIGN PATENT DOCUMENTS

| | | |
|---|---|---|
| EP | 2 107 060 | 10/2009 |
| JP | 4-360895 | 12/1992 |
| JP | 6-184158 | 7/1994 |
| JP | 8-239385 | 9/1996 |
| JP | 8-259569 | 10/1996 |
| JP | 8-269062 | 10/1996 |
| JP | 8-269063 | 10/1996 |
| JP | 8-269064 | 10/1996 |
| JP | 8-269065 | 10/1996 |
| JP | 8-269066 | 10/1996 |
| JP | 8-291164 | 11/1996 |
| WO | 94/09147 | 4/1994 |
| WO | 2004/060065 | 7/2004 |
| WO | 2006/129714 | 12/2006 |
| WO | 2008/066153 | 6/2008 |
| WO | 2009/022702 | 2/2009 |

OTHER PUBLICATIONS

Office Action issued Feb. 19, 2014 in corresponding Russian Application No. 2011106496/10(009239), with English translation.

Murray et al., "Biochemistry of the Human", Moscow Mir, 1993, vol. 1, pp. 34.

International Search Report issued Oct. 20, 2009 in International (PCT) Application No. PCT/JP2009/063293.

N. D. Fedorova et al., "Genomic Islands in the Pathogenic Filamentous Fungus Aspergillus fumigatus", PLoS Genetics, vol. 4, No. 4, pp. 1-13, Apr. 11, 2008.

W. C. Nierman et al., "Genomic Sequence of the Pathogenic and Allergenic Filamentous Fungus Aspergillus fumigatus", Nature, vol. 438, No. 7071, pp. 1151-1156, Dec. 2005.

H. Tomoda et al., "Biosynthesis of Pyripyropene A", J. Org. Chem., vol. 61, No. 3, pp. 882-886, 1996.

T. Sunazuka et al., "Total Synthesis of α-Pyrone Meroterpenoids, Novel Bioactive Microbial Metabolites", Chem. Rev., vol. 105, No. 12, pp. 4559-4580, 2005.

G. Tsujiuchi et al., "Pyripyropene-rui Seisanno o Yusuru Shinki Biseibutsu", Hatsumei Kyokai Kokai Giho Kogi Bango, 2008-500997 Go, Feb. 13, 2008.

(Continued)

*Primary Examiner* — Tekchand Saidha

(74) *Attorney, Agent, or Firm* — Wenderoth, Lind & Ponack, L.L.P.

(57) ABSTRACT

An isolated novel polynucleotide comprising a nucleotide sequence encoding at least one polypeptide involved in biosynthesis of pyripyropene A, a recombinant vector comprising the polynucleotide and a transformant comprising the polynucleotide are disclosed. By the present invention, a pyripyropene A biosynthetic gene useful for production of a novel pyripyropene analog, improvement of productivity of a pyripyropene A-producing bacterium, production of an insecticidal agent for microorganisms, creation of a plant resistant to insect pests or the like are provided.

8 Claims, 7 Drawing Sheets

(56) References Cited

OTHER PUBLICATIONS

G. Tsujiuchi et al., "Novel Microorganism having Ability to Produce Pyripyropenes", Application Form for Journal of Technical Disclosure, Feb. 13, 2008 (English translation).
S. Omura et al., "Pyripyropenes, Highly Potent Inhibitors of Acyl-CoA: Cholesterol Acyltransferase Produced by Aspergillus fumigatus", The Journal of Antibiotics, vol. 46, No. 7, pp. 1168-1169, Jul. 1993.
T. Sunazuka et al., "Synthetic Study of α-Pyrone Meroterpenoids, Pyripyropens", Journal of Synthetic Organic Chemistry, Japan, vol. 56, No. 6, pp. 478-488, 1998.
R. Obata et al., "Chemical Modification and Structure-Activity Relationships of Pyripyropenes 3. Synthetic Conversion of Pyridine-Pyrone Moiety", The Journal of Antibiotics, vol. 50, No. 3, pp. 229-236, Mar. 1997.
H. J. Wang et al., "Aflavinines and Other Antiisectan Metabolites from the Ascostromata of Eupenicillium crustaceum and Related Species", Applied and Environmental Microbiology, vol. 61, No. 12, pp. 4429-4435, Dec. 1995.
A. B. Smith et al., "Biomimetic Total Synthesis of the ACAT Inhibitor(+)-Pyripyropene E", Tetrahedron Letters, vol. 37, No. 36, pp. 6461-6464, 1996.
H. Tomoda et al., "Pyripyropenes, Novel ACAT Inhibitors Produced by Aspergillus fumigates IV. Structure Elucidation of Pyripyropenes M to R", The Journal of Antibiotics, vol. 49, No. 3, pp. 292-298, Mar. 1996.
Supplementary European Search Report issued Nov. 29, 2011 in corresponding European Application No. 09 80 0469.
Hu, Jie, et al., "Characterization of two cytochrome P450 monooxygenase genes of the pyripyropene biosynthetic gene cluster from Penicillium coprobium", The Journal of Antibiotics, vol. 64, No. 3, Jan. 12, 2011, pp. 221-227.
Itoh, Takayuki, et al., "Reconstitution of a fungal meroterpenoid biosynthesis reveals the involvement of a novel family of terpene cyclases", Nature Chemistry, vol. 2, No. 10, Aug. 1, 2010, pp. 858-864.
Cox, Russel J., "Polyketides, proteins and genes in fungi: programmed nano-machines begin to reveal their secrets", Organic and Biomolecular Chemistry, vol. 5, No. 13, Jan. 1, 2007, pp. 2010-2026.
Varga, János, et al., "Diversity of polyketide synthase gene sequences in *Aspergillus* species", Research in Microbiology, vol. 154, No. 8, Oct. 1, 2003, pp. 593-600.
Office Action issued Nov. 15, 2012 in European Application No. 09 800 469.0.
Database UniProt [Online], Jan. 23, 2007, "Subname: Full=Putative uncharacterized protein"; Database accession No. A1DC22.

* cited by examiner

PYRIPYROPENE A BIOSYNTHETIC GENE

CROSS-REFERENCE TO RELATED APPLICATION

This patent application claims priority to Japanese Patent Application No. 190862/2008 that was filed on Jul. 24, 2008, Japanese Patent Application No. 270294/2008 that was filed on Oct. 20, 2008 and Japanese Patent Application No. 20591/2009 that was filed on Jan. 30, 2009, and the entire disclosed contents of all are hereby incorporated as part of the disclosure of the present application by reference.

BACKGROUND OF THE INVENTION

1. Field of Invention

The present invention relates to a pyripyropene A biosynthetic gene.

2. Background Art

As disclosed in Japanese Patent Laid-Open Publication No. 360895/1992 (Patent Document 1) and Journal of Antibiotics (1993), 46(7), 1168-9 (Non-patent Document 1), pyripyropene A has an inhibitory activity against ACAT (acyl CoA cholesterol acyltransferase). Application thereof to treatment of diseases caused by cholesterol accumulation or the like is expected.

Additionally, in Journal of Synthetic Organic Chemistry, Japan (1998), Vol. 56, No. 6, 478-488 (Non-patent Document 2), WO94/09147 (Patent Document 2), Japanese Patent Laid-Open Publication No. 184158/1994 (Patent Document 3), Japanese Patent Laid-Open Publication No. 239385/1996 (Patent Document 4), Japanese Patent Laid-Open Publication No. 259569/1996 (Patent Document 5), Japanese Patent Laid-Open Publication No. 269062/1996 (Patent Document 6), Japanese Patent Laid-Open Publication No. 269063/1996 (Patent Document 7), Japanese Patent Laid-Open Publication No. 269064/1996 (Patent Document 8), Japanese Patent Laid-Open Publication No. 269065/1996 (Patent Document 9), Japanese Patent Laid-Open Publication No. 269066/1996 (Patent Document 10), Japanese Patent Laid-Open Publication No. 291164/1996 (Patent Document 11) and Journal of Antibiotics (1997), 50(3), 229-36 (Non-patent Document 3), pyripyropene analogs and derivatives, as well as ACAT inhibitory activities thereof have been disclosed.

Further, Applied and Environmental Microbiology (1995), 61(12), 4429-35 (Non-patent Document 4) has disclosed that pyripyropene A has an insecticidal activity against *Helicoverpa armigera* larva. Still further, WO2004/060065 (Patent Document 12) has disclosed that pyripyropene A has insecticidal activities against Diamondback moth larva and *Tenebrio molitor.*

In addition, WO2006/129714 (Patent Document 13) and WO2008/066153 (Patent Document 14) have disclosed that pyripyropene analogs have insecticidal activities against aphids.

Furthermore, as a pyripyropene A-producing bacterium, *Aspergillus fumigatus* FO-1289 strain is disclosed in Japanese Patent Laid-Open Publication No. 360895/1992 (Patent Document 1); *Eupenicillium reticulosporum* NRRL-3446 strain is in Applied and Environmental Microbiology (1995), 61(12), 4429-35 (Non-patent Document 4); and *Penicillium griseofulvum* F1959 strain is in WO2004/060065 (Patent Document 12); and *Penicillium coprobium* PF1169 strain is in Journal of Technical Disclosure 500997/2008 (Patent Document 15).

Also, as a biosynthetic route of pyripyropene A, Journal of Organic Chemistry (1996), 61, 882-886 (Non-patent Document 5) and Chemical Review (2005), 105, 4559-4580 (Non-patent Document 6) have disclosed a putative biosynthetic route in *Aspergillus fumigatus* FO-1289 strain. These documents have disclosed that, in *Aspergillus fumigatus* FO-1289 strain, partial structures individually synthesized by polyketide synthase and prenyltransferase are linked to synthesize pyripyropene A by a cyclase.

PRIOR ART REFERENCES

Patent Documents

[Patent Document 1] Japanese Patent Laid-Open Publication No. 360895/1992

[Patent Document 2] WO94/09147

[Patent Document 3] Japanese Patent Laid-Open Publication No. 184158/1994

[Patent Document 4] Japanese Patent Laid-Open Publication No. 239385/1996

[Patent Document 5] Japanese Patent Laid-Open Publication No. 259569/1996

[Patent Document 6] Japanese Patent Laid-Open Publication No. 269062/1996

[Patent Document 7] Japanese Patent Laid-Open Publication No. 269063/1996

[Patent Document 8] Japanese Patent Laid-Open Publication No. 269064/1996

[Patent Document 9] Japanese Patent Laid-Open Publication No. 269065/1996

[Patent Document 10] Japanese Patent Laid-Open Publication No. 269066/1996

[Patent Document 11] Japanese Patent Laid-Open Publication No. 291164/1996

[Patent Document 12] WO2004/060065

[Patent Document 13] WO2006/129714

[Patent Document 14] WO2008/066153

[Patent Document 15] Journal of Technical Disclosure 500997/2008

Non-Patent Documents

[Non-patent Document 1] Journal of Antibiotics (1993), 46(7), 1168-9

[Non-patent Document 2] Journal of Synthetic Organic Chemistry, Japan (1998), Vol. 56, No. 6, 478-488

[Non-patent Document 3] Journal of Antibiotics (1997), 50(3), 229-36

[Non-patent Document 4] Applied and Environmental Microbiology (1995), 61(12), 4429-35

[Non-patent Document 5] Journal of Organic Chemistry (1996), 61, 882-886

[Non-patent Document 6] Chemical Review (2005), 105, 4559-4580

SUMMARY OF THE INVENTION

The present inventors have now found out a nucleotide sequence encoding at least one polypeptide involved in biosynthesis of pyripyropene A. The present invention has been made based on such finding.

Accordingly, an object of the present invention is to provide an isolated novel polynucleotide having a nucleotide sequence encoding at least one polypeptide involved in biosynthesis of pyripyropene A, a recombinant vector comprising the polynucleotide, and a transformant comprising the polynucleotide.

Further, according to one embodiment of the present invention, an isolated polynucleotide which is (a) a polynucleotide having a nucleotide sequence of SEQ ID NO:266, (b) a polynucleotide having a nucleotide sequence which is capable of hybridizing with the nucleotide sequence of SEQ ID NO:266 under stringent conditions, or (c) a polynucleotide having a polynucleotide sequence encoding at least one amino acid sequence selected from SEQ ID NOs:267 to 274 or a substantially equivalent amino acid sequence thereto; is provided.

Also, according to another embodiment of the present invention, an isolated polynucleotide which has at least one nucleotide sequence selected from the nucleotide sequence in any of (1) or (2) below:

(1) a nucleotide sequence in any of (a) to (h) below:

(a) a nucleotide sequence from 3342 to 5158 of a nucleotide sequence shown in SEQ ID NO:266, (b) a nucleotide sequence from 5382 to 12777 of a nucleotide sequence shown in SEQ ID NO:266, (c) a nucleotide sequence from 13266 to 15144 of a nucleotide sequence shown in SEQ ID NO:266, (d) a nucleotide sequence from 16220 to 18018 of a nucleotide sequence shown in SEQ ID NO:266, (e) a nucleotide sequence from 18506 to 19296 of a nucleotide sequence shown in SEQ ID NO:266, (f) a nucleotide sequence from 19779 to 21389 of a nucleotide sequence shown in SEQ ID NO:266, (g) a nucleotide sequence from 21793 to 22877 of a nucleotide sequence shown in SEQ ID NO:266, (h) a nucleotide sequence from 23205 to 24773 of a nucleotide sequence shown in SEQ ID NO:266;

(2) a nucleotide sequence which is capable of hybridizing with a nucleotide sequence in (1) under stringent conditions; is provided.

Further, according to another embodiment of the present invention, a polynucleotide encoding at least one polypeptide involved in biosynthesis of pyripyropene A is provided.

In addition, according to another embodiment of the present invention, a polynucleotide encoding a polypeptide having any one or more activities of polyketide synthase activity, prenyltransferase activity, hydroxylase activity, acetyltransferase activity or adenylate synthetase activity is provided.

Still further, according to another embodiment of the present invention, a polynucleotide which is derived from *Penicillium coprobium* PF1169 strain is provided.

Additionally, according to another embodiment of the present invention, a recombinant vector comprising the above-mentioned polynucleotide is provided.

Still further, according to another embodiment of the present invention, a transformant comprising the above-mentioned polynucleotide is provided.

In addition, according to one embodiment of the present invention, a method for producing a pyripyropene A precursor, characterized by culturing a transformant in which a polynucleotide having nucleotide sequence of the above-mentioned (c) or (d) is incorporated simultaneously or separately, and isolating the pyripyropene A precursor from pyripyropene E represented by the following formula is provided:

[Chemical formula 1]

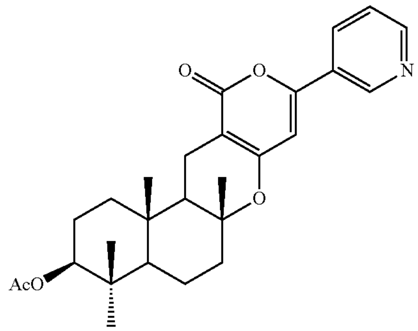

Pyripyropene E

Still further, a production method wherein the above-mentioned pyripyropene A precursor is one represented by the following formula (I) is provided:

[Chemical formula 2]

formula (I)

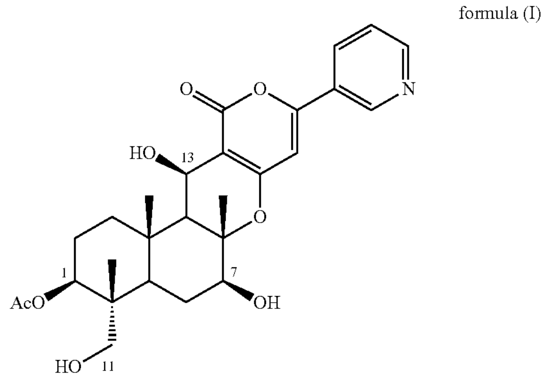

Also, a method for producing a pyripyropene A precursor characterized by culturing the above-mentioned transformant and isolating the pyripyropene A precursor from pyripyropene O represented by the following formula is provided:

[Chemical formula 3]

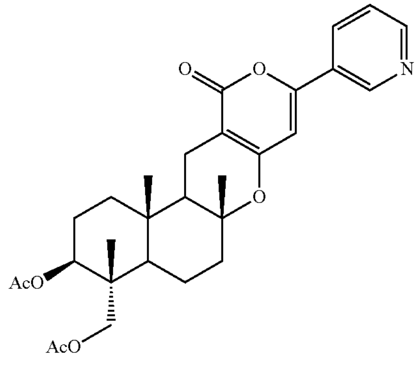

Pyripyropene O

Still further, a production method wherein the above-mentioned pyripyropene A precursor is a compound represented by the following formula (II) is provided:

[Chemical formula 4]

formula (II)

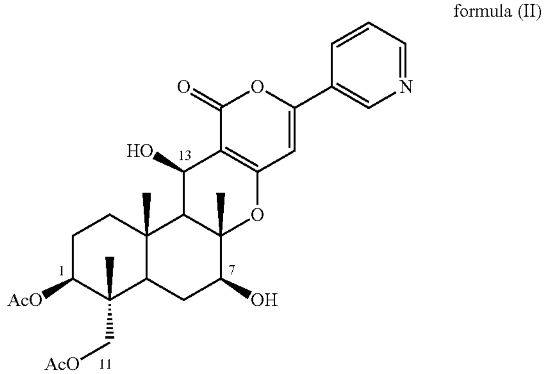

According to one embodiment of the present invention, production of a novel pyripyropene analog, improvement of productivity of a pyripyropene A-producing bacterium, production of a novel insecticidal agent for microorganisms, creation of a novel plant resistant to insect pests or the like are provided.

BRIEF DESCRIPTION OF DRAWINGS

Similarly to FIG. 1.

Similarly to FIG. 1.

DETAILED DESCRIPTION OF THE INVENTION

Deposition of Microorganisms

Figure 1:
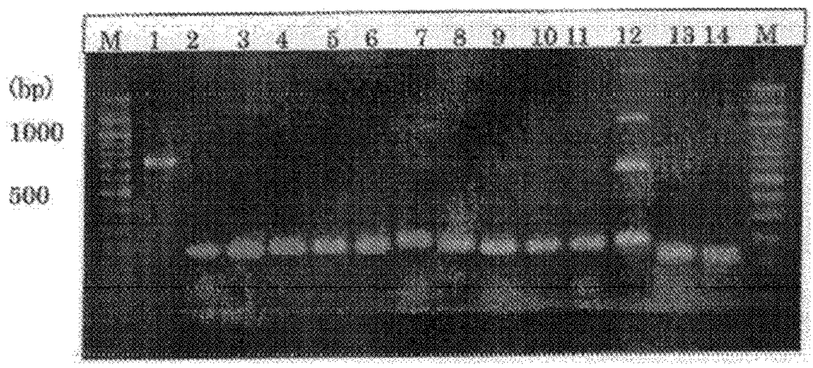
FIG. 1 shows an electrophoresis pattern of PCR products by agarose gel. For the electrophoresis, the PCR products amplified using the following primers were used: M: molecular weight marker (100 bp ladder), lane 1: primers of SEQ ID NOs:1 and 2, lane 2: primers of SEQ ID NOs:239 and 240, lane 3: primers of SEQ ID NOs:237 and 238, lane 4: primers of SEQ ID NOs:241 and 242, lane 5: primers of SEQ ID NOs:247 and 248, lane 6: primers of SEQ ID NOs:251 and 252, lane 7: primers of SEQ ID NOs:245 and 246, lane 8: primers of SEQ ID NOs:243 and 244, lane 9: primers of SEQ ID NOs:249 and 250, lane 10: primers of SEQ ID NOs:235 and 236, lane 11: primers of SEQ ID NOs:233 and 234, lane 12: primers of SEQ ID NOs:227 and 228, lane 13: primers of SEQ ID NOs:229 and 230, lane 14: primers of SEQ ID NOs:231 and 232.

*Escherichia coli* (*Escherichia coli* EPI300™-T1®) transformed with plasmid pCC1-PP1 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11133 (converted from domestic deposition under accession No. FERM P-21704) (identification reference by the depositors: *Escherichia coli* EPI300™-T1®/pCC1-PP1) as of Oct. 9, 2008 (original deposition date).

*Aspergillus oryzae* transformed with plasmid pPP2 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11137 (identification reference by the depositors: *Aspergillus oryzae* PP2-1) as of Jun. 23, 2009.

*Aspergillus oryzae* transformed with plasmid pPP3 has been deposited with International Patent Organism Depositary, National Institute of Advanced Industrial Science and Technology (Address: AIST Tsukuba Central 6, 1-1-1 Higashi, Tsukuba, Ibaraki, Japan, 305-8566), under accession No. FERM BP-11141 (identification reference by the depositors: *Aspergillus oryzae* PP3-2) as of Jul. 3, 2009.

Isolated Polynucleotide

The present invention is an isolated polynucleotide. The isolated polynucleotide according to the present invention is (a) a polynucleotide having the nucleotide sequence of SEQ ID NO:266; (b) a polynucleotide having a nucleotide sequence which is capable of hybridizing with the nucleotide sequence of SEQ ID NO:266 under stringent conditions, or (c) a polynucleotide having a polynucleotide sequence encoding at least one amino acid sequence selected from SEQ ID NOs:267 to 274 or a substantially equivalent amino acid sequence thereto. The above-mentioned isolated polynucleotide preferably has a nucleotide sequence encoding at least one polypeptide which has an enzyme activity involved in biosynthesis of pyripyropene A.

In the present invention, "a substantially equivalent amino acid sequence" means an amino acid sequence which does not affect an activity of a polypeptide despite the fact that one or more amino acids are altered by substitution, deletion, addition or insertion. The number of the altered amino acid residues is preferably 1 to 40 residues, more preferably 1 to several residues, still more preferably 1 to 8 residues, most preferably 1 to 4 residues.

Further, an example of the alteration which does not affect the activity includes conservative substitution. The term, "conservative substitution" means substitution of one or more amino acid residues with other chemically similar amino acid residues such that the activity of a polypeptide is not substantially altered. Examples thereof include cases where a certain hydrophobic amino acid residue is substituted with another hydrophobic amino acid residue and cases where a certain polar amino acid residue is substituted with another polar amino acid residue having the same charges. Functionally similar amino acids capable of such a substitution are known in the art for each amino acid. Concretely, examples of nonpolar (hydrophobic) amino acids include alanine, valine, isoleucine, leucine, proline, tryptophan, phenylalanine, methionine and the like. Examples of polar (neutral) amino acids include glycine, serine, threonine, tyrosine, glutamine, asparagine, cysteine and the like. Examples of positively charged (basic) amino acids include arginine, histidine, lysine and the like. Examples of negatively charged (acidic) amino acids include aspartic acid, glutamic acid and the like.

Also, the isolated polynucleotide of the present invention may be a polynucleotide having at least one nucleotide sequence selected from the nucleotide sequence in any of (1) or (2) below:

(1) a polynucleotide sequence in any of (a) to (h) below:

(a) a nucleotide sequence from 3342 to 5158 of a nucleotide sequence shown in SEQ ID NO:266, (b) a nucleotide sequence from 5382 to 12777 of a nucleotide sequence shown in SEQ ID NO:266, (c) a nucleotide sequence from 13266 to 15144 of a nucleotide sequence shown in SEQ ID NO:266, (d) a nucleotide sequence from 16220 to 18018 of a nucleotide sequence shown in SEQ ID NO:266, (e) a nucleotide sequence from 18506 to 19296 of a nucleotide sequence shown in SEQ ID NO:266, (f) a nucleotide sequence from 19779 to 21389 of a nucleotide sequence shown in SEQ ID NO:266, (g) a nucleotide sequence from 21793 to 22877 of a nucleotide sequence shown in SEQ ID NO:266, (h) a nucleotide sequence from 23205 to 24773 of a nucleotide sequence shown in SEQ ID NO:266;

(2) a nucleotide sequence which is capable of hybridizing with a nucleotide sequence in (1) under stringent conditions.

A polynucleotide having at least one nucleotide sequence selected from the nucleotide sequence in any of the above-mentioned (1) or (2) preferably encodes at least one polypeptide having an enzyme activity involved in biosynthesis of pyripyropene A.

The term, "stringent conditions" in the present invention means conditions where a washing operation of membranes after hybridization is carried out at high temperatures in a solution with low salt concentrations, for example, conditions of washing in a solution with 2×SSC concentration (1×SSC: 15 mM trisodium citrate, 150 mM sodium chloride) and 0.5% SDS at 60° C. for 20 minutes.

The polynucleotide having at least one nucleotide sequence selected from the nucleotide sequence in any of the above-mentioned (1) or (2) according to the present invention is one encoding a polypeptide having any one or more activities of polyketide synthase activity, prenyltransferase activity, hydroxylase activity, acetyltransferase activity or adenylate synthetase activity; and, in particular, one encoding a polypeptide having the hydroxylase activity.

Further, according to one embodiment of the present invention, the above-mentioned polynucleotide is one encoding a polypeptide having an activity to hydroxylate the 7-position and/or 13-position of the above-mentioned pyripyropene E or O, or one encoding a polypeptide having an activity to hydroxylate the 11-position of the above-mentioned pyripyropene E.

Obtainment of Isolated Polynucleotide

The method for obtaining the isolated polynucleotide of the present invention is not particularly restricted. For instance, the polynucleotide can be isolated from *Penicillium coprobium* PF1169 strain or filamentous bacterium by the following method.

Based on a homology sequence obtained by the method of Example 9 below or the like, primers capable of specifically amplifying a polyketide synthase gene are synthesized. PCR is carried out for a fosmid genomic library of *Penicillium coprobium* PF1169 strain which is separately prepared, followed by colony hybridization. A recombinant vector is thereby obtained and the base sequence of an inserted DNA thereof is determined.

Also, based on the homology sequence obtained by the method of Example 9 below or the like, primers capable of specifically amplifying a prenyltransferase gene are synthesized. Further, the base sequence of an inserted DNA is determined in the same manner as above.

Further, based on the homology sequence obtained by the method of Example 9 below or the like, primers capable of specifically amplifying any one or both of a polyketide synthase gene and prenyltransferase gene are synthesized. Further, the base sequence of an inserted DNA is determined in the same manner as above.

In addition, based on the homology sequence of at least one nucleotide sequence selected from SEQ ID NO:266 and the nucleotide sequence in any of the above-mentioned (1) or (2) according to the present invention, primers capable of specifically amplifying any one or more of a polyketide synthase gene, prenyltransferase gene, hydroxylase gene, acetyltransferase gene or adenylate synthetase gene, preferably the hydroxylase gene are synthesized. Further, the base sequence of an inserted DNA is determined in the same manner as above.

Still further, based on an amino acid sequence conserved among various filamentous bacterium polyketide synthases, degenerate primers for amplification were synthesized and the base sequence of an inserted DNA is determined.

Transformant

In general, examples of a method for improving productivity of a secondary metabolism product by gene recombination include improving expression of a gene encoding a protein catalyzing a biosynthetic reaction which is a rate limiting reaction, improving expression of or disrupting a gene regulating expression of a biosynthetic gene, blocking an unnecessary secondary metabolism system, and the like. Therefore, specifying the biosynthetic gene makes it possible to improve the productivity of the secondary metabolism product by ligating the gene to an appropriate vector and introducing the vector into a production bacterium.

Meanwhile, in order to create a novel active substance by gene recombination, domain alteration of polyketide synthase [Ikada and Ohmura, "PROTEIN, NUCLEIC ACID AND ENZYME" Vol. 43, p. 1265-1277, 1998], [Carreras, C. W. and Santi, D. V., "Current Opinion in Biotechnology", (UK), 1998, Vol. 9, p. 403-411], [Hutchinson, C. R., "Current Opinion in Microbiology", (UK), 1998, Vol. 1, p. 319-329], [Katz, L. and McDaniel, R., "Medicinal Research Reviews", (USA), 1999, Vol. 19, p. 543-558]; disruption of a biosynthetic gene; introduction of a modification enzyme gene from other organisms [Hutchinson, C. R., "Bio/Technology", (USA), 1994, Vol. 12, p. 375-380]; and the like are carried out. Thus, specifying the biosynthetic gene makes it possible to create the novel active substance by ligating the gene to an appropriate vector and introducing the vector into a bacterium producing a secondary metabolism product.

Therefore, pyripyropene A can be produced or productivity thereof can be improved by ligating the isolated polynucleotide according to the present invention to the appropriate vector, introducing the vector into a host, expressing it, enhancing expression thereof, or carrying out gene disruption of part of the isolated polynucleotide using homologous recombination and impairing functions thereof.

Gene disruption using homologous recombination can be carried out in accordance with a conventional method. Preparation of a vector used for the gene disruption and introduction of the vector into a host are apparent for those skilled in the art.

The recombinant vector according to the present invention preferably comprises any one or more of polynucleotides having the nucleotide sequence in SEQ ID NO:266 and the above-mentioned (1); a polynucleotide having a nucleotide sequence which is capable of hybridizing with the nucleotide sequence in SEQ ID NO:266 and the above-mentioned (1) under stringent conditions, or a polynucleotide having a polynucleotide sequence encoding at least one amino acid sequence selected from SEQ ID NOs:267 to 274 or a substantially equivalent amino acid sequence thereto. More preferably, the recombinant vector according to the present invention is one wherein the above-mentioned polypeptide comprises a polynucleotide hydroxylating the 7-position and/or 13-position of the pyripyropene E or O, and the above-mentioned polypeptide comprises a polynucleotide hydroxylating the 11-position of the pyripyropene E.

A recombinant vector for gene introduction can be prepared by modifying the polynucleotide provided by the present invention into an appropriate form depending on an object and ligating it to a vector in accordance with a conventional method, for example, gene recombination techniques described in [Sambrook, J. et al., "Molecular cloning: a laboratory manual", (USA), 2nd Edition, Cold Spring Harbor Laboratory, 1989].

The recombinant vector used in the present invention can be appropriately selected from virus, plasmid, fosmid, cosmid vectors or the like. For instance, when a host cell is *Escherichia coli*, examples thereof include λ phage-based bacteriophage and pBR and pUC-based plasmids. In the case of a *Bacillus subtilis*, examples include pUB-based plasmids. In the case of yeast, examples include YEp, YRp, YCp and YIp-based plasmids.

In addition, it is preferred that at least one plasmid among the used plasmids comprise a selection marker for selecting a transformant. As the selection marker, a gene encoding drug resistance and gene complementing auxotrophy can be used. Concrete preferred examples thereof include when a host to be used is bacterium, ampicillin resistant genes, kanamycin resistant genes, tetracycline resistant gene and the like; in the case of yeast, tryptophan biosynthetic gene (TRP1), uracil biosynthetic gene (URA3), leucine biosynthetic gene (LEU2) and the like; in the case of a fungus, hygromycin resistant genes, bialaphos resistant genes, bleomycin resistant genes, aureobasidin resistant genes and the like; and in the case of a plant, kanamycin resistant genes, bialaphos resistant genes and the like.

Further, DNA molecules serving as an expression vector used in the present invention preferably has DNA sequences necessary to express each gene, transcription regulatory signals and translation regulatory signals such as promoters, transcription initiation signals, ribosome binding sites, translation stop signals, terminators. Preferred examples of the promoters include promoters of lactose operon, tryptophan operon and the like in *Escherichia coli*; promoters of alcohol dehydrogenase gene, acid phosphatase gene, galactose metabolizing gene, glyceraldehyde 3-phosphate dehydrogenase gene or the like in yeast; promoters of α-amylase gene, glucoamylase gene, cellobiohydrolase gene, glyceraldehyde 3-phosphate dehydrogenase gene, abp1 gene or the like in fungi; a CaMV 35S RNA promoter, a CaMV 19S RNA promoter or a nopaline synthetase gene promoter in plants.

A host in which the isolated polynucleotide according to the present invention is introduced may be appropriately selected, depending on the type of the used vector, from actinomycetes, *Escherichia coli, Bacillus subtilis*, yeast, filamentous bacteria, plant cells or the like.

A method of introducing a recombinant vector into a host may be selected, depending on a host cell under test, from conjugal transfer, transduction by phage, as well as methods of transformation such as a calcium ion method, a lithium ion method, an electroporation method, a PEG method, an *Agrobacterium* method or a particle gun method.

In cases where a plurality of genes is introduced into host cells in the present invention, the genes may be contained in a single DNA molecule or individually in different DNA molecules. Further, when a host cell is a bacterium, each gene can be designed so as to be expressed as polycistronic mRNA and made into one DNA molecule.

The transformant according to the present invention preferably comprises any one or more of polynucleotides having the nucleotide sequence in SEQ ID NO:266 and the above-mentioned (1); a polynucleotide having a nucleotide sequence which is capable of hybridizing with the nucleotide sequence in SEQ ID NO:266 and the above-mentioned (1) under stringent conditions, or a polynucleotide having a polynucleotide sequence encoding at least one amino acid sequence selected from SEQ ID NOs:267 to 274 or a substantially equivalent amino acid sequence thereto.

The transformant obtained can be cultured by a conventional method and newly characteristics obtained can be studied. As the medium, commonly used components, for example, as carbon sources, glucose, sucrose, starch syrup, dextrin, starch, glycerol, molasses, animal and vegetable oils or the like can be used. Also, as nitrogen sources, soybean flour, wheat germ, corn steep liquor, cotton seed meal, meat extract, polypeptone, malto extract, yeast extract, ammonium sulfate, sodium nitrate, urea or the like can be used. Besides, as required, addition of sodium, potassium, calcium, magnesium, cobalt, chlorine, phosphoric acid (dipotassium hydrogen phosphate or the like), sulfuric acid (magnesium sulfate or the like) or inorganic salts which can generate other ions is effective. Also, as required, various vitamins such as thiamin (thiamine hydrochloride or the like), amino acids such as glutamic acid (sodium glutamate or the like) or asparagine (DL-asparagine or the like), trace nutrients such as nucleotides, or selection agents such as antibiotics can be added. Further, organic substances or inorganic substances which help the growth of a bacterium and promote the production of pyripyropene A can be appropriately added.

The pH of the medium is, for example, about pH 5.5 to pH 8. As the method for culturing, solid culturing under aerobic conditions, shake culturing, culturing with bubbling under stirring or deep part aerobic culturing can be employed and, in particular, the deep part aerobic culturing is most appropriate. The appropriate temperature for the culturing is 15° C. to 40° C. and, in many cases, the growth takes place around 22° C. to 30° C. The production of pyripyropene A varies depending on the medium and culturing conditions, or the used host. In any method for culturing, the accumulation usually reaches a peak in 2 days to 10 days. The culturing is terminated at the time when the accumulation of pyripyropene A in the culture reaches the peak and a desired substance is isolated and purified from the culture.

To isolate pyripyropene A from the culture, it can be extracted and purified by a usual separation means using properties thereof, such as a solvent extraction method, an ion exchange resin method, an adsorption or distribution column chromatography method, a gel filtration method, dialysis, a precipitation method, a crystallization method, which may be individually used or appropriately used in combination.

Method for Producing Pyripyropene A Precursor

In order to isolate pyripyropene A, pyripyropene A can be isolated from a pyripyropene A precursor using a known method. An example of the known method includes the method of WO2009/022702. By culturing a microorganism containing a vector containing one or more of the above, the pyripyropene A precursor can be isolated from pyripyropene E. The pyripyropene A precursor may be, for example, the compound represented by the above-mentioned formula (I).

Also, by culturing a microorganism comprising a vector containing one or more, the pyripyropene A precursor can be isolated from pyripyropene O. An example may be the compound represented by the above-mentioned formula (II).

EXAMPLES

The present invention will be further illustrated in detail by the following examples, which are not intended to restrict the present invention.

Example 1

Preparation of Genomic DNA of *Penicillium coprobium* PF1169 Strain

Sterilized NB medium (500 ml) was placed in an Erlenmeyer flask (1 L). *Penicillium coprobium* PF1169 strain (Journal of Technical Disclosure No. 500997/2008 (Patent Document 15)) precultured in 1/2 CMMY agar medium at 28° C. for 4 days was added to the above-mentioned medium and subjected to liquid culture at 28° C. for 4 days. Filtration was carried out with Miracloth to obtain 5 g of bacterial cells. From these bacterial cells, 30 μg of genomic DNA was obtained in accordance with the manual attached to genomic DNA purification kit Genomic-tip 100/G (manufactured by Qiagen K.K.).

Example 2

Degenerate Primers for Amplification of Polyketide Synthase (PKS) and Amplified Fragment Thereof Based on an amino acid sequence conserved among various filamentous bacterium polyketide synthases, the following primers were designed and synthesized as degenerate primers for amplification:

```
LC1:   GAYCCIMGITTY1TYAAYATG    (SEQ ID NO: 1)

LC2c:  GTICCIGTICCRTGCATYTC     (SEQ ID NO: 2)
```

(wherein R=A/G, Y=C/T, M=A/C, I=inosine).

Using these degenerate primers, the genomic DNA prepared in Example 1 and ExTaq polymerase (manufactured by Takara Bio Inc.) were allowed to react in accordance with the attached manual. An amplified fragment of about 700 bp was detected (see FIG. 1). Further, the above-mentioned amplified fragment was analyzed to specify the sequence of its internal 500 bp (SEQ ID NO:3).

Example 3

Large-Scale Sequencing of Genomic DNA and Amino Acid Sequence Homology Search The genomic DNA of *Penicillium coprobium* PF1169 strain obtained in Example 1 was subjected to large-scale sequencing and homology search for amino acid sequences. Specifically, part of 50 μg of genomic DNA was pretreated and thereafter subjected to Roche 454FLX DNA sequencer to obtain about 250 bp, 103 thousands of fragment sequences (in total, 49 Mb of sequence).

For theses sequences, as known sequences among polyketide synthases and prenyltransferases, the following five sequences (sequences derived from polyketide synthases: *Aspergillus* (*A.*) *fumigatus* PKS 2146 a.a. and *Penicillium* (*P.*) *griseofluvum* 6-methylsalycilic acid synthase 1744 a.a.; as well as prenyltransferases: *Aspergillus* (*A.*) *fumigatus* Prenyltransferase, *Aspergillus* (*A.*) *fumigatus* Prenyltransferase (4-hydroxybezoate octaprenyltransferase) and *Penicillium* (*P.*) *marneffei* Prenyltransferase) were selected and search by homology sequence search software blastx was carried out, thereby obtaining 89, 86, 2, 1 and 3 of homology sequences, respectively (see Table 1). Further, from the homology sequences of *A. fumigatus* PKS 2146 a.a. and *P. griseofluvum* 6-methylsalycilic acid synthase 1744 a.a., 19 and 23 of contig sequences were respectively obtained (the contig sequences of *A. fumigatus* PKS 2146 a.a.: SEQ ID NOs:179 to 197; the contig sequences of *P. griseofluvum* 6-methylsalycilic acid synthase 1744 a.a.: SEQ ID NOs:198 to 220) (see Table 1).

TABLE 1

| Enzyme Name | Origin | Number of Homology Sequences | SEQ ID NO. |
|---|---|---|---|
| Polyketide Synthases | *A. fumigatus* PKS 2146 a.a. | 89 | 4-92 |
| | *P. griseofluvum* 6-methylsalycilic acid synthase 1744 a.a. | 86 | 93-178 |
| | *A. fumigatus* PKS 2146 a.a. | 19 (Contig sequences) | 179-197 |
| | *P. griseofluvum* 6-methylsalycilic acid synthase 1744 a.a. | 23 (Contig sequences) | 198-220 |
| Prenyltransferase | *A. fumigatus* Prenyltransferase | 2 | 221, 222 |
| | *A. fumigatus* Prenyltransferases (4-hydroxybezoate octaprenyltransferase) | 1 | 223 |
| | *P. marneffei* Prenyltransferase | 3 | 224-226 |

Example 4

PCR Amplification from Genomic DNA

Figure 2:
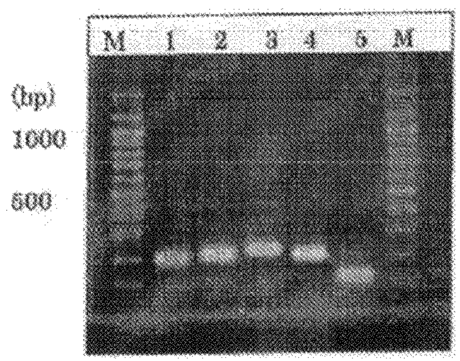
FIG. 2 shows an electrophoresis pattern of PCR products by agarose gel. For the electrophoresis, the PCR products amplified using the following primers were used: M: molecular weight marker (100 bp ladder), lane 1: primers of SEQ ID NOs:253 and 254, lane 2: primers of SEQ ID NOs:257 and 258, lane 3: primers of SEQ ID NOs:259 and 260, lane 4: primers of SEQ ID NOs:255 and 256, lane 5: primers of SEQ ID NOs:261 and 262.

From the search results of blastx obtained in Example 3, for polyketide synthases, 13 types of primer pairs shown in SEQ ID NOs:227 to 252 were synthesized. Similarly, for prenyltransferases, 5 types of primer pairs shown in SEQ ID NOs: 253 to 262 were synthesized. When PCR was carried out for the genomic DNA using these primers, amplified fragments with the expected size were seen for all of the primer pairs (see FIG. 1 and FIG. 2).

Example 5

Construction of Phage Genomic Library

A λ phage genomic library of *Penicillium coprobium* PF1169 strain was constructed using λBlueSTAR Xho I Halfsite Arms Kit (manufactured by Takara Bio Inc., Cat. No. 69242-3) in accordance with the attached manual. That is, genomic DNA was partially digested using a restriction enzyme, Sau3A1. The DNA fragment with about 20 kb (0.5 μg) was ligated to 0.5 μg of λBlueSTAR DNA attached to the kit. This ligation solution was subjected to in vitro packaging using Lambda INN Packaging kit (manufactured by Nippon Gene Co., Ltd.) based on the manual attached to the kit to obtain 1 ml of a solution. This solution with packaged phages (10 μl) was infected into 100 μl of *E. coli* ER1647 strain and cultured on a plaque-forming medium at 37° C. overnight, thereby obtaining about 500 clones of plaques. Thus, the genomic library composed of about 50000 clones of phages in which 10 to 20 kb genomic DNA of *Penicillium coprobium* PF1169 strain were introduced by infection was constructed.

Example 6

Screening from Phage Library

For 10000 clones of the phage library prepared in Example 5, the primary screening was carried out by plaque hybridization using, as a probe, the PCR product amplified by LC1-LC2c primer pair prepared above. For labeling and detection of the probe, AlkPhos Direct Labelling and Detection System with CDP-Star (manufactured by GE Healthcare, Cat. No. RPN3690) was used. The above-mentioned hybridization was carried out in accordance with the attached manual.

By the primary screening, 6 clones remained as candidates. Further, as the result of the secondary screening by plaque hybridization, 4 clones were obtained. These positive clones were infected into *E. coli* BM25.8 strain and the phages were converted to plasmids in accordance with the attached manual, thereby obtaining 4 types of plasmids containing a desired region.

Example 7

Preparation of Fosmid Genome Library

A genomic library of *Penicillium coprobium* PF1169 strain was constructed using CopyControl Fosmid Library Production Kit (manufactured by EPICENTRE, Cat. No. CCFOS110) in accordance with the manual attached thereto. That is, 0.25 μg of DNA fragment of about 40 kb genomic DNA was blunt-ended and then incorporated into fosmid vector pCCFOS (manufactured by Epicentre). This ligation solution was subjected to in vitro packaging using MaxPlax Lambda Packaging Extract attached to the kit based on the manual attached to the kit. This solution with packaged virus (10 μl) was infected into 100 μl of *E. coli* EPI300™-T1® strain and cultured on a medium containing chloramphenicol at 37° C. overnight and selected, thereby obtaining about 300 clones of plaques. Thus, about 30000 clones of the fosmids in which 40 kb of the genomic DNA of *Penicillium coprobium* PF1169 strain were introduced by infection were obtained. They were aliquoted in a 96 well plate so as to be about 50 clones per well. Thus, the genomic library composed of 96 pools, about 4800 clones was constructed.

Example 8

Fosmid Library Screening

In accordance with the manual attached to the fosmid, plasmid DNAs were individually prepared from 96 pools of the library prepared in Example 7. Using the degenerate primers for polyketide synthase amplification synthesized in Example 2, PCR was carried out for 96 pools of these plasmid DNA samples. As a result, DNA fragments of about 700 bp were amplified from 9 pools. Further, a petri dish containing colonies of about 300 clones or more was prepared from the positive pools and re-screening was carried out by colony hybridization. As a result, using by LC1-LC2c primer pair, 9 types of fosmids were obtained from about 4800 clones.

Example 9

Large-Scale Sequencing of Genomic DNA and Amino Acid Sequence Homology Search Genomic DNA of *Penicillium coprobium* PF1169 strain obtained in Example 1 was subjected to large-scale sequencing and homology search for amino acid sequences. Specifically, part of 50 μg of genomic DNA was pretreated and then subjected to Roche 454FLX DNA sequencer to obtain 1405 fragment sequences with an average contig length of 19.621 kb (sequence of a total base length of 27.568160 Mb).

For these sequences, as known sequences among polyketide synthases and prenyltransferases, the following five sequences (sequences derived from polyketide synthases: *Penicillium* (*P.*) *griseofluvum* 6-methylsalycilic acid synthase 1744 a.a. (P22367) and *Aspergillus* (*A.*) *fumigatus* PKS 2146 a.a. (Q4WZA8); as well as prenyltransferases: *Penicillium* (*P.*) *marneffei* Prenyltransferase (Q0MRO8), *Aspergillus* (*A.*) *fumigatus* Prenyltransferase (Q4WBI5) and *Aspergillus* (*A.*) *fumigatus* Prenyltransferase (4-hydroxybezoate octaprenyltransferase) (Q4WLD0)) were selected and search by homology sequence search software blastx was carried out, thereby obtaining 22 (P22367), 21 (Q4WZA8), 2 (Q0MRO8), 3 (Q4WBI5) and 3 (Q4WLD0) of the homologous sequences, respectively.

Example 10

Fosmid Library Screening and Sequence Analysis of Cluster Genes

Figure 3:
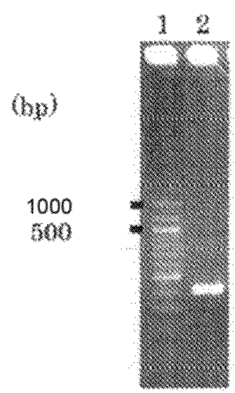
FIG. 3 shows an electrophoresis pattern of PCR products by agarose gel. For the electrophoresis, the PCR products amplified using the following primers were used: lane 1: molecular weight marker (100 bp ladder), lane 2: primers of SEQ ID NOs:264 and 265 (400 bp amplified fragment).

In accordance with the manual attached to a fosmid kit (manufactured by EPICENTRE, CopyControl Fosmid Library Production Kit), plasmid DNAs were individually prepared from 96 pools of the library prepared in Example 7. Based on base sequences determined by Roche 454FLX DNA sequencer, homology search for amino acid sequences was carried out to search regions adjacent to polyketide synthase and prenyltransferase. Based on the base sequence of prenyltransferase of the obtained region, a primer pair (No. 27) capable of amplifying 400 bp DNA fragment was synthesized. Using the primers, PCR was carried out for these 48 pools of plasmid DNA samples. As a result, expected DNA fragments of about 400 bp (SEQ ID NO:263) were amplified from 11 pools (see FIG. 3). Further, a petri dish containing colonies of about 300 clones or more was prepared from 6 pools of the positive pools and re-screening was carried out by colony hybridization. As a result, by using 27F+27R primer pair (27F primer: SEQ ID NO:264, 27R primer: SEQ ID NO:265), 4 types of fosmids were obtained from about 4800 clones. One of them was named pCC1-PP1 and the entire sequence of the inserted fragment was determined (SEQ ID NO:266).

The obtained pCC1-PP1 was transformed into *Escherichia coli* EPI300™-T1® strain (included in the fosmid kit), thereby obtaining *Escherichia coli* EPI300™-T1® strain/pCC1-PP1.

When a homology search was carried out between the above-mentioned sequence of SEQ ID NO:266 and each of Adenylate-forming enzyme; LovB-like polyketide synthase; Cytochrome P450 monooxygenase, Integral membrane protein, FAD-dependent monooxygenase, which are hydroxylases; UbiA-like prenyltransferase; Acetyltransferase, Toxin biosynthesis protein Tri7, which are acetyltransferases; and Cation transporting ATPase (the above-mentioned enzymes are all derived from *Aspergillus fumigatus* Af293 strain), a high homology of 70% or more was seen in any search.

The nucleotides 3342 to 5158 of SEQ ID NO:266 encode Adenylate-forming enzyme and the corresponding polypeptide is shown with the amino acid sequence depicted in SEQ ID NO:267; the nucleotides 5382 to 12777 of SEQ ID NO:266 encode LovB-like polyketide synthase and the corresponding polypeptide is shown with the amino acid sequence depicted in SEQ ID NO:268; the nucleotides 13266 to 15144 of SEQ ID NO:266 (hereinafter, a protein encoded by this polynucleotide sequence (P450-1) is referred to as Cytochrome P450 monooxygenase (1)) and the nucleotides 16220 to 18018 (hereinafter, a protein encoded by this polynucleotide sequence (P450-2) is referred to as Cytochrome P450 monooxygenase (2)) encode Cytochrome P450 monooxygenases and the corresponding polypeptides are shown with the amino acid sequences depicted in SEQ ID NOs:269 and 270, respectively; the nucleotides 18506 to 19296 of SEQ ID NO:266 encode Integral membrane protein and the corresponding polypeptide is shown with the amino acid sequence depicted in SEQ ID NO:271; the nucleotides 19779 to 21389 of SEQ ID NO:266 encode FAD-dependent monooxygenase and the corresponding polypeptide is shown with the amino acid sequence depicted in SEQ ID NO:272; the nucleotides 21793 to 22877 of SEQ ID NO:266 encode UbiA-like prenyltransferase and the corresponding polypeptide is shown with the amino acid sequence depicted in SEQ ID NO:273; the nucleotides 23205 to 24773 of SEQ ID NO:266 encode Acetyltransferase and the corresponding polypeptide is shown with the amino acid sequence depicted in SEQ ID NO:274; the nucleotides 25824 to 27178 of SEQ ID NO:266 encode Toxin biosynthesis protein Tri7 and the corresponding polypeptide is shown with the amino acid sequence depicted in SEQ ID NO:275; and the nucleotides 27798 to 31855 of SEQ ID NO:266 encode Cation transporting ATPase and the corresponding polypeptide is shown with the amino acid sequence depicted in SEQ ID NO:276.

Example 11

Hydroxylation of Pyripyropene E or Pyripyropene O by Transformation of *Aspergillus Oryzae*

Pyripyropene E used below can be produced by, for example, a method for culturing a microorganism based on the method described in Japanese Patent Laid-Open Publication No. 239385/1996 (Patent Document 4), WO94/09147 or U.S. Pat. No. 5,597,835, or the total synthesis method described in Tetrahedron Letters, vol. 37, No. 36, 6461-6464, 1996. Also, pyripyropene O used below can be produced by, for example, a method for culturing a microorganism based on the method described in J. Antibiotics 49, 292-298, 1996 or WO94/09147.

Figure 4:
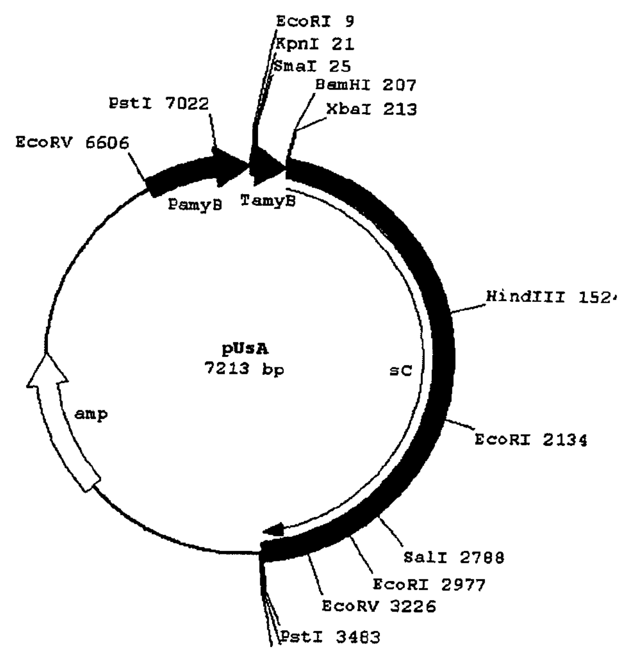
FIG. 4 shows the plasmid map of pUSA.

(1) Preparation of Expression Vector for Introducing into Filamentous Bacterium pUSA (FIG. 4) and pHSG399 (Takara Bio Inc.) were individually digested with KpnI and ligated, thereby obtaining pUSA-HSG. This plasmid was digested with SmaI and KpnI in the order mentioned, and subjected to gel purification, thereby obtaining a linear vector DNA having a KpnI cohesive end and SmaI blunt end.

(2) Preparation of Plasmid pPP2

Figure 5:
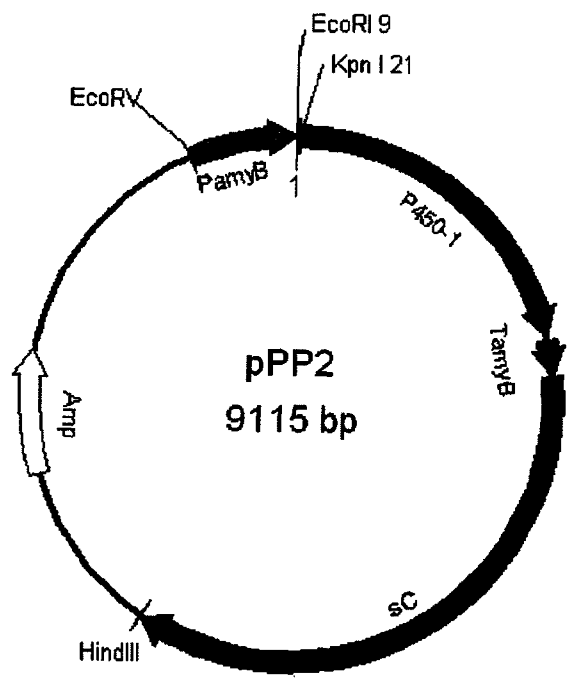
FIG. 5 shows the plasmid map of pPP2.

With fosmid pCC1-PP1 as a template, the polynucleotide of the above-mentioned P450-1 was amplified using a primer pair P450-1 with Kpn F (SEQ ID NO:277)/P450-1 with Swa R (SEQ ID NO:278). The purified DNA fragment was cloned into pCR-Blunt (Invitorogen, Cat. No. K2700-20). The plasmid obtained was digested with KpnI and SwaI. The above-mentioned P450-1 fragment was ligated to the above-described vector pUSA-HSG. thereby obtaining a plasmid pPP2 shown in FIG. 5.

(3) Preparation of Plasmid pPP3

Figure 6:
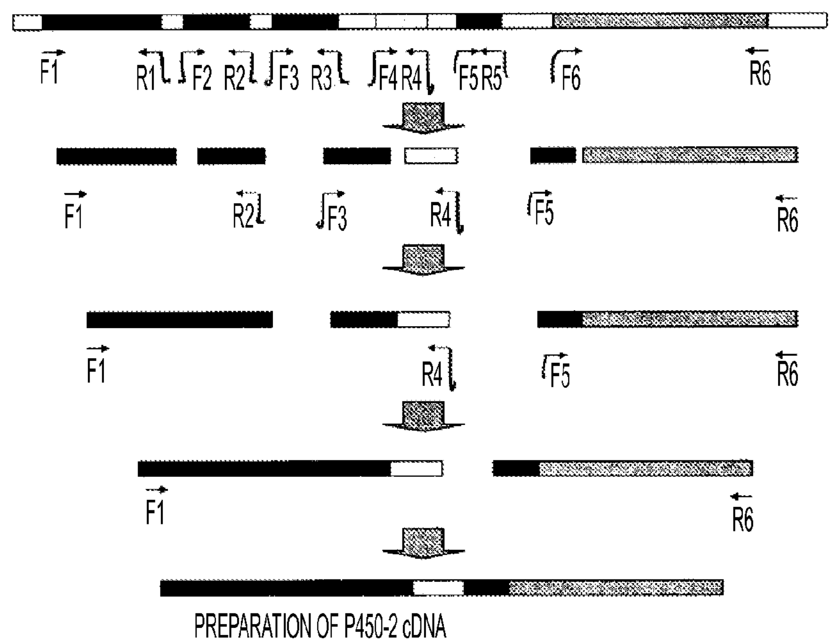
FIG. 6 shows a scheme of P450-2 cDNA amplification.
Figure 7:
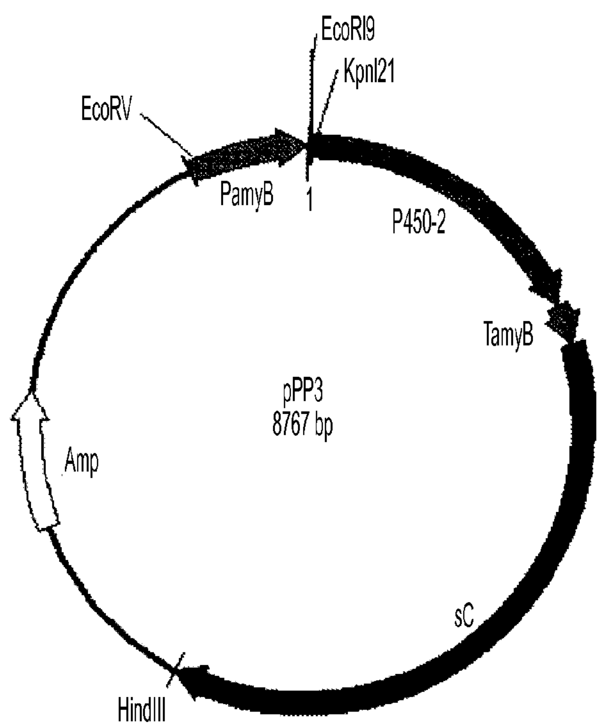
FIG. 7 shows the plasmid map of pPP3.

With fosmid pCC1-PP1 as a template, in accordance with the flow shown in FIG. 6, exons alone were first amplified using primer pairs F1 (SEQ ID NO:279)/R1 (SEQ ID NO:280), F2 (SEQ ID NO:281)/R2 (SEQ ID NO:282), F3 (SEQ ID NO:283)/R3 (SEQ ID NO:284), F4 (SEQ ID NO:285)/R4 (SEQ ID NO:286), F5 (SEQ ID NO:287)/R5 (SEQ ID NO:288) and F6 (SEQ ID NO:289)/R6 (SEQ ID NO:290), thereby obtaining six fragments. Next, amplification was carried out with these fragments as templates using primer pairs of F1/R2, F3/R4 and F5/R6, thereby obtaining longer fragments. Further, by repeating amplification using primer pairs of F1/R4 and F1/R6, cDNA which did not contain introns of the polynucleotide of the above-mentioned P450-2 was prepared. This cDNA fragment was inserted into pCR-Blunt (Invitorogen, Cat. No. K2700-20) and the obtained plasmid was used as a template for amplification by a primer pair, infusion F of P450-2-cDNA (SEQ ID NO:291)/infusion R of P450-2-cDNA (SEQ ID NO:292). Based on the manual of the kit, a plasmid pPP3 shown in FIG. 7 was obtained using In-Fusion Advantage PCR Cloning Kit (Clontech).

(4) Transformation of *Aspergillus Oryzae* (*A. oryzae*)

In a CD-Met (containing L-Methionine 40 μg/ml) agar medium, *A. oryzae* (HL-1105 strain) was cultured at 30° C. for one week. From this petri dish, conidia (>$10^8$) were collected and seeded in 100 ml of YPD liquid medium in a 500 ml-flask. After 20-hour culturing (30° C., 180 rpm), bacterial cells having a moss ball shape were obtained. The bacterial cells were collected with a 3G-1 glass filter, washed with 0.8 M NaCl, and water was removed well. The resultant was suspended with TF solution I (protoplast formation solution) and then shook at 30° C., at 60 rpm for 2 hours. At a 30-minute interval, observation under the microscope was carried out and the presence of protoplasts was checked. Thereafter, the culture medium was filtered and subjected to centrifugation (2000 rpm, 5 minutes) to collect protoplasts, which were then washed with TF solution II. After washing, 0.8 volume of TF solution II and 0.2 volume of TF solution III were added and mixed, thereby obtaining a protoplast suspension.

To 200 μl of this suspension, 10 μg of plasmid DNA (pPP2 or pPP3) was added. The mixture was left to stand on ice 30 minutes and added with TF solution III (1 mL). The resulting mixture was gently mixed and then left to stand at room temperature for 15 minutes. Thereafter, the plasmid DNA was introduced into the above-mentioned protoplasts. To this, TF solution II (8 mL) was added and subjected to centrifugation (at 2000 rpm for 5 minutes). Further, protoplasts were then recovered with 1 to 2 ml being left over. The recovered protoplast solution was dropped to a regeneration medium (lower layer) and a regeneration medium (upper layer) was poured. The resultant was mixed by turning a petri dish and then cultured at 30° C. for 4 to 5 days. Generated clones were isolated in the regeneration medium (lower layer), subcultured and purified, thereby obtaining a transformant (*Aspergillus oryzae* PP2-1 and *Aspergillus oryzae* PP3-2).

The above-mentioned TF solution I (protoplast formation solution) was prepared with the following compositions.

| Name of Compound | Concentration |
|---|---|
| Yatalase (manufactured by Takara Bio Inc.) | 20 mg/ml |
| Ammonium sulfate | 0.6M |
| Maleic acid-NaOH | 50 mM |

After the above-mentioned compositions (pH5.5) were prepared, filter sterilization was carried out.

The above-mentioned TF solution II was prepared with the following compositions.

| Name of Compound | | |
|---|---|---|
| 1.2M Sorbitol (MW = 182.17) | 43.72 | g |
| 50 mM $CaCl_2$ | 10 | ml 1M $CaCl_2$ (1/20) |
| 35 mM NaCl | 1.4 | ml 5M NaCl |
| 10 mM Tris-HCl | 2 | ml 1M Tris-HCl (1/100) |
| Up to total volume | 200 | ml |

After the above-mentioned compositions were prepared, autoclave sterilization was carried out.

The above-mentioned TF solution III was prepared with the following compositions.

| Name of Compound | | |
|---|---|---|
| 60% PEG4000 | 6 | g |
| 50 mM $CaCl_2$ | 500 | μl 1M $CaCl_2$ (1/20) |
| 50 mM Tris-HCl | 500 | μl 1M Tris-HCl (1/100) |
| Up to total volume | 10 | ml |

After the above-mentioned compositions were prepared, filter sterilization was carried out.

The above-mentioned regeneration medium was prepared with the following compositions.

| Name of Compound | Concentration | |
|---|---|---|
| Sorbitol (MW = 182.17) | 218.6 | g 1.2M |
| $NaNO_3$ | 3.0 | g 0.3% (w/v) |
| KCl | 2.0 | g 0.2% (w/v) |
| $KH_2PO_4$ | 1.0 | g 0.1% (w/v) |
| $MgSO_4 \cdot 7H_2O$ | 2 | ml of 1M $MgSO_4$ 0.05% 2 mM |
| Trace elements solution | 1 | ml |
| Glucose | 20.0 | g 2% (w/v) |
| Up to the total volume | 1 | L |

After the above-mentioned compositions (pH5.5) were prepared, autoclave sterilization was carried out.

In addition, the Trace elements solution used above was prepared with the following composition.

| Name of Compound | | |
|---|---|---|
| $FeSO_4 \cdot 7H_2O$ | 1.0 | g |
| $ZnSO_4 \cdot 7H_2O$ | 8.8 | g |
| $CuSO_4 \cdot 5H_2O$ | 0.4 | g |
| $Na_2B_4O_7 \cdot 10H_2O$ | 0.1 | g |
| $(NH_4)_6Mo_7O_{24} \cdot 4H_2O$ | 0.05 | g |
| Up to the total volume | 1 | L |

After the above-mentioned compositions were prepared, autoclave sterilization was carried out.

(5) Function Analysis and Addition Culture Test of P450-1

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of pyripyropene E was added to provide medium A. From flora of *Aspergillus oryzae* PP2-1 cultured in Czapek Dox agar medium, conidia thereof were collected and suspended in sterilized water. This conidia suspension was adjusted to $10^4$ spores/mL. Further, 100 μL of this adjusted conidia suspension was added to 10 mL of medium A and cultured with shaking at 25° C. for 96 hours. To this culture solution, 10 mL of acetone was added and the mixture was mixed well. Thereafter, acetone was removed using a centrifugal concentrator. To this, 10 mL of ethyl acetate was added and the resulting mixture was mixed well and then only the ethyl acetate layer was recovered. A dried product obtained by removing ethyl acetate using the centrifugal concentrator was dissolved in 1000 μL of methanol. This was used as a sample and analyzed by LC-MS (Waters, Micromass ZQ, 2996PDA, 2695 Separation module, Column: Waters XTerra C18 (ϕ4.5×50 mm, 5 μm)) and LC-NMR (Avance500 manufactured by Burker Daltonik).

As the results of the above-mentioned LC-MS measurement, it was confirmed that the obtained compound was single compound A which increased by a molecular weight of 16 compared with pyripyropene E. In addition, as the results of the LC-NMR measurement, it was confirmed that this compound A was an 11-position hydroxide of pyripyropene E. It was confirmed that the above-mentioned Cytochrome P450 monooxygenase (1) was an enzyme hydroxylating the 11-position of pyripyropene E with pyripyropene E as a substrate.

Physicochemical properties of the above-mentioned compound A are shown below:

1. Mass spectrum: ES-MS 468M/Z $(M+H)^+$
2. Molecular formula: $C_{27}H_{33}NO_6$
3. HPLC: Column: Waters XTerra Column C18 (5 μm, 4.6 mm×50 mm), 40° C., Mobile phase: From 20% aqueous acetonitrile solution to 100% acetonitrile in 10 minutes (linear gradient), Flow rate: 0.8 ml/min, Detection: Retention time 6.696 minutes at UV 323 nm
4. $^1$H-NMR spectrum ($CD_3CN$, 2H: 3.134, 3.157H-11)

Figure 8:
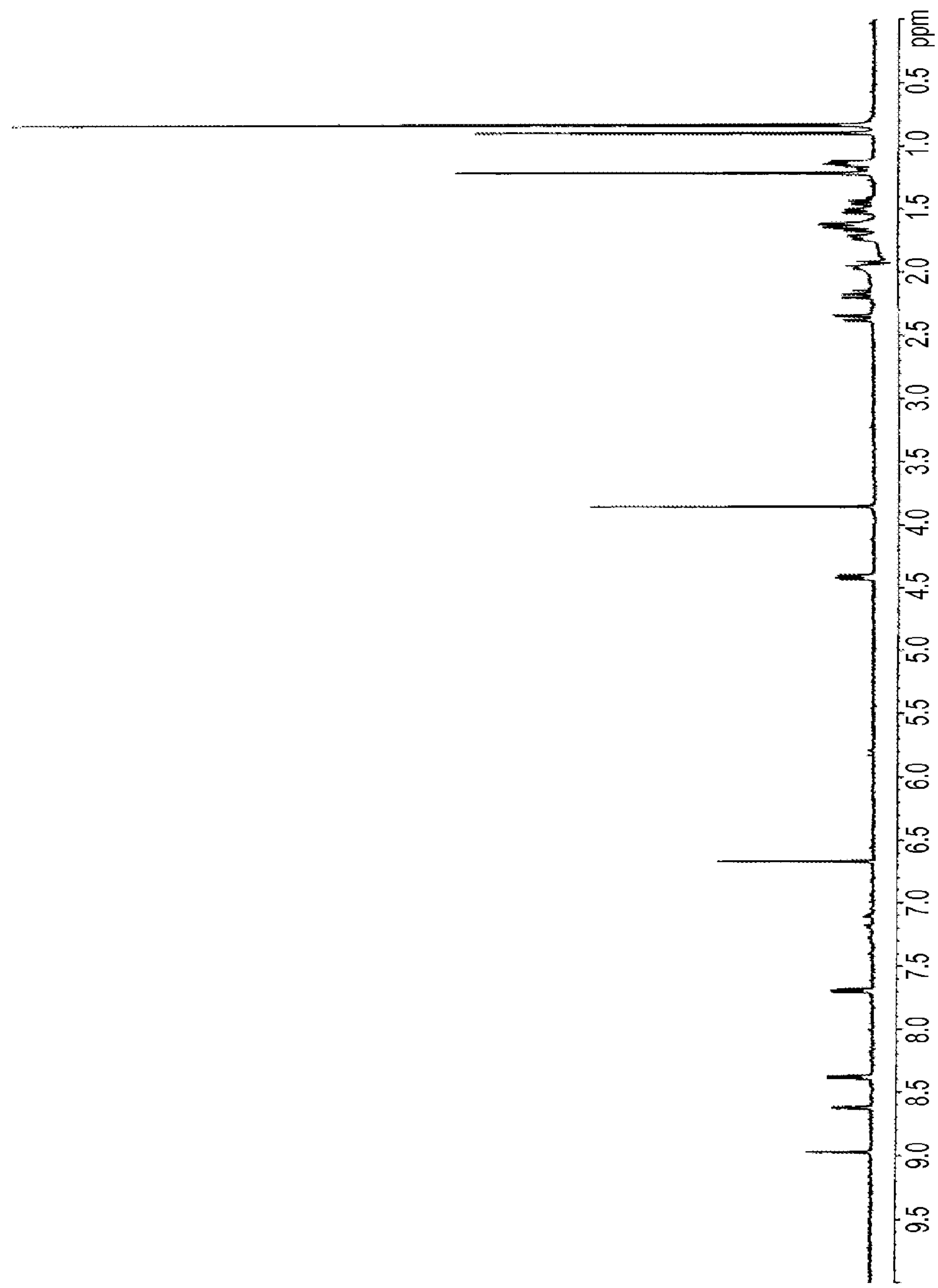
FIG. 8 shows $^{1}$H-NMR spectrum of pyripyropene E in deuterated acetonitrile.
Figure 9:
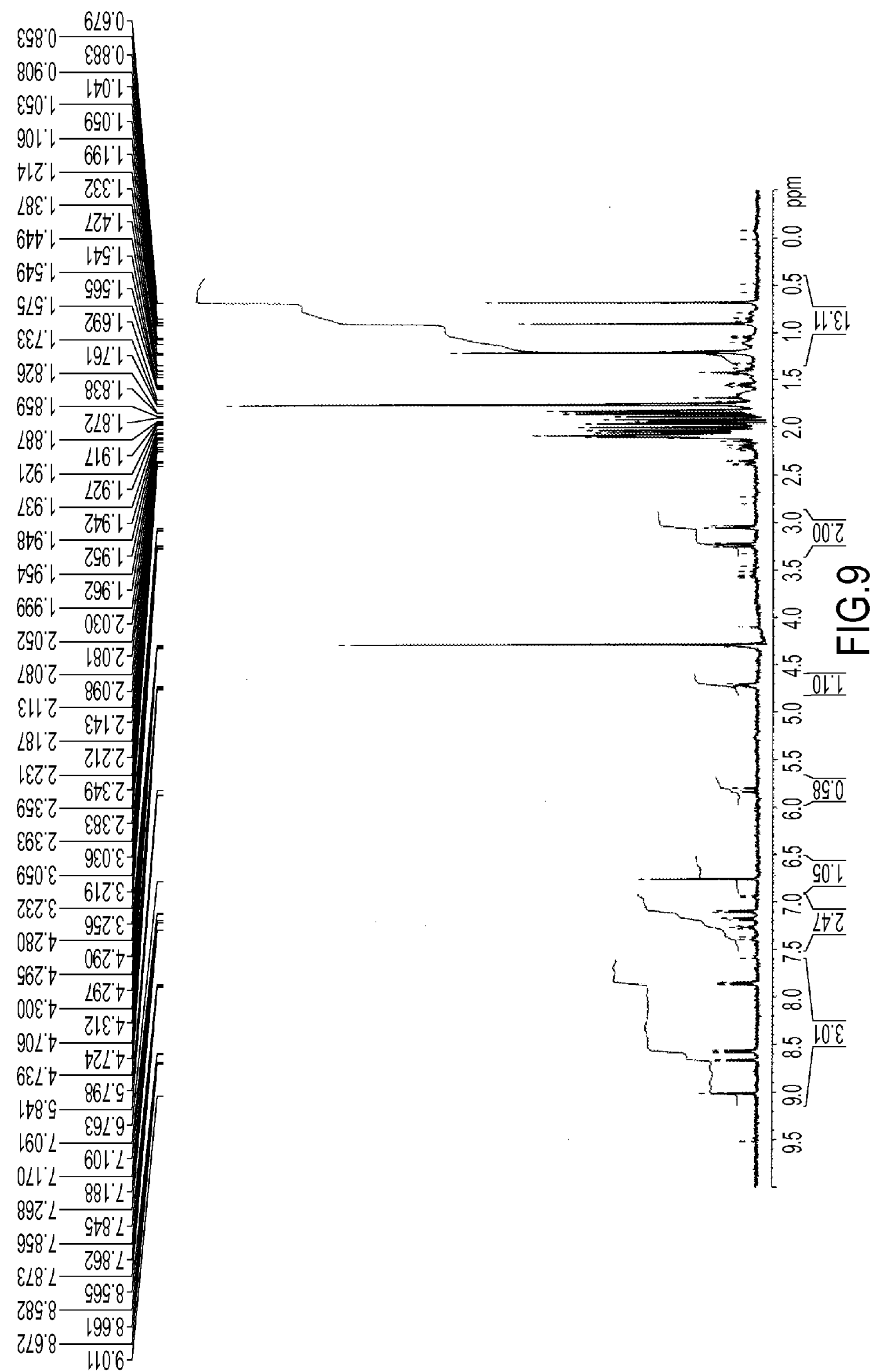
FIG. 9 shows $^{1}$H-NMR spectrum in deuterated acetonitrile of a product of the culture of *Aspergillus oryzae* transformed with plasmid pPP2.

The charts of the $^1$H-NMR spectrum of pyripyropene E and $^1$H-NMR spectrum according to 4 described above are shown in FIG. 8 and FIG. 9, respectively.

(6) Function Analysis and Addition Culture Test of P450-2

To a YPD medium (1% (w/v) Yeast Extract, 2% (w/v) Peptone, 2% (w/v) Dextrose) containing 1% (w/v) maltose, a 1/100 volume of 2 mg/mL dimethyl sulfoxide solution of pyripyropene E was added to provide medium B, and similarly a 1/100 volume of 2 mg/mL dimethyl sulfoxide solution of pyripyropene O was added to provide medium C. From flora of *Aspergillus oryzae* PP3-2 cultured in Czapek Dox agar medium, conidia thereof were collected and suspended in sterilized water. This conidia suspension was adjusted to $10^4$ spores/mL. Further, 500 μL of the adjusted conidia suspension was added to 50 mL of medium B or medium C and cultured with shaking at 25° C. for 96 hours. To this culture solution, 50 mL of acetone was added and the mixture was mixed well. Thereafter, acetone was removed using a centrifugal concentrator. To this, 50 mL of ethyl acetate was added and the resulting mixture was mixed well and then only the ethyl acetate layer was recovered. A dried product obtained by removing ethyl acetate using the centrifugal concentrator was dissolved in 1500 μL of methanol. This was used as a sample and analyzed by LC-MS (manufactured by Waters, Micromass ZQ, 2996PDA, 2695 Separation module, Column: Waters XTerra C18 (ϕ4.5×50 mm, 5 μm)) and LC-NMR (manufactured by Burker Daltonik, Avance500). As the results of the LC-MS measurement, from a sample obtained from the medium B, compound B which increased by a molecular weight of 32 compared with pyripyropene E was detected. Also, from a sample obtained from the medium C, compound C which increased by a molecular weight of 32 compared with pyripyropene O was detected. Further, as the results of the LC-NMR measurement, it was confirmed that the compound C was a 7-position and 13-position hydroxide of pyripyropene O. It was confirmed that the above-mentioned Cytochrome P450 monooxygenase (2) was an enzyme hydroxylating the 7-position and 13-position of each of pyripyropene E or pyripyropene O.

Physicochemical properties of the above-mentioned compound B are shown below:

1. Mass spectrum: ES-MS 484M/Z $(M+H)^+$

2. Molecular formula: $C_{27}H_{33}NO_7$

3. HPLC: Column: Waters XTerra Column C18 (5 μm, 4.6 mm×50 mm), 40° C., Mobile phase: From 20% aqueous acetonitrile solution to 100% acetonitrile in 10 minutes (linear gradient), Flow rate: 0.8 ml/min, Detection: Retention time 5.614 minutes at UV 323 nm Physicochemical properties of the above-mentioned compound C are shown below:

1. Mass spectrum: ES-MS 542M/Z $(M+H)^+$

2. Molecular formula: $C_{29}H_{35}NO_9$

3. HPLC: Column: Waters XTerra Column C18 (5 μm, 4.6 mm×50 mm), 40° C., Mobile phase: From 20% aqueous acetonitrile solution to 100% acetonitrile in 10 minutes (linear gradient), Flow rate: 0.8 ml/min, Detection: Retention time 5.165 minutes at UV 323 nm 4. $^1$H-NMR spectrum ($CD_3CN$, 1H 4.858H-13), ($CD_3CN$, 1H 3.65H-7)

Figure 10:
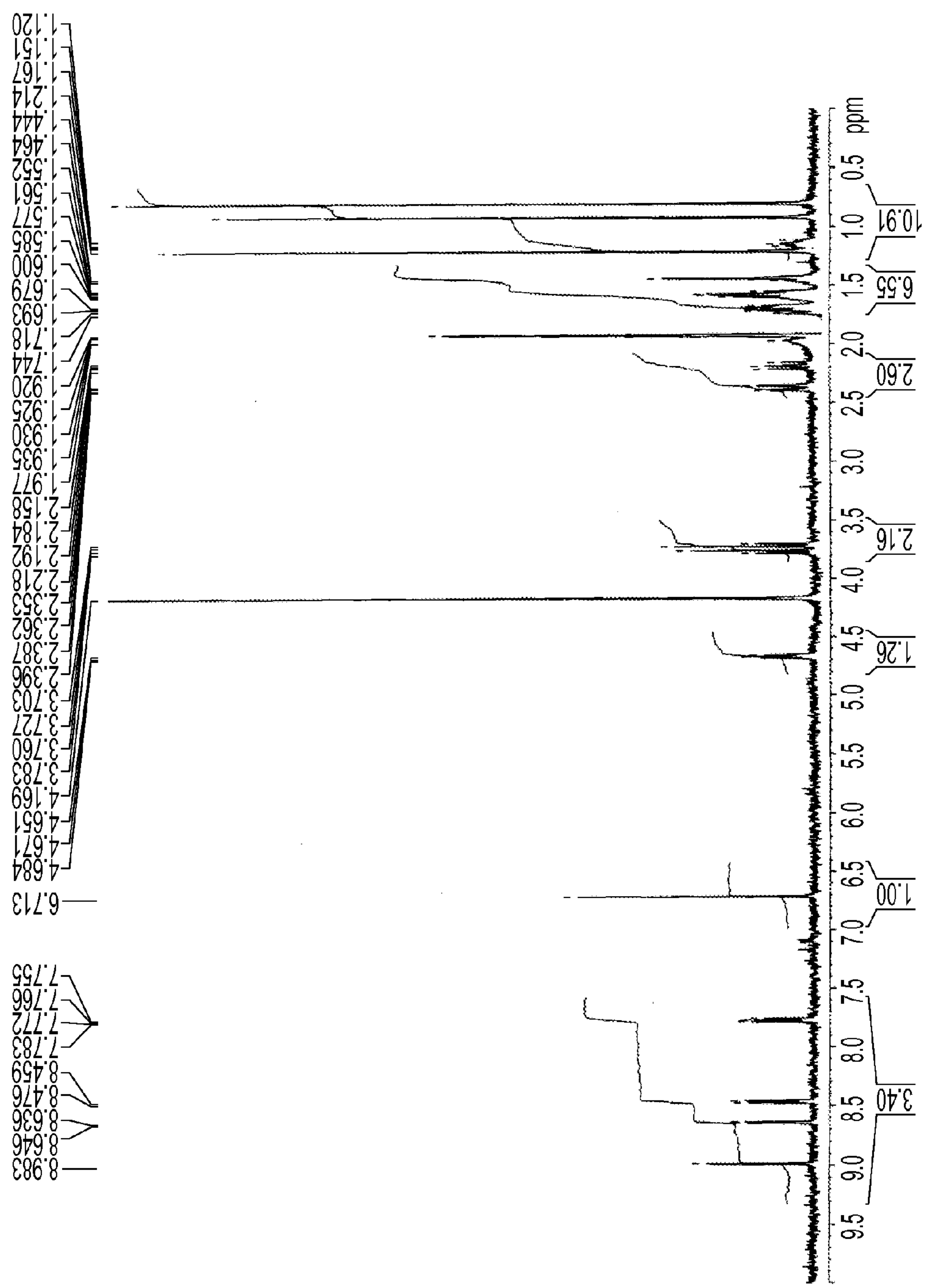
FIG. 10 shows $^{1}$H-NMR spectrum of pyripyropene O in deuterated acetonitrile.
Figure 11:
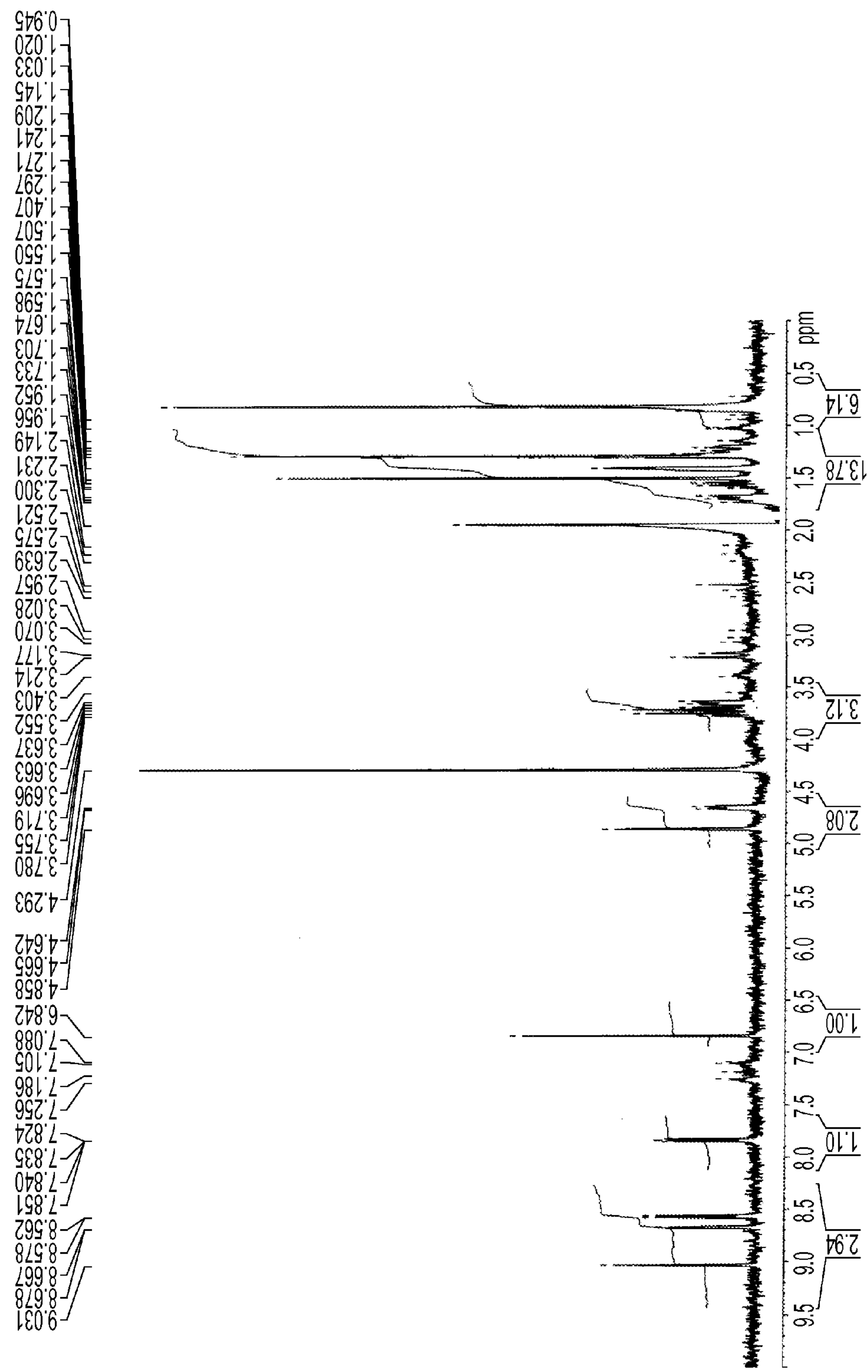
FIG. 11 shows $^{1}$H-NMR spectrum in deuterated acetonitrile of a product of the culture of *Aspergillus oryzae* transformed with plasmid pPP3.

The charts of the $^1$H-NMR spectrum of pyripyropene O and the above-mentioned compound C are shown in FIG. 10 and FIG. 11, respectively.

[Accession Numbers]

FERM BP-11133

FERM BP-11137

FERM BP-11141

The invention claimed is:

1. An isolated polynucleotide comprising a selection marker, and (a) a polynucleotide having a polynucleotide sequence encoding at least one amino acid sequence selected from SEQ ID NOs: 267 to 274 or an amino acid sequence selected from SEQ ID Nos: 267 to 274 having 1 to 40 substituted, deleted, added or inserted residues and having the same enzymatic activity as SEQ ID NOs: 267 to 274, respectively, or (b) a polynucleotide having a nucleotide sequence which is capable of hybridizing with the nucleotide sequence of SEQ ID NO: 266 under stringent conditions comprising washing in a solution comprising 30 mM trisodium citrate, 300 mM sodium chloride and 0.5% sodium dodecyl sulfate at 60° C. for 20 minutes and having the same enzymatic activity as SEQ ID NO: 266, wherein the polynucleotide of (a) or (b) is a cDNA.

2. An isolated cDNA, which has at least one nucleotide sequence selected from the nucleotide sequence of any of (1) or (2) below:

(1) a nucleotide sequence of any of (a) to (h) below:

(a) a nucleotide sequence from positions 3342 to 5158 of the nucleotide sequence shown in SEQ ID NO: 266, (b) a nucleotide sequence from positions 5382 to 12777 of the nucleotide sequence shown in SEQ ID NO: 266, (c) a nucleotide sequence from positions 13266 to 15144 of the nucleotide sequence shown in SEQ ID NO: 266, (d) a nucleotide sequence from positions 16220 to 18018 of the nucleotide sequence shown in SEQ ID NO: 266, (e) a nucleotide sequence from positions 18506 to 19296 of the nucleotide sequence shown in SEQ ID NO: 266, (f) a nucleotide sequence from positions 19779 to 21389 of the nucleotide sequence shown in SEQ ID NO: 266, (g) a nucleotide sequence from positions 21793 to 22877 of the nucleotide sequence shown in SEQ ID NO: 266, (h) a nucleotide sequence from positions 23205 to 24773 of the nucleotide sequence shown in SEQ ID NO:266;

(2) a nucleotide sequence which is capable of hybridizing with the nucleotide sequence of (1) under stringent conditions comprising washing in a solution comprising 30 mM trisodium citrate, 300 mM sodium chloride and 0.5% sodium dodecyl sulfate at 60° C. for 20 minutes, wherein the nucleotide sequences corresponding to (1) (a) to (h) and (2) encode the same enzymatic activity as the sequences of SEQ IDS Nos: 267 to 274, respectively.

3. The polynucleotide according to claim 1, encoding at least one polypeptide involved in biosynthesis of pyripyropene A.

4. The polynucleotide according to claim 1, encoding a polypeptide having any one or more activities selected from the group consisting of polyketide synthase activity, prenyltransferase activity, hydroxylase activity, acetyltransferase activity and adenylate synthetase activity.

5. The polynucleotide according to claim 1, encoding a polypeptide having hydroxylase activity.

6. The polynucleotide according to claim 1, which is derived from *Penicillium coprobium* PF1169 strain.

7. The polynucleotide according to claim 1, encoding a polypeptide having a 7-position and/or a 13-position of pyripyropene E or pyripyropene O hydroxylating activity.

8. The polynucleotide according to claim 1, encoding a polypeptide having an 11-position of pyripyropene E hydroxylating activity.

* * * * *

SEQUENCE LISTING

```
<160> NUMBER OF SEQ ID NOS: 292

<210> SEQ ID NO 1
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 1

gayccnmgnt tyttyaayat g                                              21


<210> SEQ ID NO 2
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (9)..(9)
<223> OTHER INFORMATION: I

<400> SEQUENCE: 2

gtnccngtnc crtgcatytc                                                20


<210> SEQ ID NO 3
<211> LENGTH: 500
<212> TYPE: DNA
<213> ORGANISM: Artificial Sequence
```

<220> FEATURE:
<223> OTHER INFORMATION: Synthetic construct

<400> SEQUENCE: 3

```
cattaccgag tgagggccct ctgggtccaa cctcccaccc gtgtttattt accttgttgc     60

ttcggcgggc ccgccttaac tggccgccgg ggggcttacg cccccgggcc cgcgcccgcc    120

gaagacaccc tcgaactctg tctgaagatt gtagtctgag tataaatata aattatttaa    180

aactttcaac aacggatctc ttggttccgg catcgatgaa gaacgcagcg aaatgcgata    240

cgtaatgtga attgcaaatt cagtgaatca tcgagtcttt gaacgcacat tgcgccccct    300

ggtattccgg ggggcatgcc tgtccgagcg tcattgctgc cctcaagccc ggcttgtgtg    360

ttgggccccg tcctccgatt ccgggggacg ggcccgaaag gcagcggcgg caccgcgtcc    420

ggtcctcgag cgtatggggc tttgtcaccc gctctgtagg cccggccggc gcttgccgat    480

caacccaaat ttttatccag                                                500
```

<210> SEQ ID NO 4
<211> LENGTH: 28
<212> TYPE: PRT
<213> ORGANISM: Penicillium coprobium PF1169

<400> SEQUENCE: 4

```
Gln Pro Trp Lys Asp Ser Ile Trp Ala Gly Asp Val Tyr Met Phe Glu
1               5                   10                  15

Gly Asp Asp Ile Val Ala Val Tyr Gly Gly Val Lys
            20                  25
```

<210> SEQ ID NO 5
<211> LENGTH: 36
<212> TYPE: PRT
<213> ORGANISM: Penicillium coprobium PF1169

<400> SEQUENCE: 5

```
His Asn Ser Ile Phe Gln Ala Leu Ala Arg Lys Ile Leu Asp Met Ala
1               5                   10                  15

Leu Pro Pro Gly Gly Gly Ala Pro Ala Pro Ala Pro Ala Ala Lys Arg
            20                  25                  30

Pro Ala Pro Ile
        35
```

<210> SEQ ID NO 6
<211> LENGTH: 70
<212> TYPE: PRT
<213> ORGANISM: Penicillium coprobium PF1169

<400> SEQUENCE: 6

```
Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70
```

<210> SEQ ID NO 7

```
<211> LENGTH: 74
<212> TYPE: PRT
<213> ORGANISM: Penicillium coprobium PF1169

<400> SEQUENCE: 7

Arg Ile Ser Tyr Tyr Phe Asp Trp Gln Gly Pro Ser Met Ala Val Asp
1               5                   10                  15

Thr Gly Cys Ser Ser Ser Leu Leu Ala Val His Leu Gly Val Glu Ala
            20                  25                  30

Leu Gln Asn Asp Asp Cys Ser Met Ala Val Ala Val Gly Ser Asn Leu
        35                  40                  45

Ile Leu Ser Pro Asn Ala Tyr Ile Ala Asp Ser Lys Thr Arg Met Leu
    50                  55                  60

Ser Pro Thr Gly Arg Ser Arg Met Trp Asp
65                  70


<210> SEQ ID NO 8
<211> LENGTH: 51
<212> TYPE: PRT
<213> ORGANISM: Penicillium coprobium PF1169

<400> SEQUENCE: 8

Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
            20                  25                  30

Glu Phe Leu Glu Ala Ala Asn Gly His Arg Met Asn Asp Cys Gly Val
        35                  40                  45

Val Thr Ser
    50


<210> SEQ ID NO 9
<211> LENGTH: 79
<212> TYPE: PRT
<213> ORGANISM: Penicillium coprobium PF1169

<400> SEQUENCE: 9

Phe Asn Ala Ala His Arg Val Leu Pro Leu Pro Ser Tyr Lys Trp Asp
1               5                   10                  15

Leu Lys Asn Tyr Trp Ile Pro Tyr Thr Asn Asn Phe Cys Leu Leu Lys
            20                  25                  30

Gly Ala Pro Ala Ala Pro Val Ala Glu Ala Thr Pro Ile Ser Val Phe
        35                  40                  45

Leu Ser Ser Ala Ala Gln Arg Val Leu Glu Thr Ser Gly Asp Asn Ser
    50                  55                  60

Ser Ala Phe Ile Val Ile Glu Asn Asp Ile Ala Asp Pro Asp Leu
65                  70                  75


<210> SEQ ID NO 10
<211> LENGTH: 84
<212> TYPE: PRT
<213> ORGANISM: Penicillium coprobium PF1169

<400> SEQUENCE: 10

Val Ile Arg Gly Thr Gly Ser Asn Gln Asp Gly Arg Thr Ala Gly Ile
1               5                   10                  15

Thr Val Pro Asn Gly Ala Ala Gln Glu Ser Leu Ile Arg Ser Val Tyr
            20                  25                  30

Ala Gln Ala Asp Leu Asp Pro Ser Glu Thr Asp Phe Val Glu Ala His
```

```
        35                  40                  45

Gly Thr Gly Thr Leu Ala Gly Asp Pro Val Glu Thr Gly Ala Ile Ala
    50                  55                  60

Arg Val Phe Gly Thr Asp Arg Pro Pro Gly Asp Pro Val Arg Ile Gly
65                  70                  75                  80

Ser Ile Lys Thr


<210> SEQ ID NO 11
<211> LENGTH: 81
<212> TYPE: PRT
<213> ORGANISM: Penicillium coprobium PF1169

<400> SEQUENCE: 11

Gln Glu Ala Lys Ala Met Asp Pro Gln Gln Arg Met Leu Leu Glu Cys
1               5                   10                  15

Thr Tyr Glu Ala Leu Glu Asn Gly Gly Ile Ser Lys Glu Ser Leu Lys
            20                  25                  30

Gly Gln Asn Val Gly Val Phe Val Gly Ser Ala Phe Pro Asp Tyr Glu
        35                  40                  45

Met Tyr Asn Arg Arg Asp Leu Glu Thr Ala Pro Met His Gln Ser Thr
    50                  55                  60

Gly Asn Ala Leu Ala Leu Gln Ser Asn Arg Ile Ser Tyr Tyr Phe Asp
65                  70                  75                  80

Phe


<210> SEQ ID NO 12
<211> LENGTH: 66
<212> TYPE: PRT
<213> ORGANISM: Penicillium coprobium PF1169

<400> SEQUENCE: 12

Asn His Thr Gly Arg Ala Glu Gln Ser Lys Ile Ala Ile Ile Gly Leu
1               5                   10                  15

Ser Gly Arg Phe Pro Glu Ala Pro Asp Thr Glu Ala Phe Trp Asp Leu
            20                  25                  30

Leu Lys Lys Gly Leu Asp Val His Arg Glu Val Pro Pro Glu Arg Trp
        35                  40                  45

Asp Val Lys Ala His Val Asp Pro Glu Gly Lys Lys Arg Thr Pro Ala
    50                  55                  60

Lys Leu
65


<210> SEQ ID NO 13
<211> LENGTH: 14
<212> TYPE: PRT
<213> ORGANISM: Penicillium coprobium PF1169

<400> SEQUENCE: 13

Glu Lys Asn Thr Ser Gln Val Glu Tyr Gly Cys Trp Tyr Asn
1               5                   10


<210> SEQ ID NO 14
<211> LENGTH: 71
<212> TYPE: PRT
<213> ORGANISM: Penicillium coprobium PF1169

<400> SEQUENCE: 14

Ala Gly Gly Asn Thr Thr Val Ala Leu Glu Asp Ala Pro Ile Arg Thr
1               5                   10                  15
```

```
Arg Ser Gly Ser Asp Pro Arg Ser Leu His Pro Ile Ala Ile Ser Ala
            20                  25                  30

Lys Ser Lys Val Ser Leu Arg Gly Asn Leu Glu Asn Leu Leu Ala Tyr
        35                  40                  45

Leu Asp Thr His Pro Asp Val Ser Leu Ser Asp Leu Ser Tyr Thr Thr
    50                  55                  60

Thr Ala Arg Arg His His His
65                  70


<210> SEQ ID NO 15
<211> LENGTH: 77
<212> TYPE: PRT
<213> ORGANISM: Penicillium coprobium PF1169

<400> SEQUENCE: 15

Ala Thr Asp Thr Glu Lys Phe Trp Asp Leu Leu Ala Ser Gly Val Asp
1               5                   10                  15

Val His Arg Lys Ile Pro Ala Asp Arg Phe Asp Val Glu Thr His Tyr
            20                  25                  30

Asp Pro Asn Gly Lys Arg Met Asn Ala Ser His Thr Pro Tyr Gly Cys
        35                  40                  45

Phe Ile Asp Glu Pro Gly Leu Phe Asp Ala Ala Phe Phe Asn Met Ser
    50                  55                  60

Pro Arg Glu Ala Gln Gln Thr Asp Pro Met Gln Arg Leu
65                  70                  75


<210> SEQ ID NO 16
<211> LENGTH: 39
<212> TYPE: PRT
<213> ORGANISM: Penicillium coprobium PF1169

<400> SEQUENCE: 16

Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
            20                  25                  30

Ser Ser Gly Glu Ile Ala Ala
        35


<210> SEQ ID NO 17
<211> LENGTH: 71
<212> TYPE: PRT
<213> ORGANISM: Penicillium coprobium PF1169

<400> SEQUENCE: 17

Arg Arg Thr Phe Leu Pro Trp Arg Leu Thr Ser Ser Ala Leu Ser Gly
1               5                   10                  15

Gln Glu Leu Thr Gln Ser Leu Ala Ile Asp Ala Val Pro Ile Arg Ser
            20                  25                  30

Ser Lys Glu Pro Thr Val Gly Phe Val Phe Thr Gly Gln Gly Ala Gln
        35                  40                  45

Trp His Gly Met Gly Lys Glu Leu Leu Ser Thr Tyr Pro Ile Phe Arg
    50                  55                  60

Gln Thr Met Gln Asp Val Asp
65                  70


<210> SEQ ID NO 18
<211> LENGTH: 75
```

<212> TYPE: PRT
<213> ORGANISM: Penicillium coprobium PF1169

<400> SEQUENCE: 18

```
Leu Arg Arg Leu Leu His Ala Lys Asn Asp Ser Leu Val Ala Ala Phe
1               5                   10                  15

Phe Gln Lys Thr Tyr Cys Ala Leu Arg Lys Glu Ile Thr Ser Leu Pro
            20                  25                  30

Pro Ser Glu Arg Gln Val Phe Pro Arg Phe Thr Ser Ile Val Asp Leu
        35                  40                  45

Leu Ala Arg Phe Lys Glu Phe Gly Pro Asn Pro Ala Leu Glu Ser Ala
    50                  55                  60

Leu Thr Thr Ile Tyr Gln Leu Gly Cys Phe Ile
65                  70                  75
```

<210> SEQ ID NO 19
<211> LENGTH: 81
<212> TYPE: PRT
<213> ORGANISM: Penicillium coprobium PF1169

<400> SEQUENCE: 19

```
Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
    50                  55                  60

Thr Ala Gln Glu Ile Ser Thr Tyr Phe Ile Pro Gly Gly Cys Arg Ala
65                  70                  75                  80

Phe
```

<210> SEQ ID NO 20
<211> LENGTH: 38
<212> TYPE: PRT
<213> ORGANISM: Penicillium coprobium PF1169

<400> SEQUENCE: 20

```
Asp Thr Ala Cys Ser Ser Ser Leu Val Ala Leu His Tyr Ala Val Gln
1               5                   10                  15

Ser Leu Arg Asn Gly Glu Ser Thr Glu Ala Leu Ile Ala Gly Cys His
            20                  25                  30

Leu Asn Ile Val Pro Asp
        35
```

<210> SEQ ID NO 21
<211> LENGTH: 75
<212> TYPE: PRT
<213> ORGANISM: Penicillium coprobium PF1169

<400> SEQUENCE: 21

```
Ala Lys His Pro Pro Ala Thr Ser Ile Leu Leu Gln Gly Asn Pro Lys
1               5                   10                  15

Thr Ala Thr Gln Ser Leu Phe Leu Phe Pro Asp Gly Ser Gly Ser Ala
            20                  25                  30

Thr Ser Tyr Ala Thr Ile Pro Gly Ile Ser Pro Asp Val Cys Val Tyr
        35                  40                  45
```

```
Gly Leu Asn Cys Pro Tyr Met Arg Thr Pro Glu Lys Leu Lys Phe Ser
    50                  55                  60

Leu Asp Glu Leu Thr Ala Pro Tyr Val Ala Glu
65                  70                  75


<210> SEQ ID NO 22
<211> LENGTH: 38
<212> TYPE: PRT
<213> ORGANISM: Penicillium coprobium PF1169

<400> SEQUENCE: 22

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35


<210> SEQ ID NO 23
<211> LENGTH: 57
<212> TYPE: PRT
<213> ORGANISM: Penicillium coprobium PF1169

<400> SEQUENCE: 23

Ala Ile Arg Asp Glu Val Arg Gln Leu Pro Thr Pro Leu Arg Ala Leu
1               5                   10                  15

Val Pro Ala Phe Glu Asn Val Leu Glu Leu Ala Asn Tyr Thr Asp Leu
            20                  25                  30

Arg Lys Gly Pro Leu Ser Gly Ser Ile Asp Gly Val Leu Leu Cys Val
        35                  40                  45

Val Gln Leu Ser Ser Leu Ile Gly Tyr
    50                  55


<210> SEQ ID NO 24
<211> LENGTH: 74
<212> TYPE: PRT
<213> ORGANISM: Penicillium coprobium PF1169

<400> SEQUENCE: 24

Ala Val Ala Trp Asp Pro Gln Gln Arg Ile Leu Leu Glu Val Val Tyr
1               5                   10                  15

Glu Ala Leu Glu Ser Ala Gly Tyr Phe Arg Ala Gly Ile Lys Pro Glu
            20                  25                  30

Leu Asp Asp Tyr Gly Cys Tyr Ile Gly Ala Val Met Asn Asn Tyr Tyr
        35                  40                  45

Asp Asn Met Ser Cys Gln Pro Thr Thr Ala Tyr Ala Thr Val Gly Thr
    50                  55                  60

Ser Arg Cys Phe Leu Ser Gly Cys Val Ser
65                  70


<210> SEQ ID NO 25
<211> LENGTH: 52
<212> TYPE: PRT
<213> ORGANISM: Penicillium coprobium PF1169

<400> SEQUENCE: 25

Gly Val Ile Val Gly Ser Ala Ala Asn Gln Asn Leu Asn Leu Ser His
1               5                   10                  15

Ile Thr Val Pro His Ser Gly Ser Gln Val Lys Leu Tyr Gln Asn Val
            20                  25                  30
```

```
Met Ser Gln Ala Gly Val His Pro His Ser Val Thr Tyr Val Glu Ala
        35                  40                  45

His Gly Thr Gly
    50


<210> SEQ ID NO 26
<211> LENGTH: 57
<212> TYPE: PRT
<213> ORGANISM: Penicillium coprobium PF1169

<400> SEQUENCE: 26

Trp Arg Ile Thr Val Ala Ile Val Gly Gly Val Asn Ala Leu Cys Gly
1               5                   10                  15

Pro Gly Leu Thr Arg Val Leu Asp Lys Ala Gly Ala Ile Ser Ser Asp
            20                  25                  30

Gly Ser Cys Lys Ser Phe Asp Asp Asp Ala His Gly Tyr Ala Arg Gly
        35                  40                  45

Glu Gly Ala Gly Ala Leu Val Leu Lys
    50                  55


<210> SEQ ID NO 27
<211> LENGTH: 78
<212> TYPE: PRT
<213> ORGANISM: Penicillium coprobium PF1169

<400> SEQUENCE: 27

Leu Ile Asp Asp Thr Thr Val Trp Ile Glu Ile Gly Pro His Pro Val
1               5                   10                  15

Cys Leu Gly Phe Val Lys Ala Thr Leu Glu Ser Val Ala Val Ala Val
            20                  25                  30

Pro Ser Leu Arg Arg Gly Glu Asn Ala Trp Cys Thr Leu Ala Gln Ser
        35                  40                  45

Leu Thr Thr Leu His Asn Ala Gly Val Pro Val Gly Trp Ser Glu Phe
    50                  55                  60

His Arg Pro Phe Glu Arg Ala Leu Cys Leu Leu Asp Leu Pro
65                  70                  75


<210> SEQ ID NO 28
<211> LENGTH: 65
<212> TYPE: PRT
<213> ORGANISM: Penicillium coprobium PF1169

<400> SEQUENCE: 28

Val Trp Ile Glu Ile Gly Pro His Pro Val Cys Leu Gly Phe Val Lys
1               5                   10                  15

Ala Thr Leu Glu Ser Val Ala Val Ala Val Pro Ser Leu Arg Arg Gly
            20                  25                  30

Glu Asn Ala Trp Cys Thr Leu Ala Gln Ser Leu Thr Thr Leu His Asn
        35                  40                  45

Ala Gly Val Pro Val Gly Trp Ser Glu Phe His Arg Pro Phe Glu Arg
    50                  55                  60

Ala
65


<210> SEQ ID NO 29
<211> LENGTH: 83
<212> TYPE: PRT
<213> ORGANISM: Penicillium coprobium PF1169
```

```
<400> SEQUENCE: 29

Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala Ala Ile His Val Ala Cys Asn Ser Leu Trp Arg
    50                  55                  60

Asn Glu Ser Asp Ser Ala Val Ala Gly Gly Val Asn Ile Leu Thr Asn
65                  70                  75                  80

Pro Asp Asn


<210> SEQ ID NO 30
<211> LENGTH: 54
<212> TYPE: PRT
<213> ORGANISM: Penicillium coprobium PF1169

<400> SEQUENCE: 30

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn
    50


<210> SEQ ID NO 31
<211> LENGTH: 63
<212> TYPE: PRT
<213> ORGANISM: Penicillium coprobium PF1169

<400> SEQUENCE: 31

Asp Thr Ala Cys Ser Ser Ser Leu Tyr Ala Leu His Ser Ala Cys Leu
1               5                   10                  15

Ala Leu Asp Ser Arg Asp Cys Asp Gly Ala Val Val Ala Ala Ala Asn
            20                  25                  30

Leu Ile Gln Ser Pro Glu Gln Gln Met Ile Ala Val Lys Ala Gly Ile
        35                  40                  45

Leu Ser Pro Asp Ser Met Cys His Thr Phe Asp Glu Ser Ala Asn
    50                  55                  60


<210> SEQ ID NO 32
<211> LENGTH: 55
<212> TYPE: PRT
<213> ORGANISM: Penicillium coprobium PF1169

<400> SEQUENCE: 32

Lys Gln Thr Thr Ser Arg Gly Tyr Phe Leu Asp His Leu Glu Asp Phe
1               5                   10                  15

Asp Cys Gln Phe Phe Gly Ile Ser Pro Lys Glu Ala Glu Gln Met Asp
            20                  25                  30

Pro Gln Gln Arg Val Ser Leu Glu Val Ala Ser Glu Ala Leu Glu Asp
        35                  40                  45

Ala Gly Ile Pro Ala Lys Ser
    50                  55
```

<210> SEQ ID NO 33
<211> LENGTH: 38
<212> TYPE: PRT
<213> ORGANISM: Penicillium coprobium PF1169

<400> SEQUENCE: 33

```
Pro Val Gly Cys Arg Ala Phe Gly Pro Gly Arg Ile Asn Tyr Phe Phe
1               5                   10                  15

Lys Phe Ser Gly Pro Ser Phe Ser Ile Asp Thr Ala Cys Ser Ser Ser
            20                  25                  30

Leu Ala Thr Ile Gln Val
        35
```

<210> SEQ ID NO 34
<211> LENGTH: 18
<212> TYPE: PRT
<213> ORGANISM: Penicillium coprobium PF1169

<400> SEQUENCE: 34

```
Ala Cys Thr Ser Leu Trp Asn Gly Glu Thr Asp Thr Val Val Ala Gly
1               5                   10                  15

Gly Met
```

<210> SEQ ID NO 35
<211> LENGTH: 12
<212> TYPE: PRT
<213> ORGANISM: Penicillium coprobium PF1169

<400> SEQUENCE: 35

```
Thr Ala Gln Glu Ile Ser Thr Tyr Phe Ile Pro Gly
1               5                   10
```

<210> SEQ ID NO 36
<211> LENGTH: 39
<212> TYPE: PRT
<213> ORGANISM: Penicillium coprobium PF1169

<400> SEQUENCE: 36

```
Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
            20                  25                  30

Ser Ser Gly Glu Ile Ala Ala
        35
```

<210> SEQ ID NO 37
<211> LENGTH: 36
<212> TYPE: PRT
<213> ORGANISM: Penicillium coprobium PF1169

<400> SEQUENCE: 37

```
Ile Ser Gln Pro Ala Cys Thr Ala Leu Gln Ile Ala Leu Val Asp Leu
1               5                   10                  15

Leu Ala Glu Trp Ser Ile Thr Pro Ser Val Val Val Gly His Ser Ser
            20                  25                  30

Gly Glu Ile Ala
        35
```

<210> SEQ ID NO 38
<211> LENGTH: 39
<212> TYPE: PRT

<213> ORGANISM: Penicillium coprobium PF1169

<400> SEQUENCE: 38

```
Pro Glu Tyr Ser Gln Pro Leu Cys Thr Ala Ile Gln Ile Ala Leu Val
1               5                   10                  15

Glu Leu Leu Glu Ser Phe Gly Val Val Pro Lys Ala Val Val Gly His
            20                  25                  30

Ser Ser Gly Glu Ile Ala Ala
        35
```

<210> SEQ ID NO 39
<211> LENGTH: 76
<212> TYPE: PRT
<213> ORGANISM: Penicillium coprobium PF1169

<400> SEQUENCE: 39

```
Glu Glu Phe Trp Asp Leu Cys Ser Arg Gly Arg Gly Ala Trp Ser Pro
1               5                   10                  15

Val Pro Lys Asp Arg Phe Asn Ala Gly Ser Phe Tyr His Pro Asn Ala
            20                  25                  30

Asp Arg Pro Gly Ser Phe Asn Ala Ala Gly Ala His Phe Leu Thr Glu
        35                  40                  45

Asp Ile Gly Leu Phe Asp Ala Pro Phe Phe Asn Ile Thr Leu Gln Glu
    50                  55                  60

Ala Gln Thr Met Asp Pro Gln Gln Arg Ile Phe Leu
65                  70                  75
```

<210> SEQ ID NO 40
<211> LENGTH: 77
<212> TYPE: PRT
<213> ORGANISM: Penicillium coprobium PF1169

<400> SEQUENCE: 40

```
Ile Asn Glu Pro Arg Asp Arg Pro Gln Phe Phe His Ala His Gly Thr
1               5                   10                  15

Gly Thr Gln Ala Gly Asp Pro Gln Glu Ala Glu Ala Val Ser Thr Ala
            20                  25                  30

Leu Phe Pro Asp Gly Ser Asn Ile Glu Thr Lys Leu Phe Val Gly Ser
        35                  40                  45

Ile Lys Thr Val Ile Gly His Thr Glu Gly Ser Ala Gly Leu Ala Ser
    50                  55                  60

Leu Ile Gly Ser Ser Leu Ala Met Lys His Gly Val Ile
65                  70                  75
```

<210> SEQ ID NO 41
<211> LENGTH: 43
<212> TYPE: PRT
<213> ORGANISM: Penicillium coprobium PF1169

<400> SEQUENCE: 41

```
Lys Leu Ala Phe Val Phe Thr Gly Gln Gly Gly Gln Trp Ala Gly Met
1               5                   10                  15

Gly Arg Glu Leu Leu Ser Ile Ser Thr Phe Arg Glu Ser Met Ala Arg
            20                  25                  30

Ser Gln Glu Ile Leu Ala Ser Leu Gly Cys Pro
        35                  40
```

<210> SEQ ID NO 42
<211> LENGTH: 71

```
<212> TYPE: PRT
<213> ORGANISM: Penicillium coprobium PF1169

<400> SEQUENCE: 42

Lys Ser Phe Leu Asp Asp Leu Ala Phe Thr Val Asn Glu Arg Arg Ser
1               5                   10                  15

Ile Phe Pro Trp Lys Ala Ala Val Val Gly Asp Thr Met Glu Gly Leu
            20                  25                  30

Ala Ala Ser Leu Ala Gln Asn Ile Lys Pro Arg Ser Val Leu Arg Met
        35                  40                  45

Pro Thr Leu Gly Phe Val Phe Thr Gly Gln Gly Ala Gln Trp Pro Gly
    50                  55                  60

Met Gly Lys Glu Leu Leu Gln
65                  70


<210> SEQ ID NO 43
<211> LENGTH: 55
<212> TYPE: PRT
<213> ORGANISM: Penicillium coprobium PF1169

<400> SEQUENCE: 43

Ser Val Ala Cys Ile Asn Ser Pro Phe Asn Cys Thr Leu Ser Gly Pro
1               5                   10                  15

Glu Glu Asp Ile Asp Ala Val Lys Ala Gln Ala Asp Gln Asp Gly Leu
            20                  25                  30

Phe Ala Gln Lys Leu Lys Thr Gly Val Ala Tyr His Ser Thr Ala Met
        35                  40                  45

Ser Ala Ile Ala Asn Asp Tyr
    50                  55


<210> SEQ ID NO 44
<211> LENGTH: 68
<212> TYPE: PRT
<213> ORGANISM: Penicillium coprobium PF1169

<400> SEQUENCE: 44

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly Asp Leu Asp Val Ile Ala Asn Leu Gln Thr
        35                  40                  45

Ala Leu Asp Lys Glu Gly Ile Phe Thr Arg Lys Leu Lys Val Asp Val
    50                  55                  60

Ala Tyr His Ser
65


<210> SEQ ID NO 45
<211> LENGTH: 38
<212> TYPE: PRT
<213> ORGANISM: Penicillium coprobium PF1169

<400> SEQUENCE: 45

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35
```

```
<210> SEQ ID NO 46
<211> LENGTH: 77
<212> TYPE: PRT
<213> ORGANISM: Penicillium coprobium PF1169

<400> SEQUENCE: 46

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly Ile
65                  70                  75


<210> SEQ ID NO 47
<211> LENGTH: 61
<212> TYPE: PRT
<213> ORGANISM: Penicillium coprobium PF1169

<400> SEQUENCE: 47

Ile Gly Ser Ile Lys Pro Asn Ile Gly His Leu Glu Ala Gly Ala Gly
1               5                   10                  15

Val Met Gly Phe Ile Lys Ala Ile Leu Ser Ile Gln Lys Gly Val Leu
            20                  25                  30

Ala Pro Gln Ala Asn Leu Thr Lys Leu Asn Ser Arg Ile Asp Trp Lys
        35                  40                  45

Thr Ala Gly Val Lys Val Val Gln Glu Ala Thr Pro Trp
    50                  55                  60


<210> SEQ ID NO 48
<211> LENGTH: 37
<212> TYPE: PRT
<213> ORGANISM: Penicillium coprobium PF1169

<400> SEQUENCE: 48

Gly Leu Phe Asp Ala Pro Phe Phe Asn Ile Thr Leu Gln Glu Ala Gln
1               5                   10                  15

Thr Met Asp Pro Gln Gln Arg Ile Phe Leu Glu Cys Val Tyr Glu Ala
            20                  25                  30

Leu Glu Asn Gly Gly
        35


<210> SEQ ID NO 49
<211> LENGTH: 70
<212> TYPE: PRT
<213> ORGANISM: Penicillium coprobium PF1169

<400> SEQUENCE: 49

Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
```

```
    50                  55                  60

Pro Asn Gly Ala Ala Gln
65                  70


<210> SEQ ID NO 50
<211> LENGTH: 37
<212> TYPE: PRT
<213> ORGANISM: Penicillium coprobium PF1169

<400> SEQUENCE: 50

Ser Phe Asp Ser Arg Ala Glu Gly Tyr Ala Arg Gly Glu Gly Val Gly
1               5                   10                  15

Thr Val Val Val Lys Pro Leu Ser Thr Ala Ile Arg Asp Gly Asp Thr
            20                  25                  30

Ile Arg Ala Val Ile
        35


<210> SEQ ID NO 51
<211> LENGTH: 83
<212> TYPE: PRT
<213> ORGANISM: Penicillium coprobium PF1169

<400> SEQUENCE: 51

Trp Pro Arg Leu Pro Glu Arg Arg Arg Ile Ala Val Val Asn Asn Phe
1               5                   10                  15

Ser Ala Ala Gly Gly Asn Thr Thr Val Ala Leu Glu Asp Ala Pro Ile
            20                  25                  30

Arg Thr Arg Ser Gly Ser Asp Pro Arg Ser Leu His Pro Ile Ala Ile
        35                  40                  45

Ser Ala Lys Ser Lys Val Ser Leu Arg Gly Asn Leu Glu Asn Leu Leu
    50                  55                  60

Ala Tyr Leu Asp Thr His Pro Asp Val Ser Leu Ser Asp Leu Ser Tyr
65                  70                  75                  80

Thr Thr Thr


<210> SEQ ID NO 52
<211> LENGTH: 59
<212> TYPE: PRT
<213> ORGANISM: Penicillium coprobium PF1169

<400> SEQUENCE: 52

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55


<210> SEQ ID NO 53
<211> LENGTH: 67
<212> TYPE: PRT
<213> ORGANISM: Penicillium coprobium PF1169

<400> SEQUENCE: 53

Leu Ser Pro Gln Asn Asn Pro Glu Asp Arg Cys Gln Tyr Phe Glu Ala
1               5                   10                  15

His Gly Thr Gly Thr Gln Ala Gly Asp Pro Gln Glu Ala Ala Ala Ile
```

-continued

```
            20                  25                  30

Asn Ser Ser Phe Phe Gly Pro Glu Ser Val Pro Asp Ser Thr Asp Arg
        35                  40                  45

Leu Tyr Val Gly Ser Ile Lys Thr Ile Ile Gly His Thr Glu Ala Thr
    50                  55                  60

Ala Gly Leu
65


<210> SEQ ID NO 54
<211> LENGTH: 83
<212> TYPE: PRT
<213> ORGANISM: Penicillium coprobium PF1169

<400> SEQUENCE: 54

Asp Gly Tyr Gly Arg Gly Glu Gly Val Ala Ser Val Val Leu Lys Arg
1               5                   10                  15

Leu Gln Asp Ala Ile Asn Asp Gly Asp Pro Ile Glu Cys Val Ile Arg
            20                  25                  30

Ala Ser Gly Ala Asn Ser Asp Gly Arg Thr Met Gly Ile Thr Met Pro
        35                  40                  45

Asn Pro Lys Ala Gln Gln Ser Leu Ile Leu Ala Thr Tyr Ala Arg Ala
    50                  55                  60

Gly Leu Ser Pro Gln Asn Asn Pro Glu Asp Arg Cys Gln Tyr Phe Glu
65                  70                  75                  80

Ala His Gly


<210> SEQ ID NO 55
<211> LENGTH: 38
<212> TYPE: PRT
<213> ORGANISM: Penicillium coprobium PF1169

<400> SEQUENCE: 55

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly
        35


<210> SEQ ID NO 56
<211> LENGTH: 29
<212> TYPE: PRT
<213> ORGANISM: Penicillium coprobium PF1169

<400> SEQUENCE: 56

Ser Gly Cys Tyr Arg Glu Leu Ala Asp Cys Pro Gly Gln Arg Gly Ile
1               5                   10                  15

Phe Thr Arg Lys Leu Lys Val Asp Val Ala Tyr His Ser
            20                  25


<210> SEQ ID NO 57
<211> LENGTH: 38
<212> TYPE: PRT
<213> ORGANISM: Penicillium coprobium PF1169

<400> SEQUENCE: 57

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
```

```
            20                  25                  30

Val Ala Leu His Leu Ala
        35


<210> SEQ ID NO 58
<211> LENGTH: 59
<212> TYPE: PRT
<213> ORGANISM: Penicillium coprobium PF1169

<400> SEQUENCE: 58

Ile Ser Glu Cys Val Thr Val Tyr Trp Lys Ala Ile Lys Ser Ala Gln
1               5                   10                  15

Pro Asp Gly Pro Tyr Ala Leu Ala Gly Tyr Ser Tyr Gly Ser Met Leu
            20                  25                  30

Ala Phe Glu Val Ala Lys Leu Leu Ile Lys Asn Gly Asp Lys Val Asp
        35                  40                  45

Phe Leu Gly Cys Phe Asn Leu Pro Pro His Ile
    50                  55


<210> SEQ ID NO 59
<211> LENGTH: 72
<212> TYPE: PRT
<213> ORGANISM: Penicillium coprobium PF1169

<400> SEQUENCE: 59

Gly Ala Ala Val Gln Leu Val Ile Glu Gly Gly Asn Gln Pro Lys Gly
1               5                   10                  15

Ala Met Met Ala Val Gly Ala Asn Ala Ser Thr Val Gln Pro Leu Leu
            20                  25                  30

Asp Ala Met Lys Asp Lys His Ala Val Val Ala Cys Ile Asn Ser Asp
        35                  40                  45

Ser Ser Ile Thr Val Ser Gly Asp Glu Thr Ala Ile Glu Asp Leu Glu
    50                  55                  60

Ser Val Leu Lys Arg Gln Asp Ile
65                  70


<210> SEQ ID NO 60
<211> LENGTH: 79
<212> TYPE: PRT
<213> ORGANISM: Penicillium coprobium PF1169

<400> SEQUENCE: 60

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Lys Val Gly Thr His
65                  70                  75


<210> SEQ ID NO 61
<211> LENGTH: 67
<212> TYPE: PRT
<213> ORGANISM: Penicillium coprobium PF1169

<400> SEQUENCE: 61
```

```
Phe Ile Glu Asp Ser Ile Ser Lys Glu His Lys Pro Thr Arg Val Pro
1               5                   10                  15

Ile His Gly Pro Tyr His Ala Ser His Leu Tyr Asn Asp Arg Asp Ile
            20                  25                  30

Asp Arg Ile Met Glu Ser Trp Pro Thr Glu Gln Leu Trp Ala Tyr Val
        35                  40                  45

Pro Gln Ile Pro Val Leu Ser Thr Gln Thr Gly Lys Ala Phe Gln Ala
    50                  55                  60

Asp Ser Leu
65


<210> SEQ ID NO 62
<211> LENGTH: 76
<212> TYPE: PRT
<213> ORGANISM: Penicillium coprobium PF1169

<400> SEQUENCE: 62

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75


<210> SEQ ID NO 63
<211> LENGTH: 31
<212> TYPE: PRT
<213> ORGANISM: Penicillium coprobium PF1169

<400> SEQUENCE: 63

Leu Phe Leu Phe Pro Asp Gly Ser Gly Ser Ala Thr Ser Tyr Ala Thr
1               5                   10                  15

Ile Pro Gly Ile Ser Pro Asp Val Cys Val Tyr Gly Leu Asn Cys
            20                  25                  30


<210> SEQ ID NO 64
<211> LENGTH: 26
<212> TYPE: PRT
<213> ORGANISM: Penicillium coprobium PF1169

<400> SEQUENCE: 64

Ala Lys His Pro Pro Ala Thr Ser Ile Leu Leu Gln Gly Asn Pro Lys
1               5                   10                  15

Thr Ala Thr Gln Ser Phe Ile Phe Val Pro
            20                  25


<210> SEQ ID NO 65
<211> LENGTH: 46
<212> TYPE: PRT
<213> ORGANISM: Penicillium coprobium PF1169

<400> SEQUENCE: 65

Tyr Gln Ala Thr Gly Cys Ala Ala Ser Leu Gln Ser Asn Arg Ile Ser
1               5                   10                  15

Tyr Phe Phe Asp Leu Arg Gly Pro Ser Ile Thr Ile Asp Thr Ala Cys
            20                  25                  30
```

```
Ser Ser Ser Leu Val Ala Leu His Tyr Ala Val Gln Ser Leu
        35                  40                  45


<210> SEQ ID NO 66
<211> LENGTH: 66
<212> TYPE: PRT
<213> ORGANISM: Penicillium coprobium PF1169

<400> SEQUENCE: 66

Tyr Ser Ala Thr Gly Ser Gly Leu Thr Val Leu Ala Asn Arg Ile Thr
1               5                   10                  15

His Cys Phe Asp Leu Arg Gly Pro Ser His Val Val Asp Thr Ala Cys
            20                  25                  30

Ser Ser Ser Leu Tyr Ala Leu His Ser Ala Cys Leu Ala Leu Asp Ser
        35                  40                  45

Arg Asp Cys Asp Gly Ala Val Val Ala Ala Ala Asn Leu Ile Gln Ser
    50                  55                  60

Pro Glu
65


<210> SEQ ID NO 67
<211> LENGTH: 76
<212> TYPE: PRT
<213> ORGANISM: Penicillium coprobium PF1169

<400> SEQUENCE: 67

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Lys Val
65                  70                  75


<210> SEQ ID NO 68
<211> LENGTH: 71
<212> TYPE: PRT
<213> ORGANISM: Penicillium coprobium PF1169

<400> SEQUENCE: 68

His Leu Asn Leu Met Gly Pro Ser Thr Ala Val Asp Ala Ala Cys Ala
1               5                   10                  15

Ser Ser Leu Val Ala Ile His His Gly Val Gln Ala Ile Lys Leu Gly
            20                  25                  30

Glu Ser Arg Val Ala Ile Val Gly Gly Val Asn Ala Leu Cys Gly Pro
        35                  40                  45

Gly Leu Thr Arg Val Leu Asp Lys Ala Gly Ser Ile Ser Ser Asp Gly
    50                  55                  60

Ser Cys Lys Ser Phe Asp Asp
65                  70


<210> SEQ ID NO 69
<211> LENGTH: 84
<212> TYPE: PRT
<213> ORGANISM: Penicillium coprobium PF1169
```

<400> SEQUENCE: 69

```
Ser Phe Arg Arg Gln Glu Asp Thr Trp Lys Val Leu Ser Asn Ala Thr
1               5                   10                  15

Ser Thr Leu Tyr Leu Ala Gly Ile Glu Ile Lys Trp Lys Glu Tyr His
            20                  25                  30

Gln Asp Phe Asn Ala Ala His Arg Val Leu Pro Leu Pro Ser Tyr Lys
        35                  40                  45

Trp Asp Leu Lys Asn Tyr Trp Ile Pro Tyr Thr Asn Asn Phe Cys Leu
    50                  55                  60

Leu Lys Gly Ala Pro Ala Ala Pro Val Ala Glu Ala Thr Pro Ile Ser
65                  70                  75                  80

Val Phe Leu Ser
```

<210> SEQ ID NO 70
<211> LENGTH: 78
<212> TYPE: PRT
<213> ORGANISM: Penicillium coprobium PF1169

<400> SEQUENCE: 70

```
Lys Thr Ser Cys Phe Val Gly Ser Phe Ser Ala Asp Tyr Thr Asp Leu
1               5                   10                  15

Leu Leu Arg Asp Pro Glu Cys Val Pro Met Tyr Gln Cys Thr Asn Ala
            20                  25                  30

Gly Gln Ser Arg Ala Met Thr Ala Asn Arg Leu Ser Tyr Phe Phe Asp
        35                  40                  45

Leu Lys Gly Pro Ser Val Thr Val Asp Thr Ala Cys Ser Gly Ser Leu
    50                  55                  60

Val Ala Leu His Leu Ala Cys Gln Ser Leu Arg Thr Gly Asp
65                  70                  75
```

<210> SEQ ID NO 71
<211> LENGTH: 67
<212> TYPE: PRT
<213> ORGANISM: Penicillium coprobium PF1169

<400> SEQUENCE: 71

```
Tyr Ser Ala Thr Gly Ser Gly Leu Thr Val Leu Ala Asn Arg Ile Thr
1               5                   10                  15

His Cys Phe Asp Leu Arg Gly Pro Ser His Val Val Asp Thr Ala Cys
            20                  25                  30

Ser Ser Ser Leu Tyr Ala Leu His Ser Ala Cys Phe Gly Pro Leu Asn
        35                  40                  45

Ser Arg Asp Cys Asp Gly Ala Val Val Ala Ala Ala Asn Leu Ile Gln
    50                  55                  60

Ser Pro Glu
65
```

<210> SEQ ID NO 72
<211> LENGTH: 79
<212> TYPE: PRT
<213> ORGANISM: Penicillium coprobium PF1169

<400> SEQUENCE: 72

```
Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30
```

```
Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75


<210> SEQ ID NO 73
<211> LENGTH: 40
<212> TYPE: PRT
<213> ORGANISM: Penicillium coprobium PF1169

<400> SEQUENCE: 73

Glu Ala Asn Leu His Val Pro Leu Glu Pro Thr Pro Trp Pro Ala Gly
1               5                   10                  15

Arg Pro Glu Arg Ile Ser Val Asn Ser Phe Gly Ile Gly Gly Ser Asn
            20                  25                  30

Ala His Ala Ile Leu Glu Ser Ala
        35                  40


<210> SEQ ID NO 74
<211> LENGTH: 70
<212> TYPE: PRT
<213> ORGANISM: Penicillium coprobium PF1169
<220> FEATURE:
<221> NAME/KEY: misc_feature
<222> LOCATION: (5)..(5)
<223> OTHER INFORMATION: Xaa can be any naturally occurring amino acid

<400> SEQUENCE: 74

Ile Gly His Thr Xaa Gly Ser Ala Gly Leu Ala Ser Leu Ile Gly Ser
1               5                   10                  15

Ser Leu Ala Met Lys His Gly Val Ile Pro Pro Asn Leu His Phe Gly
            20                  25                  30

Gln Leu Ser Glu Lys Val Ala Pro Phe Tyr Thr His Leu Asn Ile Pro
        35                  40                  45

Thr Glu Pro Val Pro Trp Pro Asn Ser Thr Ser Ser Gln Val Lys Arg
    50                  55                  60

Ala Ser Ile Asn Ser Phe
65                  70


<210> SEQ ID NO 75
<211> LENGTH: 45
<212> TYPE: PRT
<213> ORGANISM: Penicillium coprobium PF1169

<400> SEQUENCE: 75

Pro Val Cys Ser Gly Met Val Lys Ala Thr Phe Gly Pro Gln Ala Thr
1               5                   10                  15

Thr Val Ala Ser Phe Arg Arg Gln Glu Asp Thr Trp Lys Val Leu Ser
            20                  25                  30

Asn Ala Thr Ser Thr Leu Tyr Leu Ala Gly Ile Glu Ile
        35                  40                  45


<210> SEQ ID NO 76
<211> LENGTH: 19
<212> TYPE: PRT
<213> ORGANISM: Penicillium coprobium PF1169
<220> FEATURE:
<221> NAME/KEY: misc_feature
<222> LOCATION: (13)..(13)
<223> OTHER INFORMATION: Xaa can be any naturally occurring amino acid
```

<400> SEQUENCE: 76

```
Leu Leu Gly Leu Arg Leu Lys Trp Lys Glu Tyr His Xaa Asp Phe Asn
1               5                   10                  15

Ala Ala His
```

<210> SEQ ID NO 77
<211> LENGTH: 69
<212> TYPE: PRT
<213> ORGANISM: Penicillium coprobium PF1169

<400> SEQUENCE: 77

```
Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu Thr Ala Val His Leu
    50                  55                  60

Ala Ala Gln Ser Leu
65
```

<210> SEQ ID NO 78
<211> LENGTH: 85
<212> TYPE: PRT
<213> ORGANISM: Penicillium coprobium PF1169

<400> SEQUENCE: 78

```
Asp Ala Gln Phe Phe Gly Thr Lys Pro Val Glu Ala Asn Ser Ile Asp
1               5                   10                  15

Pro Gln Gln Arg Leu Leu Leu Glu Thr Val Tyr Glu Gly Leu Glu Thr
            20                  25                  30

Ser Gly Ile Pro Met Glu Arg Leu Gln Gly Ser Asn Thr Ala Val Tyr
        35                  40                  45

Val Gly Leu Met Thr Asn Asp Tyr Ala Asp Met Leu Gly Arg Asp Met
    50                  55                  60

Gln Asn Phe Pro Thr Tyr Phe Ala Ser Gly Thr Ala Arg Ser Ile Leu
65                  70                  75                  80

Ser Asn Arg Val Ser
                85
```

<210> SEQ ID NO 79
<211> LENGTH: 28
<212> TYPE: PRT
<213> ORGANISM: Penicillium coprobium PF1169

<400> SEQUENCE: 79

```
Asp Pro Ala Tyr Phe Asp Ser Ser Phe Phe Asn Ile Thr Lys Thr Glu
1               5                   10                  15

Leu Leu Thr Leu Asp Pro Gln Gln Arg Leu Val Leu
            20                  25
```

<210> SEQ ID NO 80
<211> LENGTH: 51
<212> TYPE: PRT
<213> ORGANISM: Penicillium coprobium PF1169

<400> SEQUENCE: 80

```
Val Ala Cys Val Asn Ser Pro Ala Ser Thr Thr Leu Ser Gly Asp Val
1               5                   10                  15

Asp Tyr Ile Asn Gln Leu Glu Ala Arg Leu Gln Gln Asp Gly His Phe
            20                  25                  30

Ala Arg Lys Leu Arg Ile Asp Thr Ala Tyr His Ser Pro His Met Glu
        35                  40                  45

Glu Leu Val
    50


<210> SEQ ID NO 81
<211> LENGTH: 24
<212> TYPE: PRT
<213> ORGANISM: Penicillium coprobium PF1169

<400> SEQUENCE: 81

Leu Lys Ser Ile Ser Pro Val Val Thr Gln Leu Gly Thr Thr Cys Val
1               5                   10                  15

Gln Met Ala Leu Thr Lys Tyr Trp
            20


<210> SEQ ID NO 82
<211> LENGTH: 59
<212> TYPE: PRT
<213> ORGANISM: Penicillium coprobium PF1169

<400> SEQUENCE: 82

Gly Cys Phe Tyr Gly Met Thr Ser Asp Asp Tyr Arg Glu Val Asn Ser
1               5                   10                  15

Gly Gln Asp Ile Asp Thr Tyr Phe Ile Pro Gly Gly Asn Arg Ala Phe
            20                  25                  30

Thr Pro Gly Arg Ile Asn Tyr Tyr Phe Lys Phe Ser Gly Pro Ser Val
        35                  40                  45

Ser Val Asp Thr Ala Cys Ser Ser Ser Leu Ala
    50                  55


<210> SEQ ID NO 83
<211> LENGTH: 16
<212> TYPE: PRT
<213> ORGANISM: Penicillium coprobium PF1169

<400> SEQUENCE: 83

Leu Glu Met Ala Gly Phe Ile Pro Asp Ser Ile Pro Leu Arg Arg Arg
1               5                   10                  15


<210> SEQ ID NO 84
<211> LENGTH: 53
<212> TYPE: PRT
<213> ORGANISM: Penicillium coprobium PF1169

<400> SEQUENCE: 84

Ala Ile Val Gly Gly Val Asn Ala Leu Cys Gly Pro Gly Leu Thr Arg
1               5                   10                  15

Val Leu Asp Lys Ala Gly Ala Ile Ser Ser Asp Gly Ser Cys Lys Ser
            20                  25                  30

Phe Asp Asp Asp Ala His Gly Tyr Ala Arg Gly Glu Gly Ala Gly Ala
        35                  40                  45

Leu Val Thr Lys Lys
    50


<210> SEQ ID NO 85
```

<211> LENGTH: 60
<212> TYPE: PRT
<213> ORGANISM: Penicillium coprobium PF1169

<400> SEQUENCE: 85

```
Ile Ala Ile Val Gly Ile Gly Gly Arg Phe Pro Gly Glu Ala Thr Asn
1               5                   10                  15

Pro Asn Arg Leu Trp Asp Met Val Ser Asn Gly Arg Ser Ala Leu Thr
            20                  25                  30

Glu Val Pro Lys Asp Arg Phe Asn Ile Asp Ala Phe Tyr His Pro His
        35                  40                  45

Ala Glu Arg Gln Gly Thr Met Asn Val Arg Arg Gly
    50                  55                  60
```

<210> SEQ ID NO 86
<211> LENGTH: 53
<212> TYPE: PRT
<213> ORGANISM: Penicillium coprobium PF1169

<400> SEQUENCE: 86

```
Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val
    50
```

<210> SEQ ID NO 87
<211> LENGTH: 18
<212> TYPE: PRT
<213> ORGANISM: Penicillium coprobium PF1169

<400> SEQUENCE: 87

```
Ser Val Pro Ile Glu Glu His Ser Pro Val Val Thr Gln Leu Gly Thr
1               5                   10                  15

Thr Cys
```

<210> SEQ ID NO 88
<211> LENGTH: 62
<212> TYPE: PRT
<213> ORGANISM: Penicillium coprobium PF1169

<400> SEQUENCE: 88

```
Phe Leu Asp Asp Leu Ala Phe Thr Val Asn Glu Arg Arg Ser Ile Phe
1               5                   10                  15

Pro Trp Lys Ala Ala Val Val Gly Asp Thr Met Glu Gly Leu Ala Ala
            20                  25                  30

Ser Leu Ala Gln Asn Ile Lys Pro Arg Ser Val Leu Arg Met Pro Thr
        35                  40                  45

Leu Gly Phe Val Phe Thr Gly Gln Gly Ala Gln Trp Pro Gly
    50                  55                  60
```

<210> SEQ ID NO 89
<211> LENGTH: 51
<212> TYPE: PRT
<213> ORGANISM: Penicillium coprobium PF1169

<400> SEQUENCE: 89

```
Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
            20                  25                  30

Glu Phe Leu Glu Ala Ala Asn Gly His Arg Met Asn Asp Cys Gly Val
        35                  40                  45

Val Thr Ser
    50


<210> SEQ ID NO 90
<211> LENGTH: 77
<212> TYPE: PRT
<213> ORGANISM: Penicillium coprobium PF1169

<400> SEQUENCE: 90

Glu Cys Gly Phe Val Glu Met His Gly Thr Gly Thr Lys Ala Gly Asp
1               5                   10                  15

Pro Val Glu Ala Ala Ala Val His Ala Ala Leu Gly Lys Asn Arg Thr
            20                  25                  30

Leu Arg Asn Pro Leu Tyr Ile Gly Ser Val Lys Ser Asn Ile Gly His
        35                  40                  45

Leu Glu Gly Ala Ser Gly Ile Val Ala Val Ile Lys Ala Ala Met Met
    50                  55                  60

Leu Asp Arg Asp Leu Met Leu Pro Asn Ala Glu Phe Lys
65                  70                  75


<210> SEQ ID NO 91
<211> LENGTH: 78
<212> TYPE: PRT
<213> ORGANISM: Penicillium coprobium PF1169
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

Phe Phe Lys Xaa Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met Asn Ile Leu Thr Asn Ser
    50                  55                  60

Asp Ala Phe Ala Gly Leu Ser His Gly His Phe Leu Thr Lys
65                  70                  75


<210> SEQ ID NO 92
<211> LENGTH: 79
<212> TYPE: PRT
<213> ORGANISM: Penicillium coprobium PF1169

<400> SEQUENCE: 92

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45
```

```
Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75


<210> SEQ ID NO 93
<211> LENGTH: 68
<212> TYPE: PRT
<213> ORGANISM: Penicillium coprobium PF1169

<400> SEQUENCE: 93

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Asp Gly Arg Thr Ala Gly Ile Thr Val Pro Asn Gly
    50                  55                  60

Ala Ala Gln Glu
65


<210> SEQ ID NO 94
<211> LENGTH: 80
<212> TYPE: PRT
<213> ORGANISM: Penicillium coprobium PF1169

<400> SEQUENCE: 94

Ser Pro Leu Phe Gly Leu Ala Arg Ile Ile Ala Ser Glu His Pro Asp
1               5                   10                  15

Leu Gly Ser Leu Ile Asp Ile Glu Glu Pro Ile Ile Pro Leu Ser Thr
            20                  25                  30

Met Arg Tyr Ile Gln Gly Ala Asp Ile Val Arg Ile Ser Asp Gly Ile
        35                  40                  45

Ala Arg Thr Ser Arg Phe Arg Ser Leu Pro Arg Thr Lys Leu Arg Pro
    50                  55                  60

Val Ser Asp Gly Pro Arg Leu Leu Pro Arg Pro Glu Gly Thr Tyr Leu
65                  70                  75                  80


<210> SEQ ID NO 95
<211> LENGTH: 75
<212> TYPE: PRT
<213> ORGANISM: Penicillium coprobium PF1169

<400> SEQUENCE: 95

Asn Arg Ile Ser Tyr Tyr Phe Asp Trp Gln Gly Pro Ser Met Ala Val
1               5                   10                  15

Asp Thr Gly Cys Ser Ser Ser Leu Leu Ala Val His Leu Gly Val Glu
            20                  25                  30

Ala Leu Gln Asn Asp Asp Cys Ser Met Ala Val Ala Val Gly Ser Asn
        35                  40                  45

Leu Ile Leu Ser Pro Asn Ala Tyr Ile Ala Asp Ser Lys Thr Arg Met
    50                  55                  60

Leu Ser Pro Thr Gly Arg Ser Arg Met Trp Asp
65                  70                  75


<210> SEQ ID NO 96
<211> LENGTH: 81
<212> TYPE: PRT
```

<213> ORGANISM: Penicillium coprobium PF1169

<400> SEQUENCE: 96

```
Val Asp Val Asn Pro Ala Val Leu Lys Asp Ala Pro Leu Pro Trp Asp
1               5                   10                  15

Pro Ser Ser Trp Ala Pro Ile Leu Asp Ala Ala Thr Ser Val Gly Ser
            20                  25                  30

Thr Ile Phe Gln Thr Ala Ala Leu Arg Met Pro Ala Gln Ile Glu Arg
        35                  40                  45

Val Glu Ile Phe Thr Ser Glu Asn Pro Pro Lys Thr Ser Trp Leu Tyr
    50                  55                  60

Val Gln Glu Ala Ser Asp Ala Val Pro Thr Ser His Val Ser Val Val
65                  70                  75                  80

Ser
```

<210> SEQ ID NO 97
<211> LENGTH: 37
<212> TYPE: PRT
<213> ORGANISM: Penicillium coprobium PF1169

<400> SEQUENCE: 97

```
Pro Leu Phe Gly Leu Ala Arg Ile Ile Ala Ser Glu His Pro Asp Leu
1               5                   10                  15

Gly Ser Leu Ile Asp Ile Glu Glu Pro Ile Ile Pro Leu Ser Thr Met
            20                  25                  30

Arg Tyr Ile Arg Gly
        35
```

<210> SEQ ID NO 98
<211> LENGTH: 84
<212> TYPE: PRT
<213> ORGANISM: Penicillium coprobium PF1169

<400> SEQUENCE: 98

```
Ala Val Ile Arg Gly Thr Gly Ser Asn Gln Asp Gly Arg Thr Ala Gly
1               5                   10                  15

Ile Thr Val Pro Asn Gly Ala Ala Gln Glu Ser Leu Ile Arg Ser Val
            20                  25                  30

Tyr Ala Gln Ala Asp Leu Asp Pro Ser Glu Thr Asp Phe Val Glu Ala
        35                  40                  45

His Gly Thr Gly Thr Leu Ala Gly Asp Pro Val Glu Thr Gly Ala Ile
    50                  55                  60

Ala Arg Val Phe Gly Thr Asp Arg Pro Pro Gly Asp Pro Val Arg Ile
65                  70                  75                  80

Gly Ser Ile Lys
```

<210> SEQ ID NO 99
<211> LENGTH: 69
<212> TYPE: PRT
<213> ORGANISM: Penicillium coprobium PF1169

<400> SEQUENCE: 99

```
Leu Glu Val Val Trp Glu Cys Leu Glu Asn Ser Gly Glu Thr Gln Trp
1               5                   10                  15

Arg Gly Lys Glu Ile Gly Cys Phe Val Gly Val Phe Gly Glu Asp Trp
            20                  25                  30

Leu Glu Met Ser His Lys Asp Pro Gln His Leu Asn Gln Met Phe Pro
        35                  40                  45
```

```
Ile Ala Thr Gly Gly Phe Ala Leu Ala Asn Gln Val Ser Tyr Arg Phe
    50                  55                  60

Asp Leu Thr Gly Pro
65


<210> SEQ ID NO 100
<211> LENGTH: 79
<212> TYPE: PRT
<213> ORGANISM: Penicillium coprobium PF1169

<400> SEQUENCE: 100

Gly Gly Ala Thr Asp Thr Glu Lys Phe Trp Asp Leu Leu Ala Ser Gly
1               5                   10                  15

Val Asp Val His Arg Lys Ile Pro Ala Asp Arg Phe Asp Val Glu Thr
            20                  25                  30

His Tyr Asp Pro Asn Gly Lys Arg Met Asn Ala Ser His Thr Pro Tyr
        35                  40                  45

Gly Cys Phe Ile Asp Glu Pro Gly Leu Phe Asp Ala Ala Phe Phe Asn
    50                  55                  60

Met Ser Pro Arg Glu Ala Gln Gln Thr Asp Pro Met Gln Arg Leu
65                  70                  75


<210> SEQ ID NO 101
<211> LENGTH: 52
<212> TYPE: PRT
<213> ORGANISM: Penicillium coprobium PF1169

<400> SEQUENCE: 101

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50


<210> SEQ ID NO 102
<211> LENGTH: 34
<212> TYPE: PRT
<213> ORGANISM: Penicillium coprobium PF1169

<400> SEQUENCE: 102

Val Gly Phe Val Phe Thr Gly Gln Gly Ala Gln Trp His Gly Met Gly
1               5                   10                  15

Lys Glu Leu Leu Ser Thr Tyr Pro Ile Phe Arg Gln Thr Met Gln Asp
            20                  25                  30

Val Asp


<210> SEQ ID NO 103
<211> LENGTH: 63
<212> TYPE: PRT
<213> ORGANISM: Penicillium coprobium PF1169

<400> SEQUENCE: 103

Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30
```

Arg Ala Gly Tyr Val Ala Asn Arg Thr Ala Ala Thr Asn Leu His Arg
35 40 45

Ile Gly Thr Phe Tyr Gly Gln Ala Ser Asp Asp Tyr Arg Glu Val
50 55 60

<210> SEQ ID NO 104
<211> LENGTH: 43
<212> TYPE: PRT
<213> ORGANISM: Penicillium coprobium PF1169

<400> SEQUENCE: 104

Ala Val Val Ser Gly Val Ser Ile Leu Glu Asn Pro Val Glu Thr Ile
1 5 10 15

Gly Met Ser His His Gly Leu Leu Gly Pro Gln Gly Arg Ser Phe Ser
20 25 30

Phe Asp Ser Arg Ala Glu Gly Tyr Ala Arg Gly
35 40

<210> SEQ ID NO 105
<211> LENGTH: 71
<212> TYPE: PRT
<213> ORGANISM: Penicillium coprobium PF1169

<400> SEQUENCE: 105

Lys Ala Ser Leu Ser Leu Gln His Gly Met Ile Ala Pro Asn Leu Leu
1 5 10 15

Met Gln His Leu Asn Pro Lys Ile Lys Pro Phe Ala Ala Lys Leu Ser
20 25 30

Val Pro Thr Glu Cys Ile Pro Trp Pro Ala Val Pro Asp Gly Cys Pro
35 40 45

Arg Arg Ala Ser Val Asn Ser Phe Gly Phe Gly Gly Ala Asn Val His
50 55 60

Val Val Leu Glu Ser Tyr Thr
65 70

<210> SEQ ID NO 106
<211> LENGTH: 28
<212> TYPE: PRT
<213> ORGANISM: Penicillium coprobium PF1169

<400> SEQUENCE: 106

Pro Trp Pro Thr Thr Gly Leu Arg Arg Ala Ser Val Asn Ser Phe Gly
1 5 10 15

Tyr Gly Gly Thr Asn Ala His Cys Val Leu Asp Asp
20 25

<210> SEQ ID NO 107
<211> LENGTH: 71
<212> TYPE: PRT
<213> ORGANISM: Penicillium coprobium PF1169

<400> SEQUENCE: 107

Lys Ala Ser Leu Ser Leu Gln His Gly Met Ile Ala Pro Asn Leu Leu
1 5 10 15

Met Gln His Leu Asn Pro Lys Ile Lys Pro Phe Ala Ala Lys Leu Ser
20 25 30

Val Pro Thr Glu Cys Ile Pro Trp Pro Ala Val Pro Asp Gly Cys Pro
35 40 45

Arg Arg Ala Ser Val Asn Ser Phe Gly Phe Gly Gly Ala Asn Val His

```
    50                  55                  60

Val Val Leu Glu Ser Tyr Thr
65                  70


<210> SEQ ID NO 108
<211> LENGTH: 50
<212> TYPE: PRT
<213> ORGANISM: Penicillium coprobium PF1169

<400> SEQUENCE: 108

Asp Arg Leu Phe Leu Gln Met Ser His Glu Glu Trp Glu Ala Ala Leu
1               5                   10                  15

Ala Pro Lys Val Thr Gly Thr Trp Asn Leu His His Ala Thr Ala Gln
            20                  25                  30

His Ser Leu Asp Phe Phe Val Val Phe Gly Ser Ile Ala Gly Val Cys
        35                  40                  45

Gly Asn
    50


<210> SEQ ID NO 109
<211> LENGTH: 82
<212> TYPE: PRT
<213> ORGANISM: Penicillium coprobium PF1169

<400> SEQUENCE: 109

Thr Phe Leu Lys Gly Thr Gly Gly Gln Met Leu Gln Asn Val Val Leu
1               5                   10                  15

Arg Val Pro Val Ala Ile Asn Ala Pro Arg Ser Val Gln Val Val Val
            20                  25                  30

Gln Gln Asp Gln Val Lys Val Val Ser Arg Leu Ile Pro Ser Glu Ala
        35                  40                  45

Ser Val Leu Asp Asp Asp Ala Ser Trp Val Thr His Thr Thr Ala Tyr
    50                  55                  60

Trp Asp Arg Arg Val Leu Gly Ser Glu Asp Arg Ile Asp Leu Ala Ala
65                  70                  75                  80

Val Lys


<210> SEQ ID NO 110
<211> LENGTH: 30
<212> TYPE: PRT
<213> ORGANISM: Penicillium coprobium PF1169

<400> SEQUENCE: 110

Asp Thr Ala Cys Ser Ser Ser Leu Val Ala Leu His Tyr Ala Val Gln
1               5                   10                  15

Ser Leu Arg Asn Gly Glu Ser Thr Glu Ala Leu Ile Ala Gly
            20                  25                  30


<210> SEQ ID NO 111
<211> LENGTH: 38
<212> TYPE: PRT
<213> ORGANISM: Penicillium coprobium PF1169

<400> SEQUENCE: 111

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
            20                  25                  30

Ser Leu Val Ala Leu His
```

35

<210> SEQ ID NO 112
<211> LENGTH: 72
<212> TYPE: PRT
<213> ORGANISM: Penicillium coprobium PF1169

<400> SEQUENCE: 112

Thr Ser Thr Gln Leu Asn Asp Leu Asn Glu Thr Asn Ala Ile Lys Lys
1 5 10 15

Val Phe Gly Lys Gln Ala Tyr Asn Ile Pro Ile Ser Ser Thr Lys Ser
20 25 30

Tyr Thr Gly His Leu Ile Gly Ala Ala Gly Thr Met Glu Thr Ile Phe
35 40 45

Cys Ile Lys Thr Met Gln Glu Lys Ile Ala Pro Ala Thr Thr Asn Leu
50 55 60

Lys Glu Arg Asp Ser Asn Cys Asp
65 70

<210> SEQ ID NO 113
<211> LENGTH: 50
<212> TYPE: PRT
<213> ORGANISM: Penicillium coprobium PF1169

<400> SEQUENCE: 113

Val Ile Val Gly Ser Ala Ala Asn Gln Asn Leu Asn Leu Ser His Ile
1 5 10 15

Thr Val Pro His Ser Gly Ser Gln Val Lys Leu Tyr Gln Asn Val Met
20 25 30

Ser Gln Ala Gly Val His Pro His Ser Val Thr Tyr Val Glu Ala His
35 40 45

Gly Thr
50

<210> SEQ ID NO 114
<211> LENGTH: 48
<212> TYPE: PRT
<213> ORGANISM: Penicillium coprobium PF1169

<400> SEQUENCE: 114

Leu Pro Thr Ala Ile Gln Pro Leu Phe Arg Ala Asn Val Ser Tyr Leu
1 5 10 15

Leu Val Gly Gly Leu Gly Gly Ile Gly Lys Glu Val Ala Leu Trp Met
20 25 30

Val Gln Asn Gly Ala Lys Ser Leu Ile Phe Val Asn Arg Ser Gly Leu
35 40 45

<210> SEQ ID NO 115
<211> LENGTH: 53
<212> TYPE: PRT
<213> ORGANISM: Penicillium coprobium PF1169

<400> SEQUENCE: 115

Val Ala Ile Val Gly Gly Val Asn Ala Leu Cys Gly Pro Gly Leu Thr
1 5 10 15

Arg Val Leu Asp Lys Ala Gly Ala Ile Ser Ser Asp Gly Ser Cys Lys
20 25 30

Ser Phe Asp Asp Asp Ala His Gly Tyr Ala Arg Gly Glu Gly Ala Gly
35 40 45

```
Ala Leu Val Leu Lys
    50


<210> SEQ ID NO 116
<211> LENGTH: 28
<212> TYPE: PRT
<213> ORGANISM: Penicillium coprobium PF1169

<400> SEQUENCE: 116

Pro Trp Glu Ser Pro Gly Ala Arg Arg Val Ser Val Asn Ser Phe Gly
1               5                   10                  15

Tyr Gly Gly Ser Asn Ala His Val Ile Ile Glu Asp
            20                  25


<210> SEQ ID NO 117
<211> LENGTH: 72
<212> TYPE: PRT
<213> ORGANISM: Penicillium coprobium PF1169

<400> SEQUENCE: 117

Lys Thr Leu Arg Glu Trp Met Thr Ala Glu Gly Lys Asp His Asn Leu
1               5                   10                  15

Ser Asp Ile Leu Thr Thr Leu Ala Thr Arg Arg Asp His His Asp Tyr
            20                  25                  30

Arg Ala Ala Leu Val Val Asp Asp Asn Arg Asp Ala Glu Leu Ala Leu
        35                  40                  45

Gln Ala Leu Glu His Gly Val Asp Gln Thr Phe Thr Thr Gln Ser Arg
    50                  55                  60

Val Phe Gly Ala Asp Ile Ser Lys
65                  70


<210> SEQ ID NO 118
<211> LENGTH: 80
<212> TYPE: PRT
<213> ORGANISM: Penicillium coprobium PF1169

<400> SEQUENCE: 118

Ser Asp Asp Tyr Arg Glu Val Asn Ser Gly Gln Asp Ile Asp Thr Tyr
1               5                   10                  15

Phe Ile Pro Gly Gly Asn Arg Ala Phe Thr Pro Gly Arg Ile Asn Tyr
            20                  25                  30

Tyr Phe Lys Phe Ser Gly Pro Ser Val Ser Val Asp Thr Ala Cys Ser
        35                  40                  45

Ser Ser Leu Ala Ala Ile His Val Ala Cys Asn Ser Leu Trp Arg Asn
    50                  55                  60

Glu Ser Asp Ser Ala Val Ala Gly Gly Val Asn Ile Leu Thr Asn Pro
65                  70                  75                  80


<210> SEQ ID NO 119
<211> LENGTH: 56
<212> TYPE: PRT
<213> ORGANISM: Penicillium coprobium PF1169

<400> SEQUENCE: 119

Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45
```

```
Gly Ser Asn Gln Gly Arg Ala Asn
    50                  55


<210> SEQ ID NO 120
<211> LENGTH: 63
<212> TYPE: PRT
<213> ORGANISM: Penicillium coprobium PF1169

<400> SEQUENCE: 120

Asp Thr Ala Cys Ser Ser Ser Leu Tyr Ala Leu His Ser Ala Cys Leu
1               5                   10                  15

Ala Leu Asp Ser Arg Asp Cys Asp Gly Ala Val Val Ala Ala Ala Asn
            20                  25                  30

Leu Ile Gln Ser Pro Glu Gln Gln Met Ile Ala Val Lys Ala Gly Ile
        35                  40                  45

Leu Ser Pro Asp Ser Met Cys His Thr Phe Asp Glu Ser Ala Asn
    50                  55                  60


<210> SEQ ID NO 121
<211> LENGTH: 28
<212> TYPE: PRT
<213> ORGANISM: Penicillium coprobium PF1169

<400> SEQUENCE: 121

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp
            20                  25


<210> SEQ ID NO 122
<211> LENGTH: 62
<212> TYPE: PRT
<213> ORGANISM: Penicillium coprobium PF1169

<400> SEQUENCE: 122

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Leu Ile Lys Gly Pro
    50                  55                  60


<210> SEQ ID NO 123
<211> LENGTH: 80
<212> TYPE: PRT
<213> ORGANISM: Penicillium coprobium PF1169

<400> SEQUENCE: 123

Arg Trp Glu Pro Tyr Tyr Arg Arg Asp Pro Arg Asn Glu Lys Phe Leu
1               5                   10                  15

Lys Gln Thr Thr Ser Arg Gly Tyr Phe Leu Asp His Leu Glu Asp Phe
            20                  25                  30

Asp Cys Gln Phe Phe Gly Ile Ser Pro Lys Glu Ala Glu Gln Met Asp
        35                  40                  45

Pro Gln Gln Arg Val Ser Leu Glu Val Ala Ser Glu Ala Leu Glu Asp
    50                  55                  60

Ala Gly Ile Pro Ala Lys Ser Leu Ser Gly Ser Asp Thr Ala Val Phe
```

```
65                  70                  75                  80


<210> SEQ ID NO 124
<211> LENGTH: 28
<212> TYPE: PRT
<213> ORGANISM: Penicillium coprobium PF1169

<400> SEQUENCE: 124

Pro Gly Arg Ile Asn Tyr Phe Phe Lys Phe Ser Gly Pro Ser Phe Ser
1               5                   10                  15

Ile Asp Thr Ala Cys Ser Ser Ser Leu Ala Thr Ile
            20                  25


<210> SEQ ID NO 125
<211> LENGTH: 64
<212> TYPE: PRT
<213> ORGANISM: Penicillium coprobium PF1169

<400> SEQUENCE: 125

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro Ser
    50                  55                  60


<210> SEQ ID NO 126
<211> LENGTH: 52
<212> TYPE: PRT
<213> ORGANISM: Penicillium coprobium PF1169

<400> SEQUENCE: 126

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50


<210> SEQ ID NO 127
<211> LENGTH: 38
<212> TYPE: PRT
<213> ORGANISM: Penicillium coprobium PF1169

<400> SEQUENCE: 127

Gln Pro Leu Cys Thr Ala Ile Gln Ile Ala Leu Val Glu Leu Leu Glu
1               5                   10                  15

Ser Phe Gly Val Val Pro Lys Ala Val Val Gly His Ser Ser Gly Glu
            20                  25                  30

Ile Ala Ala Ala Tyr Val
        35


<210> SEQ ID NO 128
<211> LENGTH: 86
<212> TYPE: PRT
<213> ORGANISM: Penicillium coprobium PF1169
```

<400> SEQUENCE: 128

```
Arg Leu Pro Gly Asp Val Ser Thr Pro Glu Glu Phe Trp Asp Leu Cys
1               5                   10                  15

Ser Arg Gly Arg Gly Ala Trp Ser Pro Val Pro Lys Asp Arg Phe Asn
            20                  25                  30

Ala Gly Ser Phe Tyr His Pro Asn Ala Asp Arg Pro Gly Ser Phe Asn
        35                  40                  45

Ala Ala Gly Ala His Phe Leu Thr Glu Asp Ile Gly Leu Phe Asp Ala
    50                  55                  60

Pro Phe Phe Asn Ile Thr Leu Gln Glu Ala Gln Thr Met Asp Pro Gln
65                  70                  75                  80

Gln Arg Ile Phe Leu Glu
                85
```

<210> SEQ ID NO 129
<211> LENGTH: 69
<212> TYPE: PRT
<213> ORGANISM: Penicillium coprobium PF1169

<400> SEQUENCE: 129

```
Gln Phe Phe His Ala His Gly Thr Gly Thr Gln Ala Gly Asp Pro Gln
1               5                   10                  15

Glu Ala Glu Ala Val Ser Thr Ala Leu Phe Pro Asp Gly Ser Asn Ile
            20                  25                  30

Glu Thr Lys Leu Phe Val Gly Ser Ile Lys Thr Val Ile Gly His Thr
        35                  40                  45

Glu Gly Ser Ala Gly Leu Ala Ser Leu Ile Gly Ser Ser Leu Ala Met
    50                  55                  60

Lys His Gly Val Ile
65
```

<210> SEQ ID NO 130
<211> LENGTH: 64
<212> TYPE: PRT
<213> ORGANISM: Penicillium coprobium PF1169

<400> SEQUENCE: 130

```
Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro Ser
    50                  55                  60
```

<210> SEQ ID NO 131
<211> LENGTH: 67
<212> TYPE: PRT
<213> ORGANISM: Penicillium coprobium PF1169

<400> SEQUENCE: 131

```
Leu Asp Asp Leu Ala Phe Thr Val Asn Glu Arg Arg Ser Ile Phe Pro
1               5                   10                  15

Trp Lys Ala Ala Val Val Gly Asp Thr Met Glu Gly Leu Ala Ala Ser
            20                  25                  30

Leu Ala Gln Asn Ile Lys Pro Arg Ser Val Leu Arg Met Pro Thr Leu
        35                  40                  45
```

```
Gly Phe Val Phe Thr Gly Gln Gly Ala Gln Trp Pro Gly Met Gly Lys
    50                  55                  60

Glu Leu Leu
65


<210> SEQ ID NO 132
<211> LENGTH: 21
<212> TYPE: PRT
<213> ORGANISM: Penicillium coprobium PF1169

<400> SEQUENCE: 132

Ala His Gly Thr Gly Thr Lys Val Gly Asp Pro Met Glu Val Glu Ala
1               5                   10                  15

Ile Ala Asp Val Phe
            20


<210> SEQ ID NO 133
<211> LENGTH: 71
<212> TYPE: PRT
<213> ORGANISM: Penicillium coprobium PF1169

<400> SEQUENCE: 133

Lys Gly Gly Met Leu Ala Val Gly Ala Ser Ala Ser Asp Ile Gln Gln
1               5                   10                  15

Ile Leu Asp Ala Met Arg Gly Asn Lys Ala Val Ile Ala Cys Val Asn
            20                  25                  30

Ser Glu Ser Ser Val Thr Leu Ser Gly Asp Leu Asp Val Ile Ala Asn
        35                  40                  45

Leu Gln Thr Ala Leu Asp Lys Glu Gly Ile Phe Thr Arg Lys Leu Lys
    50                  55                  60

Val Asp Val Ala Tyr His Ser
65                  70


<210> SEQ ID NO 134
<211> LENGTH: 75
<212> TYPE: PRT
<213> ORGANISM: Penicillium coprobium PF1169

<400> SEQUENCE: 134

Leu Glu Asn Leu Glu Thr Ala Leu Ala Arg Asn Ala Pro Ile Tyr Ala
1               5                   10                  15

Glu Val Thr Gly Tyr Ala Asn Tyr Ser Asp Ala Tyr Asp Ile Thr Ala
            20                  25                  30

Pro Ala Asp Asp Leu Met Gly Arg Tyr Met Ser Ile Thr Lys Ala Ile
        35                  40                  45

Glu Gln Ala Gln Leu Asn Ile Asn Glu Ile Asp Tyr Ile Asn Ala His
    50                  55                  60

Gly Thr Ser Thr Gln Leu Asn Asp Leu Asn Glu
65                  70                  75


<210> SEQ ID NO 135
<211> LENGTH: 53
<212> TYPE: PRT
<213> ORGANISM: Penicillium coprobium PF1169

<400> SEQUENCE: 135

Met Ala Met Lys Lys Ala Leu Lys Gln Ala Gln Leu Arg Pro Ser Ala
1               5                   10                  15

Val Asp Tyr Val Asn Ala His Ala Thr Ser Thr Ile Val Gly Asp Ala
```

```
            20                  25                  30

Ala Glu Asn Ala Ala Ile Lys Ala Leu Leu Leu Gly Ala Asp Gly Lys
        35                  40                  45

Asp Lys Ala Ala Asp
    50


<210> SEQ ID NO 136
<211> LENGTH: 38
<212> TYPE: PRT
<213> ORGANISM: Penicillium coprobium PF1169

<400> SEQUENCE: 136

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
            20                  25                  30

Ser Leu Val Ala Leu His
        35


<210> SEQ ID NO 137
<211> LENGTH: 76
<212> TYPE: PRT
<213> ORGANISM: Penicillium coprobium PF1169

<400> SEQUENCE: 137

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75


<210> SEQ ID NO 138
<211> LENGTH: 85
<212> TYPE: PRT
<213> ORGANISM: Penicillium coprobium PF1169

<400> SEQUENCE: 138

Ile Gly Ser Ile Lys Pro Asn Ile Gly His Leu Glu Ala Gly Ala Gly
1               5                   10                  15

Val Met Gly Phe Ile Lys Ala Ile Leu Ser Ile Gln Lys Gly Val Leu
            20                  25                  30

Ala Pro Gln Ala Asn Leu Thr Lys Leu Asn Ser Arg Ile Asp Trp Lys
        35                  40                  45

Thr Ala Gly Val Lys Val Val Gln Glu Ala Thr Pro Trp Pro Ser Ser
    50                  55                  60

Asp Ser Ile Arg Arg Ala Gly Val Cys Ser Tyr Gly Tyr Gly Gly Thr
65                  70                  75                  80

Val Ser His Ala Val
                85


<210> SEQ ID NO 139
<211> LENGTH: 57
<212> TYPE: PRT
<213> ORGANISM: Penicillium coprobium PF1169
```

<400> SEQUENCE: 139

```
Asn Ala Ala Gly Ala His Phe Leu Thr Glu Asp Ile Gly Leu Phe Asp
1               5                   10                  15

Ala Pro Phe Phe Asn Ile Thr Leu Gln Glu Ala Gln Thr Met Asp Pro
            20                  25                  30

Gln Gln Arg Ile Phe Leu Glu Cys Val Tyr Glu Ala Leu Glu Asn Gly
        35                  40                  45

Gly Ile Pro Thr His Glu Ile Thr Gly
    50                  55
```

<210> SEQ ID NO 140
<211> LENGTH: 68
<212> TYPE: PRT
<213> ORGANISM: Penicillium coprobium PF1169

<400> SEQUENCE: 140

```
Leu Ser Ser Asp Gly Arg Cys His Thr Phe Asp Glu Lys Ala Asn Gly
1               5                   10                  15

Tyr Ala Arg Gly Glu Ala Val Gly Cys Leu Ile Leu Lys Pro Leu Ala
            20                  25                  30

Lys Ala Leu His Asp Gln Asn Lys Ile Arg Ala Val Ile Arg Gly Thr
        35                  40                  45

Gly Ser Asn Gln Asp Gly Arg Thr Ala Gly Ile Thr Val Pro Asn Gly
    50                  55                  60

Ala Ala Gln Glu
65
```

<210> SEQ ID NO 141
<211> LENGTH: 37
<212> TYPE: PRT
<213> ORGANISM: Penicillium coprobium PF1169

<400> SEQUENCE: 141

```
Ser Phe Asp Ser Arg Ala Glu Gly Tyr Ala Arg Gly Glu Gly Val Gly
1               5                   10                  15

Thr Val Val Val Lys Pro Leu Ser Thr Ala Ile Arg Asp Gly Asp Thr
            20                  25                  30

Ile Arg Ala Val Ile
        35
```

<210> SEQ ID NO 142
<211> LENGTH: 72
<212> TYPE: PRT
<213> ORGANISM: Penicillium coprobium PF1169

<400> SEQUENCE: 142

```
Gly Ile Pro Ile Asp Thr Leu Pro Gly Ser Asn Thr Ala Val Tyr Ser
1               5                   10                  15

Gly Ser Met Thr Asn Asp Tyr Glu Leu Leu Ser Thr Arg Asp Ile Tyr
            20                  25                  30

Asp Met Pro His Asn Ser Ala Thr Gly Asn Gly Arg Thr Met Leu Ala
        35                  40                  45

Asn Arg Leu Ser Trp Phe Phe Asp Leu Gln Gly Pro Ser Ile Met Met
    50                  55                  60

Asp Thr Ala Cys Ser Ser Ser Leu
65                  70
```

<210> SEQ ID NO 143
<211> LENGTH: 83
<212> TYPE: PRT
<213> ORGANISM: Penicillium coprobium PF1169

<400> SEQUENCE: 143

```
Ala Gln Gln Ser Leu Ile Leu Ala Thr Tyr Ala Arg Ala Gly Leu Ser
1               5                   10                  15

Pro Gln Asn Asn Pro Glu Asp Arg Cys Gln Tyr Phe Glu Ala His Gly
            20                  25                  30

Thr Gly Thr Gln Ala Gly Asp Pro Gln Glu Ala Ala Ala Ile Asn Ser
        35                  40                  45

Ser Phe Phe Gly Pro Glu Ser Val Pro Asp Ser Thr Asp Arg Leu Tyr
    50                  55                  60

Val Gly Ser Ile Lys Thr Ile Ile Gly His Thr Glu Ala Thr Ala Gly
65                  70                  75                  80

Leu Ala Gly
```

<210> SEQ ID NO 144
<211> LENGTH: 69
<212> TYPE: PRT
<213> ORGANISM: Penicillium coprobium PF1169

<400> SEQUENCE: 144

```
Pro Leu Trp Arg Lys Ile Glu Thr Ala Pro Leu Asn Thr Gly Leu Thr
1               5                   10                  15

His Asp Val Glu Lys His Thr Leu Leu Gly Gln Arg Ile Pro Val Ala
            20                  25                  30

Gly Thr Asp Thr Phe Val Tyr Thr Thr Arg Leu Asp Asn Glu Thr Lys
        35                  40                  45

Pro Phe Pro Gly Ser His Pro Leu His Gly Thr Glu Ile Val Pro Ala
    50                  55                  60

Ala Gly Leu Ile Asn
65
```

<210> SEQ ID NO 145
<211> LENGTH: 64
<212> TYPE: PRT
<213> ORGANISM: Penicillium coprobium PF1169

<400> SEQUENCE: 145

```
Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro Ser
    50                  55                  60
```

<210> SEQ ID NO 146
<211> LENGTH: 81
<212> TYPE: PRT
<213> ORGANISM: Penicillium coprobium PF1169

<400> SEQUENCE: 146

```
Gly Tyr Gly Arg Gly Glu Gly Val Ala Ser Val Val Leu Lys Arg Leu
1               5                   10                  15

Gln Asp Ala Ile Asn Asp Gly Asp Pro Ile Glu Cys Val Ile Arg Ala
```

```
            20                  25                  30

Ser Gly Ala Asn Ser Asp Gly Arg Thr Met Gly Ile Thr Met Pro Asn
        35                  40                  45

Pro Lys Ala Gln Gln Ser Leu Ile Leu Ala Thr Tyr Ala Arg Ala Gly
    50                  55                  60

Leu Ser Pro Gln Asn Asn Pro Glu Asp Arg Cys Gln Tyr Phe Glu Ala
65                  70                  75                  80

His


<210> SEQ ID NO 147
<211> LENGTH: 38
<212> TYPE: PRT
<213> ORGANISM: Penicillium coprobium PF1169

<400> SEQUENCE: 147

Gly Thr Gly Asn Gly Ser Ala Met Ile Ser Asn Arg Ile Ser Trp Phe
1               5                   10                  15

Phe Asp Leu Lys Gly Pro Ser Leu Ser Leu Asp Thr Ala Cys Ser Ser
            20                  25                  30

Ser Leu Val Ala Leu His
        35


<210> SEQ ID NO 148
<211> LENGTH: 53
<212> TYPE: PRT
<213> ORGANISM: Penicillium coprobium PF1169

<400> SEQUENCE: 148

Glu Ala Thr Ser Met Asp Ala Gln Gln Arg Lys Leu Leu Glu Val Thr
1               5                   10                  15

Tyr Glu Ala Leu Glu Asn Ala Gly Val Pro Leu Glu Thr Ile Gln Gly
            20                  25                  30

Ser Asn Thr Gly Val Tyr Val Gly Asn Phe Thr Asn Asp Phe Leu Asn
        35                  40                  45

Met Gln Tyr Lys Asp
    50


<210> SEQ ID NO 149
<211> LENGTH: 82
<212> TYPE: PRT
<213> ORGANISM: Penicillium coprobium PF1169

<400> SEQUENCE: 149

Gly Ser Leu Ile Asp Ile Glu Glu Pro Ile Ile Pro Leu Ser Thr Met
1               5                   10                  15

Arg Tyr Ile Gln Gly Ala Asp Ile Val Arg Ile Ser Asp Gly Ile Ala
            20                  25                  30

Arg Thr Ser Arg Phe Arg Ser Leu Pro Arg Thr Lys Leu Arg Pro Val
        35                  40                  45

Ser Asp Gly Pro Arg Leu Leu Pro Arg Pro Glu Gly Thr Tyr Leu Ile
    50                  55                  60

Thr Gly Gly Leu Gly Ile Leu Gly Leu Glu Val Ala Asp Phe Leu Val
65                  70                  75                  80

Glu Lys


<210> SEQ ID NO 150
<211> LENGTH: 65
<212> TYPE: PRT
```

```
<213> ORGANISM: Penicillium coprobium PF1169

<400> SEQUENCE: 150

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Lys Val
    50                  55                  60

Gly
65


<210> SEQ ID NO 151
<211> LENGTH: 78
<212> TYPE: PRT
<213> ORGANISM: Penicillium coprobium PF1169
<220> FEATURE:
<221> NAME/KEY: misc_feature
<222> LOCATION: (45)..(45)
<223> OTHER INFORMATION: Xaa can be any naturally occurring amino acid

<400> SEQUENCE: 151

Gly Pro Arg Leu Leu Pro Arg Pro Glu Gly Thr Tyr Leu Ile Thr Gly
1               5                   10                  15

Gly Leu Gly Ile Leu Gly Leu Glu Val Ala Asp Phe Leu Val Glu Lys
            20                  25                  30

Gly Ala Arg Arg Val Leu Leu Ile Ser Arg Arg Ala Xaa Pro Pro Arg
        35                  40                  45

Arg Thr Trp Asp Gln Val Ala Thr Glu Phe Gln Pro Ala Ile Thr Lys
    50                  55                  60

Ile Arg Leu Leu Glu Ser Arg Gly Ala Ser Val Tyr Val Leu
65                  70                  75


<210> SEQ ID NO 152
<211> LENGTH: 76
<212> TYPE: PRT
<213> ORGANISM: Penicillium coprobium PF1169

<400> SEQUENCE: 152

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75


<210> SEQ ID NO 153
<211> LENGTH: 38
<212> TYPE: PRT
<213> ORGANISM: Penicillium coprobium PF1169

<400> SEQUENCE: 153

Asn Arg Ile Ser Tyr Phe Phe Asp Leu Arg Gly Pro Ser Ile Thr Ile
1               5                   10                  15
```

```
Asp Thr Ala Cys Ser Ser Ser Leu Val Ala Leu His Tyr Ala Val Gln
            20                  25                  30

Ser Leu Arg Asn Gly Glu
        35


<210> SEQ ID NO 154
<211> LENGTH: 74
<212> TYPE: PRT
<213> ORGANISM: Penicillium coprobium PF1169

<400> SEQUENCE: 154

Gly Ser Gly Leu Thr Val Leu Ala Asn Arg Ile Thr His Cys Phe Asp
1               5                   10                  15

Leu Arg Gly Pro Ser His Val Val Asp Thr Ala Cys Ser Ser Ser Leu
            20                  25                  30

Tyr Ala Leu His Ser Ala Cys Leu Ala Leu Asp Ser Arg Asp Cys Asp
        35                  40                  45

Gly Ala Val Val Ala Ala Ala Asn Leu Ile Gln Ser Pro Glu Gln Gln
    50                  55                  60

Met Ile Ala Val Lys Ala Gly Ile Leu Ser
65                  70


<210> SEQ ID NO 155
<211> LENGTH: 57
<212> TYPE: PRT
<213> ORGANISM: Penicillium coprobium PF1169

<400> SEQUENCE: 155

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu
    50                  55


<210> SEQ ID NO 156
<211> LENGTH: 72
<212> TYPE: PRT
<213> ORGANISM: Penicillium coprobium PF1169

<400> SEQUENCE: 156

His Leu Asn Leu Met Gly Pro Ser Thr Ala Val Asp Ala Ala Cys Ala
1               5                   10                  15

Ser Ser Leu Val Ala Ile His His Gly Val Gln Ala Ile Lys Leu Gly
            20                  25                  30

Glu Ser Arg Val Ala Ile Val Gly Gly Val Asn Ala Leu Cys Gly Pro
        35                  40                  45

Gly Leu Thr Arg Val Leu Asp Lys Ala Gly Ser Ile Ser Ser Asp Gly
    50                  55                  60

Ser Cys Lys Ser Phe Asp Asp Asp
65                  70


<210> SEQ ID NO 157
<211> LENGTH: 81
<212> TYPE: PRT
<213> ORGANISM: Penicillium coprobium PF1169
```

<400> SEQUENCE: 157

Leu Lys Gly Thr Gly Gly Gln Met Leu Gln Asn Val Val Leu Arg Val
1               5                   10                  15

Pro Val Ala Ile Asn Ala Pro Arg Ser Val Gln Val Val Val Gln Gln
            20                  25                  30

Asp Gln Val Lys Val Val Ser Arg Leu Ile Pro Ser Glu Ala Ser Val
        35                  40                  45

Leu Asp Asp Asp Ala Ser Trp Val Thr His Thr Thr Ala Tyr Trp Asp
    50                  55                  60

Arg Arg Val Leu Gly Ser Glu Asp Arg Ile Asp Leu Ala Ala Val Lys
65                  70                  75                  80

Ser

<210> SEQ ID NO 158
<211> LENGTH: 82
<212> TYPE: PRT
<213> ORGANISM: Penicillium coprobium PF1169

<400> SEQUENCE: 158

Ile Met Gly Thr Lys Thr Ser Cys Phe Val Gly Ser Phe Ser Ala Asp
1               5                   10                  15

Tyr Thr Asp Leu Leu Leu Arg Asp Pro Glu Cys Val Pro Met Tyr Gln
            20                  25                  30

Cys Thr Asn Ala Gly Gln Ser Arg Ala Met Thr Ala Asn Arg Leu Ser
        35                  40                  45

Tyr Phe Phe Asp Leu Lys Gly Pro Ser Val Thr Val Asp Thr Ala Cys
    50                  55                  60

Ser Gly Ser Leu Val Ala Leu His Leu Ala Cys Gln Ser Leu Arg Thr
65                  70                  75                  80

Gly Asp

<210> SEQ ID NO 159
<211> LENGTH: 75
<212> TYPE: PRT
<213> ORGANISM: Penicillium coprobium PF1169

<400> SEQUENCE: 159

Gly Ser Gly Leu Thr Val Leu Ala Asn Arg Ile Thr His Cys Phe Asp
1               5                   10                  15

Leu Arg Gly Pro Ser His Val Val Asp Thr Ala Cys Ser Ser Ser Leu
            20                  25                  30

Tyr Ala Leu His Ser Ala Cys Phe Gly Pro Leu Asn Ser Arg Asp Cys
        35                  40                  45

Asp Gly Ala Val Val Ala Ala Ala Asn Leu Ile Gln Ser Pro Glu Gln
    50                  55                  60

Gln Met Ile Ala Val Lys Arg Asp Ser Ile Ala
65                  70                  75

<210> SEQ ID NO 160
<211> LENGTH: 28
<212> TYPE: PRT
<213> ORGANISM: Penicillium coprobium PF1169

<400> SEQUENCE: 160

Pro Trp Pro Thr Thr Gly Leu Arg Arg Ala Ser Val Asn Ser Phe Gly
1               5                   10                  15

Tyr Gly Gly Thr Asn Ala His Cys Val Leu Asp Asp

```
            20                  25


<210> SEQ ID NO 161
<211> LENGTH: 64
<212> TYPE: PRT
<213> ORGANISM: Penicillium coprobium PF1169

<400> SEQUENCE: 161

Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Glu Gly
    50                  55                  60


<210> SEQ ID NO 162
<211> LENGTH: 60
<212> TYPE: PRT
<213> ORGANISM: Penicillium coprobium PF1169

<400> SEQUENCE: 162

Ile Ala Pro Asn Ile His Phe Lys Met Pro Asn Pro Gln Ile Pro Phe
1               5                   10                  15

Asn Glu Ala Asn Leu His Val Pro Leu Glu Pro Thr Pro Trp Pro Ala
            20                  25                  30

Gly Arg Pro Glu Arg Ile Ser Val Asn Ser Phe Gly Ile Gly Gly Ser
        35                  40                  45

Asn Ala His Ala Ile Leu Glu Ser Ala Ser Thr Val
    50                  55                  60


<210> SEQ ID NO 163
<211> LENGTH: 34
<212> TYPE: PRT
<213> ORGANISM: Penicillium coprobium PF1169

<400> SEQUENCE: 163

Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser


<210> SEQ ID NO 164
<211> LENGTH: 51
<212> TYPE: PRT
<213> ORGANISM: Penicillium coprobium PF1169

<400> SEQUENCE: 164

Pro Trp Pro Ser Glu Gly Leu Arg Arg Ile Ser Val Asn Ser Phe Gly
1               5                   10                  15

Phe Gly Gly Ser Asn Thr His Val Ile Leu Asp Asp Ala Leu His Tyr
            20                  25                  30

Met Gln Gln Arg Gly Leu Thr Gly Asn His Cys Thr Ala Arg Leu Pro
        35                  40                  45

Gly Ile Leu
    50
```

<210> SEQ ID NO 165
<211> LENGTH: 71
<212> TYPE: PRT
<213> ORGANISM: Penicillium coprobium PF1169
<220> FEATURE:
<221> NAME/KEY: misc_feature
<222> LOCATION: (5)..(5)
<223> OTHER INFORMATION: Xaa can be any naturally occurring amino acid

<400> SEQUENCE: 165

```
Ile Gly His Thr Xaa Gly Ser Ala Gly Leu Ala Ser Leu Ile Gly Ser
1               5                   10                  15

Ser Leu Ala Met Lys His Gly Val Ile Pro Pro Asn Leu His Phe Gly
            20                  25                  30

Gln Leu Ser Glu Lys Val Ala Pro Phe Tyr Thr His Leu Asn Ile Pro
        35                  40                  45

Thr Glu Pro Val Pro Trp Pro Asn Ser Thr Ser Ser Gln Val Lys Arg
    50                  55                  60

Ala Ser Ile Asn Ser Phe Gly
65                  70
```

<210> SEQ ID NO 166
<211> LENGTH: 74
<212> TYPE: PRT
<213> ORGANISM: Penicillium coprobium PF1169

<400> SEQUENCE: 166

```
Gly Ser Asn Thr Ala Val Tyr Ser Gly Ser Met Thr Asn Asp Tyr Glu
1               5                   10                  15

Leu Leu Ser Thr Arg Asp Ile Tyr Asp Met Pro His Asn Ser Ala Thr
            20                  25                  30

Gly Asn Gly Arg Thr Met Leu Ala Asn Arg Leu Ser Trp Phe Phe Asp
        35                  40                  45

Leu Gln Gly Pro Ser Ile Met Met Asp Thr Ala Cys Ser Ser Ser Leu
    50                  55                  60

Thr Ala Val His Leu Ala Ala Gln Ser Leu
65                  70
```

<210> SEQ ID NO 167
<211> LENGTH: 85
<212> TYPE: PRT
<213> ORGANISM: Penicillium coprobium PF1169

<400> SEQUENCE: 167

```
Asp Ala Gln Phe Phe Gly Thr Lys Pro Val Glu Ala Asn Ser Ile Asp
1               5                   10                  15

Pro Gln Gln Arg Leu Leu Leu Glu Thr Val Tyr Glu Gly Leu Glu Thr
            20                  25                  30

Ser Gly Ile Pro Met Glu Arg Leu Gln Gly Ser Asn Thr Ala Val Tyr
        35                  40                  45

Val Gly Leu Met Thr Asn Asp Tyr Ala Asp Met Leu Gly Arg Asp Met
    50                  55                  60

Gln Asn Phe Pro Thr Tyr Phe Ala Ser Gly Thr Ala Arg Ser Ile Leu
65                  70                  75                  80

Ser Asn Arg Val Ser
                85
```

<210> SEQ ID NO 168
<211> LENGTH: 60
<212> TYPE: PRT

<213> ORGANISM: Penicillium coprobium PF1169

<400> SEQUENCE: 168

Val Val Ala Cys Val Asn Ser Pro Ala Ser Thr Thr Leu Ser Gly Asp
1 5 10 15

Val Asp Tyr Ile Asn Gln Leu Glu Ala Arg Leu Gln Gln Asp Gly His
20 25 30

Phe Ala Arg Lys Leu Arg Ile Asp Thr Ala Tyr His Ser Pro His Met
35 40 45

Glu Glu Leu Val Gly Val Val Gly Asp Ala Ile Ser
50 55 60

<210> SEQ ID NO 169
<211> LENGTH: 56
<212> TYPE: PRT
<213> ORGANISM: Penicillium coprobium PF1169

<400> SEQUENCE: 169

Phe Tyr Gly Met Thr Ser Asp Asp Tyr Arg Glu Val Asn Ser Gly Gln
1 5 10 15

Asp Ile Asp Thr Tyr Phe Ile Pro Gly Gly Asn Arg Ala Phe Thr Pro
20 25 30

Gly Arg Ile Asn Tyr Tyr Phe Lys Phe Ser Gly Pro Ser Val Ser Val
35 40 45

Asp Thr Ala Cys Ser Ser Ser Leu
50 55

<210> SEQ ID NO 170
<211> LENGTH: 53
<212> TYPE: PRT
<213> ORGANISM: Penicillium coprobium PF1169

<400> SEQUENCE: 170

Val Ala Ile Val Gly Gly Val Asn Ala Leu Cys Gly Pro Gly Leu Thr
1 5 10 15

Arg Val Leu Asp Lys Ala Gly Ala Ile Ser Ser Asp Gly Ser Cys Lys
20 25 30

Ser Phe Asp Asp Asp Ala His Gly Tyr Ala Arg Gly Glu Gly Ala Gly
35 40 45

Ala Leu Val Thr Lys
50

<210> SEQ ID NO 171
<211> LENGTH: 40
<212> TYPE: PRT
<213> ORGANISM: Penicillium coprobium PF1169

<400> SEQUENCE: 171

Gln Leu Gly Thr Thr Cys Val Gln Met Ala Leu Thr Lys Tyr Trp Thr
1 5 10 15

Ser Leu Gly Val Thr Pro Ser Phe Val Met Gly His Ser Leu Gly Glu
20 25 30

Phe Ala Ala Leu Asn Ala Ala Gly
35 40

<210> SEQ ID NO 172
<211> LENGTH: 69
<212> TYPE: PRT
<213> ORGANISM: Penicillium coprobium PF1169

<400> SEQUENCE: 172

```
Arg Glu Trp Met Thr Ala Glu Gly Lys Asp His Asn Leu Ser Asp Ile
1               5                   10                  15

Leu Thr Thr Leu Ala Thr Arg Arg Asp His His Asp Tyr Arg Ala Ala
            20                  25                  30

Leu Val Val Asp Asp Asn Arg Asp Ala Glu Leu Ala Leu Gln Ala Leu
        35                  40                  45

Glu His Gly Val Asp Gln Thr Phe Thr Thr Gln Ser Arg Val Phe Gly
    50                  55                  60

Ala Asp Ile Ser Lys
65
```

<210> SEQ ID NO 173
<211> LENGTH: 51
<212> TYPE: PRT
<213> ORGANISM: Penicillium coprobium PF1169

<400> SEQUENCE: 173

```
Pro Trp Pro Ser Glu Gly Leu Arg Arg Ile Ser Val Asn Ser Phe Gly
1               5                   10                  15

Phe Gly Gly Ser Asn Thr His Val Ile Leu Asp Asp Ala Leu His Tyr
            20                  25                  30

Met Gln Gln Arg Gly Leu Thr Gly Asn His Cys Thr Ala Arg Leu Pro
        35                  40                  45

Gly Ile Leu
    50
```

<210> SEQ ID NO 174
<211> LENGTH: 71
<212> TYPE: PRT
<213> ORGANISM: Penicillium coprobium PF1169

<400> SEQUENCE: 174

```
Phe Val Glu Met His Gly Thr Gly Thr Lys Ala Gly Asp Pro Val Glu
1               5                   10                  15

Ala Ala Ala Val His Ala Ala Leu Gly Lys Asn Arg Thr Leu Arg Asn
            20                  25                  30

Pro Leu Tyr Ile Gly Ser Val Lys Ser Asn Ile Gly His Leu Glu Gly
        35                  40                  45

Ala Ser Gly Ile Val Ala Val Ile Lys Ala Ala Met Met Leu Asp Arg
    50                  55                  60

Asp Leu Met Leu Pro Asn Ala
65                  70
```

<210> SEQ ID NO 175
<211> LENGTH: 41
<212> TYPE: PRT
<213> ORGANISM: Penicillium coprobium PF1169

<400> SEQUENCE: 175

```
Leu Ala Ile Val Gly Met Ala Cys Arg Leu Pro Gly Gln Ile Thr Thr
1               5                   10                  15

Pro Gln Glu Leu Trp Glu Leu Cys Ser Arg Gly Arg Ser Ala Trp Ser
            20                  25                  30

Glu Ile Pro Pro Glu Arg Phe Asn Pro
        35                  40
```

<210> SEQ ID NO 176

<211> LENGTH: 64
<212> TYPE: PRT
<213> ORGANISM: Penicillium coprobium PF1169

<400> SEQUENCE: 176

```
Gln Leu Gly Thr Thr Cys Val Gln Met Ala Leu Thr Lys Tyr Trp Thr
1               5                   10                  15

Ser Leu Gly Val Thr Pro Ser Phe Val Met Gly His Ser Leu Gly Glu
            20                  25                  30

Phe Ala Ala Leu Asn Ala Ala Gly Val Leu Thr Ile Ser Asp Thr Ile
        35                  40                  45

Tyr Leu Ala Gly Arg Arg Ala Gln Leu Leu Thr Glu Gln Ile Glu Gly
    50                  55                  60
```

<210> SEQ ID NO 177
<211> LENGTH: 74
<212> TYPE: PRT
<213> ORGANISM: Penicillium coprobium PF1169

<400> SEQUENCE: 177

```
Gly Ala Ser Val Tyr Val Leu Ala Leu Asp Ile Thr Lys Pro Asp Ala
1               5                   10                  15

Val Glu Gln Leu Ser Thr Ala Leu Asp Arg Leu Ala Leu Pro Ser Val
            20                  25                  30

Gln Gly Val Val His Ala Ala Gly Val Leu Asp Asn Glu Leu Val Met
        35                  40                  45

Gln Thr Thr Gln Glu Ala Phe Asn Arg Val Leu Ala Pro Lys Ile Ala
    50                  55                  60

Gly Ala Leu Ala Leu His Glu Pro Phe Pro
65                  70
```

<210> SEQ ID NO 178
<211> LENGTH: 72
<212> TYPE: PRT
<213> ORGANISM: Penicillium coprobium PF1169

<400> SEQUENCE: 178

```
Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser Met Arg Thr Ala Ile Ile Leu Ala Tyr Tyr Arg Gly Lys Val
        35                  40                  45

Ala Gln Pro Leu Glu Gly Leu Gly Ala Met Val Ala Val Gly Leu Ser
    50                  55                  60

Pro Asp Glu Val Ala Gln Tyr Met
65                  70
```

<210> SEQ ID NO 179
<211> LENGTH: 70
<212> TYPE: PRT
<213> ORGANISM: Penicillium coprobium PF1169

<400> SEQUENCE: 179

```
Gly Arg Phe Leu Ser Ser Asp Gly Arg Cys His Thr Phe Asp Glu Lys
1               5                   10                  15

Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
```

```
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70


<210> SEQ ID NO 180
<211> LENGTH: 51
<212> TYPE: PRT
<213> ORGANISM: Penicillium coprobium PF1169

<400> SEQUENCE: 180

Ser Ser Phe Leu Thr Ser Thr Val Gln Gln Ile Val Glu Glu Thr Ile
1               5                   10                  15

Gln Gly Gly Thr Gly Gln Val Val Met Glu Ser Asp Leu Met Gln Thr
            20                  25                  30

Glu Phe Leu Glu Ala Ala Asn Gly His Arg Met Asn Asp Cys Gly Val
        35                  40                  45

Val Thr Ser
    50


<210> SEQ ID NO 181
<211> LENGTH: 64
<212> TYPE: PRT
<213> ORGANISM: Penicillium coprobium PF1169

<400> SEQUENCE: 181

Leu Leu Gly Leu Arg Leu Lys Trp Lys Glu Tyr His Gln Asp Phe Asn
1               5                   10                  15

Ala Ala His Arg Val Leu Pro Leu Pro Ser Tyr Lys Trp Asp Leu Lys
            20                  25                  30

Asn Tyr Trp Ile Pro Tyr Thr Asn Asn Phe Cys Leu Leu Lys Gly Ala
        35                  40                  45

Pro Ala Ala Pro Val Ala Glu Ala Thr Pro Ile Ser Val Phe Leu Ser
    50                  55                  60


<210> SEQ ID NO 182
<211> LENGTH: 26
<212> TYPE: PRT
<213> ORGANISM: Penicillium coprobium PF1169

<400> SEQUENCE: 182

Ser Phe Arg Arg Gln Glu Asp Thr Trp Lys Val Leu Ser Asn Ala Thr
1               5                   10                  15

Ser Thr Leu Tyr Leu Ala Gly Ile Glu Ile
            20                  25


<210> SEQ ID NO 183
<211> LENGTH: 65
<212> TYPE: PRT
<213> ORGANISM: Penicillium coprobium PF1169

<400> SEQUENCE: 183

Ala Gly Gly Asn Thr Thr Val Ala Leu Glu Asp Ala Pro Ile Arg Thr
1               5                   10                  15

Arg Ser Gly Ser Asp Pro Arg Ser Leu His Pro Ile Ala Ile Ser Ala
            20                  25                  30

Lys Ser Lys Val Ser Leu Arg Gly Asn Leu Glu Asn Leu Leu Ala Tyr
        35                  40                  45
```

```
Leu Asp Thr His Pro Asp Val Ser Leu Ser Asp Leu Ser Tyr Thr Thr
    50                  55                  60

Thr
65


<210> SEQ ID NO 184
<211> LENGTH: 96
<212> TYPE: PRT
<213> ORGANISM: Penicillium coprobium PF1169

<400> SEQUENCE: 184

Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45

Ile Gly Thr Phe Tyr Gly Gln Ala Ser Asp Asp Tyr Arg Glu Val Asn
    50                  55                  60

Thr Ala Gln Glu Ile Ser Thr Tyr Phe Ile Pro Gly Gly Cys Arg Ala
65                  70                  75                  80

Phe Gly Pro Gly Arg Ile Asn Tyr Phe Phe Lys Phe Leu Gly Pro Ala
                85                  90                  95


<210> SEQ ID NO 185
<211> LENGTH: 58
<212> TYPE: PRT
<213> ORGANISM: Penicillium coprobium PF1169

<400> SEQUENCE: 185

Phe Leu Gln Ile Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met
    50                  55


<210> SEQ ID NO 186
<211> LENGTH: 59
<212> TYPE: PRT
<213> ORGANISM: Penicillium coprobium PF1169

<400> SEQUENCE: 186

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55


<210> SEQ ID NO 187
<211> LENGTH: 31
<212> TYPE: PRT
<213> ORGANISM: Penicillium coprobium PF1169

<400> SEQUENCE: 187
```

```
Leu Phe Leu Phe Pro Asp Gly Ser Gly Ser Ala Thr Ser Tyr Ala Thr
1               5                   10                  15

Ile Pro Gly Ile Ser Pro Asp Val Cys Val Tyr Gly Leu Asn Cys
            20                  25                  30


<210> SEQ ID NO 188
<211> LENGTH: 26
<212> TYPE: PRT
<213> ORGANISM: Penicillium coprobium PF1169

<400> SEQUENCE: 188

Ala Lys His Pro Pro Ala Thr Ser Ile Leu Leu Gln Gly Asn Pro Lys
1               5                   10                  15

Thr Ala Thr Gln Ser Phe Ile Phe Val Pro
            20                  25


<210> SEQ ID NO 189
<211> LENGTH: 38
<212> TYPE: PRT
<213> ORGANISM: Penicillium coprobium PF1169

<400> SEQUENCE: 189

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35


<210> SEQ ID NO 190
<211> LENGTH: 76
<212> TYPE: PRT
<213> ORGANISM: Penicillium coprobium PF1169

<400> SEQUENCE: 190

Ala Ile His His Gly Val Gln Ala Ile Lys Leu Gly Glu Ser Arg Val
1               5                   10                  15

Ala Ile Val Gly Gly Val Asn Ala Leu Cys Gly Pro Gly Leu Thr Arg
            20                  25                  30

Val Leu Asp Lys Ala Gly Ala Ile Ser Ser Asp Gly Ser Cys Lys Ser
        35                  40                  45

Phe Asp Asp Asp Ala His Gly Tyr Ala Arg Gly Glu Gly Ala Gly Ala
    50                  55                  60

Leu Val Leu Lys Ser Leu His Gln Ala Leu Leu Asp
65                  70                  75


<210> SEQ ID NO 191
<211> LENGTH: 65
<212> TYPE: PRT
<213> ORGANISM: Penicillium coprobium PF1169

<400> SEQUENCE: 191

Val Trp Ile Glu Ile Gly Pro His Pro Val Cys Leu Gly Phe Val Lys
1               5                   10                  15

Ala Thr Leu Glu Ser Val Ala Val Ala Val Pro Ser Leu Arg Arg Gly
            20                  25                  30

Glu Asn Ala Trp Cys Thr Leu Ala Gln Ser Leu Thr Thr Leu His Asn
        35                  40                  45

Ala Gly Val Pro Val Gly Trp Ser Glu Phe His Arg Pro Phe Glu Arg
```

```
    50                  55                  60

Ala
65


<210> SEQ ID NO 192
<211> LENGTH: 53
<212> TYPE: PRT
<213> ORGANISM: Penicillium coprobium PF1169

<400> SEQUENCE: 192

Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala
    50


<210> SEQ ID NO 193
<211> LENGTH: 40
<212> TYPE: PRT
<213> ORGANISM: Penicillium coprobium PF1169

<400> SEQUENCE: 193

Val Asp Thr Ala Cys Ser Ser Ser Leu Tyr Ala Leu His Ser Ala Cys
1               5                   10                  15

Phe Gly Pro Leu Asn Ser Arg Asp Cys Asp Gly Ala Val Val Ala Ala
            20                  25                  30

Ala Asn Leu Ile Gln Ser Pro Glu
        35                  40


<210> SEQ ID NO 194
<211> LENGTH: 68
<212> TYPE: PRT
<213> ORGANISM: Penicillium coprobium PF1169

<400> SEQUENCE: 194

Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly Asp Leu Asp Val Ile Ala Asn Leu Gln Thr
        35                  40                  45

Ala Leu Asp Lys Glu Gly Ile Phe Thr Arg Lys Leu Lys Val Asp Val
    50                  55                  60

Ala Tyr His Ser
65


<210> SEQ ID NO 195
<211> LENGTH: 62
<212> TYPE: PRT
<213> ORGANISM: Penicillium coprobium PF1169

<400> SEQUENCE: 195

Phe Leu Asp Asp Leu Ala Phe Thr Val Asn Glu Arg Arg Ser Ile Phe
1               5                   10                  15

Pro Trp Lys Ala Ala Val Val Gly Asp Thr Met Glu Gly Leu Ala Ala
            20                  25                  30
```

```
Ser Leu Ala Gln Asn Ile Lys Pro Arg Ser Val Leu Arg Met Pro Thr
        35                  40                  45

Leu Gly Phe Val Phe Thr Gly Gln Gly Ala Gln Trp Pro Gly
    50                  55                  60


<210> SEQ ID NO 196
<211> LENGTH: 76
<212> TYPE: PRT
<213> ORGANISM: Penicillium coprobium PF1169

<400> SEQUENCE: 196

Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75


<210> SEQ ID NO 197
<211> LENGTH: 79
<212> TYPE: PRT
<213> ORGANISM: Penicillium coprobium PF1169

<400> SEQUENCE: 197

Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75


<210> SEQ ID NO 198
<211> LENGTH: 40
<212> TYPE: PRT
<213> ORGANISM: Penicillium coprobium PF1169

<400> SEQUENCE: 198

Phe Asn Leu Lys Gly Ile Ser Gln Ser Ile Ala Ser Ala Cys Ala Thr
1               5                   10                  15

Ser Ala Asp Ala Ile Gly Tyr Ala Phe His Leu Ile Ala Ala Gly Lys
            20                  25                  30

Gln Asp Leu Met Leu Ala Gly Gly
        35                  40


<210> SEQ ID NO 199
<211> LENGTH: 70
<212> TYPE: PRT
<213> ORGANISM: Penicillium coprobium PF1169

<400> SEQUENCE: 199

Gly Arg Phe Leu Ser Ser Asp Gly Arg Cys His Thr Phe Asp Glu Lys
1               5                   10                  15
```

```
Ala Asn Gly Tyr Ala Arg Gly Glu Ala Val Gly Cys Leu Ile Leu Lys
            20                  25                  30

Pro Leu Ala Lys Ala Leu His Asp Gln Asn Lys Ile Arg Ala Val Ile
        35                  40                  45

Arg Gly Thr Gly Ser Asn Gln Asp Gly Arg Thr Ala Gly Ile Thr Val
    50                  55                  60

Pro Asn Gly Ala Ala Gln
65                  70


<210> SEQ ID NO 200
<211> LENGTH: 284
<212> TYPE: PRT
<213> ORGANISM: Penicillium coprobium PF1169

<400> SEQUENCE: 200

Leu Ser Val Lys Arg Val Gly Ile His Asp Asp Phe Phe Glu Leu Gly
1               5                   10                  15

Gly His Ser Leu Leu Ala Val Lys Leu Val Asn His Leu Lys Lys Val
            20                  25                  30

Phe Gly Thr Glu Leu Ser Val Ala Leu Leu Ala Gln Tyr Ser Thr Val
        35                  40                  45

Glu Ser Leu Gly Glu Ile Ile Arg Glu Asn Lys Glu Ile Lys Pro Ser
    50                  55                  60

Ile Val Ile Glu Leu Arg Ser Gly Thr Tyr Glu Gln Pro Leu Trp Leu
65                  70                  75                  80

Phe His Pro Ile Gly Gly Ser Thr Phe Cys Tyr Met Glu Leu Ser Arg
                85                  90                  95

His Leu Asn Pro Asn Arg Thr Leu Arg Ala Ile Gln Ser Pro Gly Leu
            100                 105                 110

Ile Glu Ala Asp Ala Ala Glu Val Ala Ile Glu Glu Met Ala Thr Leu
        115                 120                 125

Tyr Ile Ala Glu Met Gln Lys Met Gln Pro Gln Gly Pro Tyr Phe Leu
    130                 135                 140

Gly Gly Trp Cys Phe Gly Gly Ala Ile Ala Tyr Glu Ile Ser Arg Gln
145                 150                 155                 160

Leu Arg Gln Met Gly Gln Gln Val Thr Gly Ile Val Met Ile Asp Thr
                165                 170                 175

Arg Ala Pro Ile Pro Glu Asn Val Pro Glu Asp Ala Asp Asp Ala Met
            180                 185                 190

Leu Leu Ser Trp Phe Ala Arg Asp Leu Ala Val Pro Tyr Gly Lys Lys
        195                 200                 205

Leu Thr Ile Ser Ala Gln Tyr Leu Arg Glu Leu Ser Pro Asp His Met
    210                 215                 220

Phe Asp His Val Leu Lys Glu Ala Lys Ala Ile Asn Val Ile Pro Leu
225                 230                 235                 240

Asp Ala Asn Pro Ser Asp Phe Arg Leu Tyr Phe Asp Thr Tyr Leu Ala
                245                 250                 255

Asn Gly Val Ala Leu Gln Thr Tyr Phe Pro Glu Pro Glu Asp Phe Pro
            260                 265                 270

Ile Leu Leu Val Lys Ala Lys Asp Glu Ser Glu Asp
        275                 280


<210> SEQ ID NO 201
<211> LENGTH: 73
<212> TYPE: PRT
```

<213> ORGANISM: Penicillium coprobium PF1169

<400> SEQUENCE: 201

```
Pro Met Asn Lys Asp Lys Val Tyr Trp Ser Ala Ile Ile Arg Thr Leu
1               5                   10                  15

Val Ala Lys Glu Met Arg Val Glu Pro Glu Thr Ile Asp Pro Glu Gln
            20                  25                  30

Lys Phe Thr Thr Tyr Gly Leu Asp Ser Ile Val Ala Leu Ser Val Ser
        35                  40                  45

Gly Asp Leu Glu Asp Leu Thr Lys Leu Glu Leu Glu Pro Thr Leu Leu
    50                  55                  60

Trp Asp Tyr Pro Thr Ile Asn Ala Leu
65                  70
```

<210> SEQ ID NO 202
<211> LENGTH: 63
<212> TYPE: PRT
<213> ORGANISM: Penicillium coprobium PF1169

<400> SEQUENCE: 202

```
Gly Ser Leu Ile Asp Ile Glu Glu Pro Ile Ile Pro Leu Ser Thr Met
1               5                   10                  15

Arg Tyr Ile Gln Gly Ala Asp Ile Val Arg Ile Ser Asp Gly Ile Ala
            20                  25                  30

Arg Thr Ser Arg Phe Arg Ser Leu Pro Arg Thr Lys Leu Arg Pro Val
        35                  40                  45

Ser Asp Gly Pro Arg Leu Leu Pro Arg Pro Glu Gly Thr Tyr Leu
    50                  55                  60
```

<210> SEQ ID NO 203
<211> LENGTH: 69
<212> TYPE: PRT
<213> ORGANISM: Penicillium coprobium PF1169

<400> SEQUENCE: 203

```
Leu Glu Val Val Trp Glu Cys Leu Glu Asn Ser Gly Glu Thr Gln Trp
1               5                   10                  15

Arg Gly Lys Glu Ile Gly Cys Phe Val Gly Val Phe Gly Glu Asp Trp
            20                  25                  30

Leu Glu Met Ser His Lys Asp Pro Gln His Leu Asn Gln Met Phe Pro
        35                  40                  45

Ile Ala Thr Gly Gly Phe Ala Leu Ala Asn Gln Val Ser Tyr Arg Phe
    50                  55                  60

Asp Leu Thr Gly Pro
65
```

<210> SEQ ID NO 204
<211> LENGTH: 96
<212> TYPE: PRT
<213> ORGANISM: Penicillium coprobium PF1169

<400> SEQUENCE: 204

```
Phe Asp Ala Ala Phe Phe Asn Met Ser Pro Arg Glu Ala Gln Gln Thr
1               5                   10                  15

Asp Pro Met Gln Arg Leu Ala Ile Val Thr Ala Tyr Glu Ala Leu Glu
            20                  25                  30

Arg Ala Gly Tyr Val Ala Asn Arg Thr Ala Ala Thr Asn Leu His Arg
        35                  40                  45
```

```
Ile Gly Thr Phe Tyr Gly Gln Ala Ser Asp Asp Tyr Arg Glu Val Asn
    50                  55                  60

Thr Ala Gln Glu Ile Ser Thr Tyr Phe Ile Pro Gly Gly Cys Arg Ala
65                  70                  75                  80

Phe Gly Pro Gly Arg Ile Asn Tyr Phe Phe Lys Phe Leu Gly Pro Ala
                85                  90                  95


<210> SEQ ID NO 205
<211> LENGTH: 58
<212> TYPE: PRT
<213> ORGANISM: Penicillium coprobium PF1169

<400> SEQUENCE: 205

Phe Leu Gln Ile Ser Gly Pro Ser Phe Ser Ile Asp Thr Ala Cys Ser
1               5                   10                  15

Ser Ser Leu Ala Thr Ile Gln Val Cys Thr His Leu Phe His Val His
            20                  25                  30

Leu Asn Arg Gln Leu Thr Ile Ala Ala Cys Thr Ser Leu Trp Asn Gly
        35                  40                  45

Glu Thr Asp Thr Val Val Ala Gly Gly Met
    50                  55


<210> SEQ ID NO 206
<211> LENGTH: 52
<212> TYPE: PRT
<213> ORGANISM: Penicillium coprobium PF1169

<400> SEQUENCE: 206

Glu Leu Arg His Gly Lys Asn Ile Asp Lys Pro Glu Tyr Ser Gln Pro
1               5                   10                  15

Leu Cys Thr Ala Ile Gln Ile Ala Leu Val Glu Leu Leu Glu Ser Phe
            20                  25                  30

Gly Val Val Pro Lys Ala Val Val Gly His Ser Ser Gly Glu Ile Ala
        35                  40                  45

Ala Ala Tyr Val
    50


<210> SEQ ID NO 207
<211> LENGTH: 59
<212> TYPE: PRT
<213> ORGANISM: Penicillium coprobium PF1169

<400> SEQUENCE: 207

Val Tyr Ser Gly Ser Met Thr Asn Asp Tyr Glu Leu Leu Ser Thr Arg
1               5                   10                  15

Asp Ile Tyr Asp Met Pro His Asn Ser Ala Thr Gly Asn Gly Arg Thr
            20                  25                  30

Met Leu Ala Asn Arg Leu Ser Trp Phe Phe Asp Leu Gln Gly Pro Ser
        35                  40                  45

Ile Met Met Asp Thr Ala Cys Ser Ser Ser Leu
    50                  55


<210> SEQ ID NO 208
<211> LENGTH: 28
<212> TYPE: PRT
<213> ORGANISM: Penicillium coprobium PF1169

<400> SEQUENCE: 208

Pro Trp Pro Thr Thr Gly Leu Arg Arg Ala Ser Val Asn Ser Phe Gly
1               5                   10                  15
```

```
Tyr Gly Gly Thr Asn Ala His Cys Val Leu Asp Asp
            20                  25


<210> SEQ ID NO 209
<211> LENGTH: 71
<212> TYPE: PRT
<213> ORGANISM: Penicillium coprobium PF1169

<400> SEQUENCE: 209

Lys Ala Ser Leu Ser Leu Gln His Gly Met Ile Ala Pro Asn Leu Leu
1               5                   10                  15

Met Gln His Leu Asn Pro Lys Ile Lys Pro Phe Ala Ala Lys Leu Ser
            20                  25                  30

Val Pro Thr Glu Cys Ile Pro Trp Pro Ala Val Pro Asp Gly Cys Pro
        35                  40                  45

Arg Arg Ala Ser Val Asn Ser Phe Gly Phe Gly Gly Ala Asn Val His
    50                  55                  60

Val Val Leu Glu Ser Tyr Thr
65                  70


<210> SEQ ID NO 210
<211> LENGTH: 80
<212> TYPE: PRT
<213> ORGANISM: Penicillium coprobium PF1169

<400> SEQUENCE: 210

Leu Lys Gly Thr Gly Gly Gln Met Leu Gln Asn Val Val Leu Arg Val
1               5                   10                  15

Pro Val Ala Ile Asn Ala Pro Arg Ser Val Gln Val Val Val Gln Gln
            20                  25                  30

Asp Gln Val Lys Val Val Ser Arg Leu Ile Pro Ser Glu Ala Ser Val
        35                  40                  45

Leu Asp Asp Asp Ala Ser Trp Val Thr His Thr Thr Ala Tyr Trp Asp
    50                  55                  60

Arg Arg Val Leu Gly Ser Glu Asp Arg Ile Asp Leu Ala Ala Val Lys
65                  70                  75                  80


<210> SEQ ID NO 211
<211> LENGTH: 38
<212> TYPE: PRT
<213> ORGANISM: Penicillium coprobium PF1169

<400> SEQUENCE: 211

Gly Asn Gly Ser Ala Met Ile Ser Asn Arg Ile Ser Trp Phe Phe Asp
1               5                   10                  15

Leu Lys Gly Pro Ser Leu Ser Leu Asp Thr Ala Cys Ser Ser Ser Leu
            20                  25                  30

Val Ala Leu His Leu Ala
        35


<210> SEQ ID NO 212
<211> LENGTH: 76
<212> TYPE: PRT
<213> ORGANISM: Penicillium coprobium PF1169

<400> SEQUENCE: 212

Ala Ile His His Gly Val Gln Ala Ile Lys Leu Gly Glu Ser Arg Val
1               5                   10                  15

Ala Ile Val Gly Gly Val Asn Ala Leu Cys Gly Pro Gly Leu Thr Arg
```

```
            20                  25                  30

Val Leu Asp Lys Ala Gly Ala Ile Ser Ser Asp Gly Ser Cys Lys Ser
        35                  40                  45

Phe Asp Asp Asp Ala His Gly Tyr Ala Arg Gly Glu Gly Ala Gly Ala
    50                  55                  60

Leu Val Leu Lys Ser Leu His Gln Ala Leu Leu Asp
65                  70                  75


<210> SEQ ID NO 213
<211> LENGTH: 69
<212> TYPE: PRT
<213> ORGANISM: Penicillium coprobium PF1169

<400> SEQUENCE: 213

Arg Glu Trp Met Thr Ala Glu Gly Lys Asp His Asn Leu Ser Asp Ile
1               5                   10                  15

Leu Thr Thr Leu Ala Thr Arg Arg Asp His His Asp Tyr Arg Ala Ala
            20                  25                  30

Leu Val Val Asp Asp Asn Arg Asp Ala Glu Leu Ala Leu Gln Ala Leu
        35                  40                  45

Glu His Gly Val Asp Gln Thr Phe Thr Thr Gln Ser Arg Val Phe Gly
    50                  55                  60

Ala Asp Ile Ser Lys
65


<210> SEQ ID NO 214
<211> LENGTH: 53
<212> TYPE: PRT
<213> ORGANISM: Penicillium coprobium PF1169

<400> SEQUENCE: 214

Thr Ser Asp Asp Tyr Arg Glu Val Asn Ser Gly Gln Asp Ile Asp Thr
1               5                   10                  15

Tyr Phe Ile Pro Gly Gly Asn Arg Ala Phe Thr Pro Gly Arg Ile Asn
            20                  25                  30

Tyr Tyr Phe Lys Phe Ser Gly Pro Ser Val Ser Val Asp Thr Ala Cys
        35                  40                  45

Ser Ser Ser Leu Ala
    50


<210> SEQ ID NO 215
<211> LENGTH: 63
<212> TYPE: PRT
<213> ORGANISM: Penicillium coprobium PF1169

<400> SEQUENCE: 215

Ala Gly Ile Pro Leu Ala Asn Ile Met Gly Thr Lys Thr Ser Cys Phe
1               5                   10                  15

Val Gly Ser Phe Ser Ala Asp Tyr Thr Asp Leu Leu Leu Arg Asp Pro
            20                  25                  30

Glu Cys Val Pro Met Tyr Gln Cys Thr Asn Ala Gly Gln Ser Arg Ala
        35                  40                  45

Met Thr Ala Asn Arg Leu Ser Tyr Phe Phe Asp Leu Lys Gly Pro
    50                  55                  60


<210> SEQ ID NO 216
<211> LENGTH: 68
<212> TYPE: PRT
<213> ORGANISM: Penicillium coprobium PF1169
```

<400> SEQUENCE: 216

```
Met Leu Ala Val Gly Ala Ser Ala Ser Asp Ile Gln Gln Ile Leu Asp
1               5                   10                  15

Ala Met Arg Gly Asn Lys Ala Val Ile Ala Cys Val Asn Ser Glu Ser
            20                  25                  30

Ser Val Thr Leu Ser Gly Asp Leu Asp Val Ile Ala Asn Leu Gln Thr
        35                  40                  45

Ala Leu Asp Lys Glu Gly Ile Phe Thr Arg Lys Leu Lys Val Asp Val
    50                  55                  60

Ala Tyr His Ser
65
```

<210> SEQ ID NO 217
<211> LENGTH: 39
<212> TYPE: PRT
<213> ORGANISM: Penicillium coprobium PF1169

<400> SEQUENCE: 217

```
Asn Ala Ala Gly Ala His Phe Leu Thr Glu Asp Ile Gly Leu Phe Asp
1               5                   10                  15

Ala Pro Phe Phe Asn Ile Thr Leu Gln Glu Ala Gln Thr Met Asp Pro
            20                  25                  30

Gln Gln Arg Ile Phe Leu Glu
        35
```

<210> SEQ ID NO 218
<211> LENGTH: 76
<212> TYPE: PRT
<213> ORGANISM: Penicillium coprobium PF1169

<400> SEQUENCE: 218

```
Gly Pro Ser Met Thr Ile Asp Thr Ala Cys Ser Ser Ser Leu Ile Ala
1               5                   10                  15

Leu His Gln Ala Val Gln Ser Leu Arg Ser Gly Glu Thr Asp Val Ala
            20                  25                  30

Val Ala Ala Gly Thr Asn Leu Leu Leu Gly Pro Glu Gln Tyr Ile Ala
        35                  40                  45

Glu Ser Lys Leu Lys Met Leu Ser Pro Asn Gly Arg Ser Arg Met Trp
    50                  55                  60

Asp Lys Asp Ala Asp Gly Tyr Ala Arg Gly Asp Gly
65                  70                  75
```

<210> SEQ ID NO 219
<211> LENGTH: 61
<212> TYPE: PRT
<213> ORGANISM: Penicillium coprobium PF1169

<400> SEQUENCE: 219

```
Gly Leu Val Asn Ile Leu Arg Ser Trp Gly Ile Glu Pro Ser Thr Val
1               5                   10                  15

Val Gly His Ser Ser Gly Glu Ile Val Ala Ala Tyr Thr Ala Arg Ala
            20                  25                  30

Ile Ser Met Arg Thr Ala Ile Ile Leu Ala Tyr Tyr Arg Gly Lys Val
        35                  40                  45

Ala Gln Pro Leu Glu Gly Leu Gly Ala Met Val Ala Val
    50                  55                  60
```

<210> SEQ ID NO 220
<211> LENGTH: 79
<212> TYPE: PRT
<213> ORGANISM: Penicillium coprobium PF1169

<400> SEQUENCE: 220

```
Ser Val Pro Ile Glu Glu His Ser Pro Val Val Thr Gln Leu Gly Thr
1               5                   10                  15

Thr Cys Val Gln Met Ala Leu Thr Lys Tyr Trp Thr Ser Leu Gly Val
            20                  25                  30

Thr Pro Ser Phe Val Met Gly His Ser Leu Gly Glu Phe Ala Ala Leu
        35                  40                  45

Asn Ala Ala Gly Val Leu Thr Ile Ser Asp Thr Ile Tyr Leu Ala Gly
    50                  55                  60

Arg Arg Ala Gln Leu Leu Thr Glu Gln Ile Glu Gly Gly Thr His
65                  70                  75
```

<210> SEQ ID NO 221
<211> LENGTH: 81
<212> TYPE: PRT
<213> ORGANISM: Penicillium coprobium PF1169

<400> SEQUENCE: 221

```
Val Tyr Thr Gly Arg Ile Ser Leu Lys Asp Leu Gly Met Arg Cys Leu
1               5                   10                  15

Pro Leu Cys Leu Phe Leu Phe Leu Trp Thr Ile Tyr Phe Asn Thr Ala
            20                  25                  30

Tyr Ser Tyr Gln Asp Ile Lys Asp Asp Cys Lys Leu Asn Val Asn Ser
        35                  40                  45

Ser Tyr Val Leu Ala Gly Ser His Val Arg Gly Met Leu Leu Leu Gln
    50                  55                  60

Ala Ile Ala Val Val Leu Val Ile Pro Trp Ile Leu Tyr Thr Ser Ala
65                  70                  75                  80

Ser
```

<210> SEQ ID NO 222
<211> LENGTH: 82
<212> TYPE: PRT
<213> ORGANISM: Penicillium coprobium PF1169

<400> SEQUENCE: 222

```
Arg His Phe Gly Leu Trp Asp Glu Pro Arg Glu Leu Glu Asp Val Glu
1               5                   10                  15

Phe Leu Leu Lys Ala Asp Val Arg Asn Asn Ser Ala Trp Asn His Arg
            20                  25                  30

Tyr Met Leu Arg Phe Gly Pro Arg Asp Thr Ser Leu Pro Asp Ala Gly
        35                  40                  45

Met Val Asn Ala Gly Asp Leu Ser Thr Ala Pro Ala Glu Lys Gly Arg
    50                  55                  60

Leu Ser Val Val Asp Glu Asp Met Val Asp Gly Glu Leu Lys Phe Ala
65                  70                  75                  80

Gln Glu
```

<210> SEQ ID NO 223
<211> LENGTH: 35
<212> TYPE: PRT
<213> ORGANISM: Penicillium coprobium PF1169

<400> SEQUENCE: 223

```
Ile Met Arg Gly Ala Gly Cys Ala Ile Asn Asp Leu Trp Asp Arg Asn
1               5                   10                  15

Leu Asp Pro His Val Glu Arg Thr Lys Phe Arg Pro Ile Ala Arg Gly
            20                  25                  30

Ala Leu Ser
        35


<210> SEQ ID NO 224
<211> LENGTH: 86
<212> TYPE: PRT
<213> ORGANISM: Penicillium coprobium PF1169

<400> SEQUENCE: 224

Phe Pro Thr Phe Pro Pro Lys Glu Ala Asp Phe Leu Met Glu Met Phe
1               5                   10                  15

Ala Gln Asp Ser Lys Asn Tyr His Val Trp Thr Tyr Arg His Trp Leu
            20                  25                  30

Val Arg His Phe Gly Leu Trp Asp Glu Pro Arg Glu Leu Glu Asp Val
        35                  40                  45

Glu Phe Leu Leu Lys Ala Asp Val Arg Asn Asn Ser Ala Trp Asn His
    50                  55                  60

Arg Tyr Met Leu Arg Phe Gly Pro Arg Asp Thr Ser Leu Pro Asp Ala
65                  70                  75                  80

Gly Met Val Asn Ala Gly
                85


<210> SEQ ID NO 225
<211> LENGTH: 82
<212> TYPE: PRT
<213> ORGANISM: Penicillium coprobium PF1169

<400> SEQUENCE: 225

Asn His Arg Tyr Met Leu Arg Phe Gly Pro Arg Asp Thr Ser Leu Pro
1               5                   10                  15

Asp Ala Gly Met Val Asn Ala Gly Asp Leu Ser Thr Ala Pro Ala Glu
            20                  25                  30

Lys Gly Arg Leu Ser Val Val Asp Glu Asp Met Val Asp Gly Glu Leu
        35                  40                  45

Lys Phe Ala Gln Glu Ala Ile Leu Arg Ala Pro Glu Asn Arg Ser Pro
    50                  55                  60

Trp Trp Tyr Ala Arg Gly Val Leu Arg Ala Ala Gly Arg Gly Leu Gly
65                  70                  75                  80

Glu Trp


<210> SEQ ID NO 226
<211> LENGTH: 45
<212> TYPE: PRT
<213> ORGANISM: Penicillium coprobium PF1169

<400> SEQUENCE: 226

Arg Pro Thr Ser Arg Lys Leu Gly Val Tyr Pro Gln Tyr Ile Leu Gly
1               5                   10                  15

Ala Ser Ser Ala Leu Thr Ile Leu Pro Ala Trp Ala Ser Val Tyr Thr
            20                  25                  30

Gly Arg Ile Ser Leu Lys Asp Leu Gly Met Arg Cys Leu
        35                  40                  45
```

<210> SEQ ID NO 227
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 227
tacaggcggc ctaaattgtc 20

<210> SEQ ID NO 228
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 228
gaacacagcg caagagatca 20

<210> SEQ ID NO 229
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 229
cgcaagactt gaggaacaag 20

<210> SEQ ID NO 230
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 230
tgaggtcaac agtggacagg 20

<210> SEQ ID NO 231
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 231
cgcttttacg gcaatcatct 20

<210> SEQ ID NO 232
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 232
tgttcgtcgt ccttgtatgc 20

<210> SEQ ID NO 233
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 233
cagacgctgc ataggatcag 20

<210> SEQ ID NO 234
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 234
ttactagcct ctggggtgga 20

<210> SEQ ID NO 235
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 235
tctcttgcgc tgtgttcact 20

<210> SEQ ID NO 236
<211> LENGTH: 19
<212> TYPE: DNA
<213> ORGANISM: Artificial Sequence
<220> FEATURE:
<223> OTHER INFORMATION: Synthetic construct; a primer sequence for PCR

<400> SEQUENCE: 236
atgcggcctt tttcaacat 19

<210> SEQ ID NO 237
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 237
cgacgtaagg agctgtgagc 20

<210> SEQ ID NO 238
<211> LENGTH: 18
<212> TYPE: DNA
<213> ORGANISM: Artificial Sequence
<220> FEATURE:
<223> OTHER INFORMATION: Synthetic construct; a primer sequence for PCR

<400> SEQUENCE: 238
acctcgatcc tgctgcaa 18

<210> SEQ ID NO 239
<211> LENGTH: 21
<212> TYPE: DNA
<213> ORGANISM: Artificial Sequence
<220> FEATURE:
<223> OTHER INFORMATION: Synthetic construct; a primer sequence for PCR

<400> SEQUENCE: 239
ggttgtcagg atttgtcaga a 21

<210> SEQ ID NO 240
<211> LENGTH: 20

<212> TYPE: DNA
<213> ORGANISM: Artificial Sequence
<220> FEATURE:
<223> OTHER INFORMATION: Synthetic construct; a primer sequence for PCR

<400> SEQUENCE: 240
ttacttcatc cccggtggta 20

<210> SEQ ID NO 241
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 241
agagcatagc ccggttgtta 20

<210> SEQ ID NO 242
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 242
cccaccttga tttgctcagt 20

<210> SEQ ID NO 243
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 243
agagcatagc ccggttgtta 20

<210> SEQ ID NO 244
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 244
gccaccttga tttgctcagt 20

<210> SEQ ID NO 245
<211> LENGTH: 22
<212> TYPE: DNA
<213> ORGANISM: Artificial Sequence
<220> FEATURE:
<223> OTHER INFORMATION: Synthetic construct; a primer sequence for PCR

<400> SEQUENCE: 245
aagaacacag agattggtgt gg 22

<210> SEQ ID NO 246
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 246
ccaggaagac acttggaagg 20

<210> SEQ ID NO 247
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 247
agagcatagc ccggttgtta 20

<210> SEQ ID NO 248
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 248
ccaccttcga tttgctcagt 20

<210> SEQ ID NO 249
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 249
cgcaagactt gaggaacaag 20

<210> SEQ ID NO 250
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 250
tccctctacg cagaagaacc 20

<210> SEQ ID NO 251
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 251
agagcatagc ccggttgtta 20

<210> SEQ ID NO 252
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 252
ccaccttcga tttgctcagt 20

<210> SEQ ID NO 253
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 253
gaggcgctgg tgtagagaat 20

<210> SEQ ID NO 254
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 254
tgtctcccgc tttgtctctt 20

<210> SEQ ID NO 255
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 255
agacgtggag ttcctcctga 20

<210> SEQ ID NO 256
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 256
caaacttcag ttcgccatca 20

<210> SEQ ID NO 257
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 257
caactttccc acccaaagaa 20

<210> SEQ ID NO 258
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 258
aagcatgtat cggtggttcc 20

<210> SEQ ID NO 259
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 259
cgatacatgc ttcgttttgg 20

<210> SEQ ID NO 260
<211> LENGTH: 18
<212> TYPE: DNA
<213> ORGANISM: Artificial Sequence
<220> FEATURE:
<223> OTHER INFORMATION: Synthetic construct; a primer sequence for PCR

<400> SEQUENCE: 260
cagcagccct cagcacac 18

<210> SEQ ID NO 261
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 261
ggcgtctatc cgcaatacat 20

<210> SEQ ID NO 262
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 262
gagacaccgc atacccagat 20

<210> SEQ ID NO 263
<211> LENGTH: 406
<212> TYPE: DNA
<213> ORGANISM: Penicillium coprobium PF1169

<400> SEQUENCE: 263
cccagcccaa gacttgagta gactatattt attctctttg atatccatct cagcatcaag 60
tttttgacgt tgtattacta tcctcgtttg gaattctcct cccaggtctt gcttcattgc 120
ttatagcatt ctaccaaaaa cgtcactgtc atggacgggt ggtcagacat atcatcagcg 180
cctgccggat acaaggatgt tgtttggata gcagatcggg ctctgctagc ccaaggattg 240
ggatggtcaa tcaactacct ggccatgata taccaatcgc gcaaagaccg cacatacggc 300
atggccattt tgccactatg ttgcaacttt gcgtgggaat tcgtctacac tgtcatctat 360
ccttctcaaa atcccttcga gagagctgtc ctcacaacat ggatgg 406

<210> SEQ ID NO 264
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 264
cccagcccaa gacttgagta 20

<210> SEQ ID NO 265
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 265
ccatccatgt tgtgaggaca 20

<210> SEQ ID NO 266
<211> LENGTH: 39008
<212> TYPE: DNA
<213> ORGANISM: Penicillium coprobium PF1169

<400> SEQUENCE: 266
gccagccaat gtctcgacga gactctcggt gtcaagctgc ttgaggaggc cattgtgaag 60
atcgaagagc gtatcaggtc gcacggcggt agctgcaccg tgaagatggc acccaaggcc 120
gtcaccgagc aggacgatgc gatcctgcag gagcttatgg agaagcgcga acgtgagaac 180
acccaggtca gcggagatga ggactctgaa agtgatgagg gtgttcccga gtaagcgacg 240
ggctacaaat tcgagtcgag gggcatacag cggtcaccag cgctaaaatt caaagctggt 300
atcaccgcta gaggggagtt ggtgaaagat ggatagaaaa aacttgcaca tatcggaaaa 360
aaggctcgat gggccagtgt gctgatgggc aggattacag tcagaactcg cccaggtaag 420
tcgcctggac ttcggggtct ggatatgaca tattcacacc tgtgtatgcg gtattcccat 480
tgcggtcgaa atcctcgttc ccggcatcaa atacactggg tccgcacagg gtgcaagttc 540
tgatgcacat aatgtttgat gcaaccgata cgttcaatgc cagtcatgct tttagatgca 600
attatccctg tagaggccat gtagcaatgt atgtagcaat gtatgtagca atgtatatag 660
caatgtatgt agcaatgtat gtaagatatc ataacaatcg agctcatgaa atggcgggga 720
gagctgaagc ttatctaccg ccgccgatca ttggtgccct caaagccatc gagaacttcc 780
ctttcggcac ttctcttttt ccaccaactt tcattctacg cgatatggga cattgggcaa 840
agatctttac cgccgatcgt ggcaggaccc ggcatcgggt cgaggtggaa cgtcgtcggc 900
gtacgtcatt ttccaaacat gcggaacact actgacaagc cgcagtgcta ccggcctatg 960
cggccgatga gtctgacgcc tcggatgctt caaaggaaat tgcaaaggtt gctcttcggt 1020
tgaaatatca aattgagcag gttgtctcct gtgaagtgga ggagaacgtc ttgaccgacc 1080
caaacagccg tatcatcacg gatgatgtgg ttgcgactgc taagcaggcc ggtggagatg 1140
aatacaaagc atgcattgtt tattgtctcc tggtttgtct gcgatggttc aaaatccaat 1200
catccgtcga gctttgggat tccgatctcc atgagattcg agctgtggct tgcgaggtca 1260
tcgccaagcg catgtaatgc cccttttca ttccatgttc tcggccattt cctgacccaa 1320
acagtatcga atccgagcag aaccaagaat acgtgctaaa agacatttta ctcaagcgat 1380
actcaatctt cagtgaaggt gtggagactg atcccgccaa tgtcattgaa cgatcggtag 1440
atctccatgc tttaaggatc atcagctgtg ctgcgtacca gaagtgtatc cagtatctct 1500
ggagaggttg gatctgccag gaagaaggca acccaactaa ctttgtcgaa tacagtgaga 1560
agtcaaaccc caattattgg gttcatttcc atcctgatcg gatgcggact cctctgtatc 1620
agaatgtctg ccaaattttg ttttccttga tttaccttgc gacttatacc gcagttatca 1680
ataccgtgaa tcccaccggt gacctggatg tagctgaagc catactgtat gttatgactc 1740
tcgcgttcat ctgcgacgag gcggtcaaat tctggaaggt tggatggaat tatctcgaat 1800
tctggaatgc gttcaactca acgctctact ctatcctggc agtgtctctt gtcttgcgct 1860
ttattgcctt ggcacactca tcatctacgc acgatgaaac aaggcaggca tacaatgaac 1920
tcagctacaa cttcctcgcc tttgcgggcc ctatgttctg gatgcggatg atgctatatc 1980
ttgactcgtt ccgcttcttc ggtgccatgt tcgtggtcct tcgagtgatg atgaaagaaa 2040

-continued

```
gcttgatatt ctttgctctt ctattcgtgg ttatggctgg tttcttccag ggcttcgtcg   2100
gcatggccca agtggatgct gatatcccca tccaccgaaa tattctccag ggaatgatca   2160
atagtatcat gcaaagccct gagtttgaca cttttcagga atttgcattt ccctttggta   2220
tcatcctcta ttatgtgttc aacttcattg ttatgactgg taagtctgta ttacatttgt   2280
ttggggtgtc gctaaacatt tttagttctg ttgaatattc tcattgcctt gtacaacagc   2340
gcatatgaag atatctctgg caatgccacg gacgagttca tggccatctt cgcgcagaaa   2400
accatgcagt tcgtccgcgc cccagatgaa aatgtcttca tcccacgtac gtgtttactc   2460
aattctgata tagcatacgt atgactaact ttggtctggg taatagcctt caatctcatc   2520
gagattctct gtttgatagc tccattcgaa tggtggcttt cgcgggagac ttacgccaag   2580
gtgaatgaca ttgtaatggc cgtgatatat tctccgctgc ttgtcgttgc agcctgggtt   2640
gagacccgtc aggcgcataa gattcgatgg aatcgccgtc atggcgaaga agacgatgac   2700
tgcgctcagg aatgggagca tgtggccaag gaggtcaatt ttgatcttga cgatacctgg   2760
aaacagcacg taattgagtc cacgccggat atcaaggttg atagttgtac atatgaactc   2820
cgagagctga gggagcaggt taaaatgttg acggggatgg tgaaggaatt gactcaggag   2880
atggaaaaga aggcggatgg agcaagctag gaagtcctgt tgaattgtac agcaagaata   2940
ctacactgag catgggacat cgcaaaggtg atttgctact gcagtttcac caatattaca   3000
ttgcgaaaac tgtatattct cttaatgtct aatagcagca atcagcccag tggcacggag   3060
gaaagtcacc gtcctgtaag gcaaatactt gtgcttcaaa tgaattttga ctatttttca   3120
tgcgataact ggcaaagggc agggggagaa aaaatgatca ttattcaacc caagcaaact   3180
gtccagaaag tgacatgccc actttgcaag taaagaagat atgtgacaat ctaacagtct   3240
caggtagaca ttcgctcttc attaaaatcc atgcgttgct cgccgtagcc caattcgaag   3300
cactgggcaa cccacatcga gaccttaaaa tcgggtgatc atcacacagc aacaggctca   3360
gcaagaatgg aggcaatcgt ctccctttga tgatccagct gtgagagctt cgctcgatgg   3420
tgcttgccaa tacctatccg aggaatgtca tccacaaata caacacctcc atctagggct   3480
ttatagctgg ccagttggct ttgaatcaga cctgccactt gatcggccgt cgtctccggg   3540
gacgtatcat tgcggacgac ataagctcga ggaacctcgc tgctgccatc tgggagcatg   3600
actccgatca cggctgcgtc cttgatactc gggtccttgc gtaggatccc ttcaatctct   3660
gcgggagcga cggagtatct aaatcaagca cgatatgtta gtctatcatc tgctgcatcg   3720
gatgtcatat ggagaggaaa gaaagcgaag gatgtgaagg atgaagccta gaggactggg   3780
taacttgccc tcgaactttg atgagatctt tggtccgtcc gatgacatgg tagtttccgt   3840
cttccacatg gaacatgtct ccagtccgga accatccttg ctcatctttg gcatcagttc   3900
gtcctttgta tgctagaagg agtcccggtc cacggacata caactctcca ggggagtctg   3960
gtgtcccggc gacatcttcg cccgtgtcgg gattgacaaa gcgcagctca tatctgggca   4020
aaagagtccc tacactgcca aattgtggtt gtatcccgta gcgattctgg aaaaccactc   4080
caacctcaga catgccccac agatttcccg ctatagcgtc cggtgatagc aggctctgga   4140
attgctgcat agagtacccg tctatgggag cacccgaaat accgatatag cgcagagaag   4200
acaagctctc ggctacattc aaggaggacc tattgagaat gtggatcatg gcaggaacca   4260
tgtacgtttc cgtgatgtgg tgctggcgga tgccgtcgag caaagcggtg atttcgaagc   4320
gcgggataat gtacagaggc tggccgtacc gaatggggaa gatgttgccc cagaagtcgc   4380
caaaagaatg gtacagtggc agtgccatca aacgaacgac ggggtatggc acttcatagt   4440
```

```
agacgctcag atggtgggaa atgatcgtgt ggtgggttcg aattgcggct ttggggagac   4500
cgctggtgcc actggttagg aacatagccg ccggcgtgat cttgctctcc tcgctatctt   4560
cgaaacgaag ccaatccaac tcgccatact ggagcagact ctccaggcgg ataggttggt   4620
ccactgtctg ggtgtcgaga tcctccgtct gctccgcctg gccatgtgca aattggacta   4680
cactttcgat agacttctca tccatcagaa ggacttggtt tgaggacatt ccttgattat   4740
tgcaaacttc caggactctg gtcagcgcac tcggagcagt aataatcaac cgaggctcgg   4800
cgacacgaag cagatgagcc acttcatggg ggcgactagc gacatcaaac cccatataca   4860
ctccgcccgc accaacgatg gcaaagaaaa gagcagagtg tagaacctag gctgatgtta   4920
gcagcatatc attgttatgg ggtagtgtga ttacactgtt ctccagttgc acgagtacac   4980
aatcgcctcg ttccacaccc cgggctttga ggcccgcaat gagtgatcgc accagccgtc   5040
ggaattggat ggcattgaaa gcacgcgaag ggttgcgggc atcaatatag atgggcttag   5100
attggtcaaa ggcaggacca ctaaaagcaa agctgactag gtctgtctcg tgctccatat   5160
cgatgcttat attgtacagt tctcgtgtgc tattgacatg cagaacttga tgcaggattt   5220
gtgctcactt taagtagtag tacatggaat gctcagacct cccatatcac tttgatcgac   5280
actgcacggg acaagtatca tgcagaagac tattgagaag aatgccacgc caccaattcg   5340
tattatacta atctagccta agccaataca tgtaaagagt actatttagg acccacactg   5400
tcattgcaga gctttgaagc agctgcatgc gctaattcac ccacagatac gccactaaga   5460
atcaaaatta ccccgatgtc gacgctcagc tctttcgtaa accattgact cagcccaatg   5520
gcgataagcg agtcaatccc gagctcagga atcagcgtgt cagcagagag cggtgcatcc   5580
tcggccaagt tcaagctggc ccgaattttc tccattagtg gtctcacgac tgcttcggct   5640
ttttcttcca agcttgtcgc tgcagtgaca agatctttgg tcgaccgggt ctcaatcaat   5700
gcaagtattt gatcttgaga cgccgtggcc gtataggagt agaatggcca taacttcggt   5760
atcgggcact cgccatagcc acacttcaaa ctctggtgtc ggagtccccc gattaactca   5820
gcgttggaat tggaatctga gcgcccgcag aggattgcct cggcgagtat ctcgtcgaca   5880
tcccgctggg atacagctac cgggccacac caaagaggct gactgggaga aggactagaa   5940
atgccgtgga tctcgcccag atgtactaga cttgctggtc tgccctgggc tcgacggtgg   6000
cggaccagca gggccatttt ctcggacatc gctgcagtca ttgcctggtc cgcatggcct   6060
aacactcctg caatagatcc gatgagcacc caaaagtcca gagttggggt cttgtagagc   6120
tcatctagct gctgcagccc cttcaagacc ggatgcagat ggttccggag ggaatctatc   6180
gtgagctggg acaaggaaca gtcaggtaga ggcggaggct gaattagaac tcctcccact   6240
accgggggga acgcataggg aatagtttga tgcaaactgg tggcagaaat gccatcgatc   6300
aggtttctgg cattgattag cttgtgcatt tgaattcatg ggtacgtaag taacttacat   6360
tttcgagacc gctatgcgcg ttccccgtcg agaaacttct tccaaccacc acgcatctga   6420
gtcaagtcta gagccagcaa ggaggatcca ttttgccccg tgtgttgcta gccaaagaca   6480
gatagcatgg gctagttcac tgcctagacc tacaagtatg taggtttttt tctctgacag   6540
ctgcacctgg gaaccagcag tcggtatctg ggcgagcacc ggagttgtag agtcccaatc   6600
taccacggca tcctgggagt caaggattgg gtactcggaa atcctgctga ttggtaacga   6660
gtccacagaa tttggtggga gcccctcgcg gccggtgtac gccactaagc aggcggttag   6720
gaaagccttg gctatgagtg acgaatcatc cgcgttgatc ggccctgtcg atgcagaggt   6780
```

```
aaggtagaaa tcctgcaaat ggattcgtgt cgcgttgtca ggcaagagcg atagcatgcg   6840
atcatagaca ccctgtccac gacgatgtag aatcgctatg gccgacacat ctgagggaag   6900
tacctgagac aattgccgcg cagtgctatg ctcgtgcaaa agcaacatcg gtctttcttt   6960
gtctgggttg cttttgctag tgctgaagat aaccttacca tcccgccggg tcagcatttg   7020
gtggaaaaca gactgaagga ccccatcagc ctcgtgcact acaagcgtgc ctgattgtgg   7080
gacttgttcg accaggtatc ctgccaacag agcagccgct gtggcgcgga gataagactg   7140
ctcgtgggct tccaacaccg tgtctggcac tgaccacgcc caggagtctg gaacgataac   7200
atgagatgca atgtgggacg acagagcgat cattctcttg ttgctcttaa cgtccagccc   7260
tatgaccagc cgcagaaata tggcccctgc aacccgcacg gctgctatac tggaatgtcg   7320
aactcgcaga tgaagggttg ggccataact tgcggttatc ggcggatcag ccatcgaaag   7380
aaggcggaac ccttcacaag tcttgtcggt cgtagcagga aggatttgta caactccctt   7440
gtcgaggtcc acgcagtctg tcactttttg ccgcctggct agatggcgca gcccagtagc   7500
atggtcgtga tattgccgag gaacacggaa catagagccg tcgtattgaa tttcgggctc   7560
gatgttggtg agtccgcacg aatgaggatt ttcttgagct gcactagctt gaacaaagtg   7620
tccaagagct gtcgccaata tttccgttgt aactccaacc ggatctgtga tatgtagcag   7680
ttgtagcaga gaagacgatc gttcagaagc caggaaggtg gaaaggagac ctttcaccag   7740
tccggcatca gggtggtcga ccttctcaca ggtcaccact aacattcgct tactgactgt   7800
catcagtctg cacaactcgc tcaaggtagc gtttgtcaga tctcgatcat cgacgaggta   7860
cagaacagtc aatttagata aatcgcgatc ttcaatgaga tctaggtctg gcgcatgagc   7920
aaccttgacg aagtcatcct gtaccaattc aaaaagctct gaggtaagac aatctgcctc   7980
ctcagcgtca ccgccaagca acagcaggtc tccgcggctc tgtggttccg caggactgtc   8040
tggagtgcga cagagaagga gtgaaaagtc cccaaggctt tcactctctt gggacgcatc   8100
gaacgaatcc aagccataga atccgccgtt agacagtagc tcaacccagt ccctcctggt   8160
agtaattggc tcaccagagc agtagccttt cccggtctct gtgcatctca ttggaggacc   8220
gaatagaaga ttcaaatatg tagtgctggg attcgttcgt actagtagga ccaagaatcc   8280
accaggcttg agcaagcgac gaacatgagc caccgcgacc tcttgcagaa ataccgcggc   8340
tgtgatcagc accatatcgt agaattgctc gcggcagccc tgctcgacag gatcctcatt   8400
gatgtccaac gttttgtgcg acacctcgcc aggttgctca aggtcttcct caatcgcttg   8460
taggccagaa acggagagtc cagcataagt aaatgaccga taagtccgac ccatcttctt   8520
cagtccagag tgaacatggc ctccaaattg gccgatctga aggatattca tttgtggaaa   8580
gcggaaacac gcctggctga cgacagatac gagctcgtct tctagatcca agacttgcaa   8640
gtcctccttc agatattgac tttcctcatc gatggccggc caggcctcta tttgaagacc   8700
agaatcacgc agaacgcgag gtagccgctg gcctaccgca gcaatggccg tgagaccagg   8760
gtcattcaag agtgacgggc tcactccagc tgtgaagtcc tcaatcttct ggtccaagca   8820
ctcggattcc ccgacagggt ctggctcttg gctagcattt gcaatgcatt ggttcatcca   8880
tgcaagcaga cgagcaccat cgaaatccaa tccgcttcgc tccaagtccg tcagtccatt   8940
gcgagcctgc ttgagataca gtagcgcaag ctcctctcgg agagagtgta gctgtagcat   9000
ggtagctggc aacttccgtg atcccttctt cagagtgggc tcaagcggtc cccacgcggt   9060
ctgggaaaga acctgcaagt tgtttggtgc agttccagat ggctggcata tgagagaaac   9120
accttcgagc tggacagcct tttccccatt catggtgaag atgtcaatat caccgcgaat   9180
```

```
tcgatctcca ttaacgcagg tcagatagct tgctaccgtc aattccttgc cttgccaatc   9240
tgaagcacat aacaccggat ttatccaggt actgtcaaca tttctcgata agaatggtcc   9300
cgtcagcagc gtctcttcaa gcccaccaat tgcagcaatc attgtttgaa caccaaggtc   9360
caaaatagcc gggtgaagag ccatgggctc atccgaatca tttgagggaa cgggcacact   9420
cccagtggct agatcacgcc ttttgcggag tcccgtcaag gtagagaatg ggccagtaca   9480
gtggtagtca gcgcggcgca ggctgtcata gaattcagtg ctgtccacgg gctccaaggc   9540
ctgaggtagc tgtccctgtg gggtaggag agcacggtca gaatcccctg gatgcatgat   9600
catcttggct gttgcacact gaacgagctc tccggataca acagcttcgc agcagaacca   9660
agcagtaatg gctccatcat gcgagtgaat actacccacg gtgacaagca cttcagtgcc   9720
gatgggatca ttctgaatcg ggagctgagt gtggatggtc aagtccttga cattcaacaa   9780
gcgtaggcct tgtgtctgtg ccattatcat acctgcctcc agtgccatcg atatgtatcc   9840
tgtctcaggg aagacagatc ccgaatcggc acgacggtcg gccaaccagg gcagctcctc   9900
tggtcgtaga tagtttcgcc aacggaactt ttctgctccg gtctctggac tgagagaacc   9960
gagaagtgcg ttaggagatg tagcacgatg gttatggttc gaagacattc gcgactgtgt  10020
ccagtatgtc tgagtatggt cgaaggggta gaatggtagc gattctacca acacaggcca  10080
atgatttgga tcaaagagtg agacatagtc tgtgaggcgg acgacatttg ggccgaggtg  10140
tgcccaggaa gatcctaggg ccgttgccca tgtatcgagg ccgggctttc ctcgctcagc  10200
aagagcaagg taaggaattg ccgagtgggc cgagtgcatt ttggagaggg tctgtaggac  10260
aggccctctc agtgtcggat ggggcccgat ctcaatgatg agatctggtg gcccagcgtc  10320
tcgtgccgcg gcctctaggg cttgggaaaa ctgaacagga cgcagcatat tctcaaccca  10380
gtactcccct gtcaattcct gctggtcata cccagtcatg acctcccctg ggtagacact  10440
cgagtaccag cgcgaggcag aagctgacag ggcgacagga tacgctttca ttgcgtcacg  10500
atatggatct gcacaaggct tcatatgcgg agagtgatat gcggtgtcca ctcgaagcat  10560
acgcggagtg aggcccaggc tcttcagcag ccactccagc tcccgcaggc actctgcgtc  10620
gccggataac gtgacgctgg atggcgagtt ggcggcagca acgcttatac gtccggagta  10680
ggcttctaaa gcacagatat tctgcgcctg ctgccatgtc aaattcacgg ccatcatccg  10740
acctgtcgga tcgcgtgact tatcaatggt catcccccta aggtacgcga tgcggattgc  10800
atccgaggcc gtcagcacac ccgcagcata ggctgctaca atctcgccgg aagagtgacc  10860
gaccacaatg gtaagctcaa tccctaccgc acggagcatg ttgacttgca tgatttgcaa  10920
cgctgtccgt agggggagag aaaggaggcc ctcgtttacg cgcgaggacg atgccggctg  10980
tgacaactcg tcgagaagag aaaactgtgg acgaaggtct agtggaagct catccaaagc  11040
ttcctccaga ttcataatcc attttcgaat tgagggactt gcctcaatca gatcaagtcc  11100
catttgtggc cattggactc cttggcccgt gaagatgccc atgacgcgtc tgggccgagt  11160
gttggatctg gagacgacag aggctggttt acccgtgacc cttcgactta tttctgtatt  11220
gatctggtct ttcaactctt gtattgagtg tgccattagc gtcaaccggt ggcgatgagt  11280
ggaacgtcga tcccacaaag agagcgccag accaacgaga ctgactgttg cgtgttcctg  11340
gaggaatgtt gcgtatgatt ccatcacaca agtgagggtc cgctcagacg cagcagaaaa  11400
gacaaagggc agactggagg gtatgttgtt ggacggactg agctccgagc gagtgtagct  11460
ttctaggacg acatgcacat tggcaccccc gaatccaaag gagttcaccg aggctcgacg  11520
```

aggacagcca tctgggactg caggccacgg gatgcattct gtggggacag aaagcttggc 11580
ggcaaacggt ttaatttttg gattgagatg ctgcatcagg agattaggag caatcatccc 11640
gtgttgcagc gagagggatg ccttgatcaa tcccgctagt ccagcagtgg cctctgtatg 11700
tccaattatt gtcttaattg acccaacata cagccgatcg gtcgaatctg gaacggattc 11760
gggcccaaag aagcttgagt tgattgcggc tgcttcctgc ggatctccgg cctgggttcc 11820
cgtgccatga gcctcgaagt actggcaccg atcttccggg ttgttttgag gagagagccc 11880
cgcgcgtgca taggttgcga ggatcaatga ttgttgtgcc tttggattag gcatcgtgat 11940
ccccatagtt cgcccatccg agtttgcccc tgaggcacgg atcacgcatt cgataggatc 12000
tccatcatta atcgcgtcct gcagacgttt tagtacaacc gaagccacac cctcgccacg 12060
tccgtagccg tcggccttgc tgtcccacat tctactccgg ccggtagggg acagcatccg 12120
tgttttagaa tccgcaatat aggcattggg agacaggatc aggttgcttc ctactgccac 12180
tgccatggaa cagtcatcgt tctgcagagc ctcgactccc agatgaacag ccaagagact 12240
cgaagaacat ccggtgtcaa cggccataga aggaccttgc cagtcaaagt agtaagagat 12300
acgattggcc atgattgacg gtgagtttcc cgtaaccaca tacgcgggga acgcctgagg 12360
atccatggcc tggatttgat tgtaatcgtt gcgaagtgta ccgcagaaca ccccggtctt 12420
tgagcgctgc agcgcatcca tccgtaaccc ggccgcatcg agcgattcgt acacggtctc 12480
taggagcaat cgctgttgtg gatccattgc taccgcttca gttggcgaga tattgaagaa 12540
ggccgcatca aaggctttga tgtcctcgtc caagaagtat gactctttga cgtttgttgt 12600
gccatggtgg tctccatctg gatgataaaa ggcatctata ttgaatctgt cggccggaac 12660
tttgcgcgcg atatcccgag ggctttgaag aagctcccac agtttcgaag gagaggaagc 12720
gccaccggga aagcggcatc ctgtaccaat aatagcaaca ggctctgttg ctttcattgt 12780
gagattataa gagaggtgta aaacctgaga tcaaaataat ttgcagttgg gtggctgtag 12840
ctctactgag agtacgttca tagatataag caatgcagtg ttgccttact tacttccacg 12900
atcttgtcag catatctatc gaacgaatag caaaactgga cctatagagc aatttccggc 12960
catcgataga tcattggata gctgtcctat ttgggaagta tgatctacaa tttatgcagc 13020
cacaaactat acaaagtggt ccatcgccag atttggcgat gagcagcggt gtggaatagt 13080
gactttgatg aacatgtcag gtcctgcatc tacatgtgca ggtgtccaag gatgctcctt 13140
gcgcgaagaa gtggagtagg gacattcagc tacctcctta tcttttccct tcttttaatg 13200
ctcactctgt gcataataat agtggcgaat atcgaagcat cgaaatccaa cgacattgag 13260
acaacatgga taacatggac aacatgaaca acacaccttt aggtttcaac tgggcctggg 13320
cagtcatcat ctctttcctg ggtctgctga ctttttcctt tgtctcgcca cacctctttc 13380
cttcaagatt gacggtgatt aatggtggaa gagcctggga tatctttcgt accaaggcca 13440
aaaagcgatt tcgctcggac gcagcacgtc ttataaagaa cggcttcgag gaggtgagta 13500
tggaaaaact gcatcattta ggataaagtg ctaaacgttc cttcttactc cagtctcctg 13560
atgcctttcg cattatcacg gataacggtc ctttgctggt cttgtcacct caatacgctc 13620
gtgaggttcg cagcgatgat agactcagcc ttgaccattt cattgcctcg gtttgtcttg 13680
cttcatgtcc aacgttttc tagttggcgt cgctaagctt ctactgttta ggaatttcac 13740
cccaacatcc caggtttcga gccgttcaaa ttgatcttgg atccaaagaa cccgttgaac 13800
acgatcctca agtccaatct cacacaagca ctgggtactg acatcgtcct ctccgctctt 13860
atgcagccca ttacatagct aacattgttt acctggatag cttatctgac agaggacttg 13920

```
tctgcggagg taacagaggc actatctgca acctgtaccg atgaccctgg taagctataa  13980
aacatggttt tccaaaggtt ctggtatcaa tactaacttt ctttcttctc ttaatcaaag  14040
agtggcacga ggtcagcgtt agtcaaacgg ctctcaaaat tatcgcacaa atggcgtcca  14100
aagccttcat tggacaagaa agatgccggg atgccaagtg gcataacatt atcatcacgt  14160
acacgcacaa cgtctatgga gcagcacagg cactccactt ttggcccagt ttcctacgac  14220
ccatagtggc acagtttttg ccagcatgcc gaactttgca ggctcagatt gctgaagcgc  14280
gagagatctt ggagccattg gtagcccaga gacgagccga gagagccacc cgagccgctc  14340
aggagaagcc tcatccgtct ggtggggata tcattgactg gctggaacag ttttatgggg  14400
accaaccgta tgatcccgtg gccgcacagc tactgctctc atttgctgct atccatggaa  14460
cttccaatct cctggcgcaa gcgctcatag atctctgtgg ccaaccggag ctagtacagg  14520
atctccggga agaagctgtg tccgtgctgg gtaaagaggg atggaccagg gccgccttgt  14580
accaactcaa actaatggac agcgccctga aagaaagcca gcggttggcg ccaaacagat  14640
tgtgtgagtg ggcccttcct cttgcccccc aatttgacca ttcaactggc cattagagac  14700
taattcaggt gtgcttttac agtatcgatg ggacgcattg cgcaaggcga tatggacctg  14760
tctgatggtc tccgtatcca ccggggcacg accctcatgg tgtctgccca caacatgtgg  14820
gatcctgaaa tctaccctga tccccgaaaa tacgatggct accgattcca taagttgcga  14880
caaacatcag ggcaagaggg ccagcaccaa ctcgtatcct cgacgccgga tcacatggga  14940
ttcggatacg gaaagcatgc ttgcccggga cggtttttcg ccgcagccca gatcaaagtt  15000
gcattgtgca atatcctcct caagtatgat attgaataca ggggtggcaa gtccccaggt  15060
gtgtggggtc agggcataca tctgtttccc gatccgacgt ctaggatcca cgtccgtcgt  15120
cggaaagagg agattaactt gtgatactat tgtctaacta tgcggatgtg gttgaatgca  15180
aggactctct ctctctctct gtctgattga tatttgagtt ttctatggtg atcgagcaag  15240
atttttgcaa tgtggagccc atgcatgctc atgaggccta ttgggccgat ctcttcgaga  15300
tcgtgatcga gagcaaattt gagaacctca gaccttgttt atttgaaagt agcagatgaa  15360
caatagaatt gtttttactt ttggaatggt tccacaataa tcctagtcta gatttaagat  15420
accaatattg aagtgttatg tttgcatgta tcttcagctg ctccacccgc gtggagtgat  15480
tattagctta ttagcgcctt ctcattaata cgccctccag ttccagcctc tcaaaagtaa  15540
tatgctggaa tgatagaggt aattggctaa tggcctcaag gcaaccctgc agatagtgaa  15600
gcaaaagcaa taaatattca atattcacac ataatttgac atacggagta ctccgtactc  15660
cgtttaagat cgggcatagt attggatgat gttagaatat atcttggcaa ggtgacatat  15720
acaatgtact ccgtatgttg tacagtgtca atggctttgt ggagctgaag atgcggtgat  15780
ttcttttcct gatgcatcat caagtccgga aaattgatga aaatctacga gtacctcgag  15840
ggatgaactt ccctgcacag atcatgacat acatataaac tattgatcca cttgcattag  15900
cgggagtcta gcaagagcaa gtctatgtat tccctacatg gtcgaggagg taagttcggg  15960
ctgaaaaata cgatgcagca tacactaccc ttacaactag ctgtttaatc agaaaaagca  16020
aatagaaatt agggcacaat ttactcttta ctgccaaccc cccgtcgtaa cccttgctgc  16080
tagcattgat tggctgtcag tcgtacaacg aagaaacgac actgtctgtg attatattct  16140
attccatcac aaacgtagcc cggagtgccc ttcccagagt ccttgtcttg tacaccgtgc  16200
ttgtcttagc attttcatta tgatcgagct caaagatgct tcgatggggg ctgtattgct  16260
```

```
gacatgcgtc cttgtgcttg caggcctata tctcattcga ttgacgttat caagcgacca  16320
attggacaag tttcctagca tcaatcctcg gaagccctgg gaaatcgtca atgtcttcgc  16380
ccaaagaaga tttcaacagg atggccctag gtatctggaa gctgggtatg caaaggtgtg  16440
ttccataagc aactgctcca aaaggcgaat aaggctgaaa gttactacag tcccccatct  16500
ttagcgtggt caccgacctg ggccaaaat tagtggtttc gggtgcattc atcgaggaat  16560
tcaaggatga aaagctgttg gaccattatc ggtcaatgat cgaggtttgt acgacgttag  16620
tgattatgaa agagcaagcg cttacttgtg caaggacttc atggcagagg tacctggttt  16680
tgagtcgatg ttcctgggga atctacacaa tacggtactt cgcgatgtga tttctgtcat  16740
cactcgcgaa ctaggtaaat attctttcct tttgactgtc cggttatccg ctgagttcta  16800
attttataga acaactgcta gcacctctct cggatgaagt atcagcggct ctggtagata  16860
cttggacgga ctcaccaggt gggtcaaagc acacttccca atagaaatca ggaggaaata  16920
aaaactaata tcaatataga ctggcatgag gtagcactgc ttccaagcat gctgggcttg  16980
atcgcaaagg tttcatctct cgtcttcgtg ggtgaaccgt tgtgccgcca cccagtctgg  17040
ttggagacag tgatcaactt caccctcatt cgacacaacg caatcttagc cctccaccag  17100
tgccctgctg tacttcggcc cgtccttcac tgggttcttc caccatgcca gaaactccga  17160
cgagagatca gaactgcacg gacactgatc gactctgctc tggaaaaatc aagaaagaat  17220
ccgcagaccg agaaattttc cagcgttgcc tgggttgatg cttttgccaa aggcaacaag  17280
tataatgcag ccatggtgca gttaagactg gcaaatgcgt ccatccactc cagcgccgat  17340
ctcctggtca agattcttat caatctatgc gagcagccag aattgattcg ggacctccgg  17400
gacgagatta tctctgttct tggggagaat ggatggcgat cctcgacact gaaccaatta  17460
aagctccttg atagtgttct gaaggagagc cagcggttgc atccagtcac aaccggtatg  17520
catcgtcggc tgttcaaact gcgtgcccag tgcatatgct gaccatttac tttaggagca  17580
ttttcgcgct ttactcggca agatatcaag ttgaccaatg gcactgagat tccttcagga  17640
acacccatta tggtcactaa tgatgtcgcc ggggatgcca gtatctatga tgatcccgat  17700
gtcttcgatg ggtatcggta cttcagaatg cgtgaaggag ccgataaggc ccgggcacca  17760
ttcacaacga cgggccaaaa tcaccttggg tttgggtacg ggaagtatgc ttgtcctggt  17820
cgattctttg ctgctaccga gattaagata gcgctctgcc atatgttgtt gaagtatgaa  17880
tggaggctag taaaggacag gccgcatggg atagttacaa gcgggttcgc agcattccgt  17940
gacccacgag caagcataga agtccgcaga cgcgcggtgg cgggagaaga gctcgaggta  18000
ttgactggaa agaagtgatc tagggaaaat tacgaactca tagtatgagc aaccataccc  18060
aaaacaaaga gacttaccaa ccccatcatc aaggtagact ggggattttg actatgtcga  18120
tgtaaatcgg tcaacagcct tattaggata tataaattat acgcttctca ggctttaaag  18180
catcacccag cacgataatt tctctggatt attgcaaaac caagaaattc tctgatccac  18240
agctgtatac tccgtactcc gttcatcatc ttacagtcat gcagagggtg aaaggggtca  18300
gtgtgtgacg gtatttcggt atctcgcctc gtaatttgac agatccagcg ttaaacccag  18360
cccaagactt gagtagacta tatttattct ctttgatatc catctcagca tcaagttttt  18420
gacgttgtat tactatcctc gtttggaatt ctcctcccag gtcttgcttc attgcttata  18480
gcattctacc aaaaacgtca ctgtcatgga cgggtggtca gacatatcat cagcgcctgc  18540
cggatacaag gatgttgttt ggatagcaga tcgggctctg ctagcccaag gattgggatg  18600
gtcaatcaac tacctggcca tgatatacca atcgcgcaaa gaccgcacat acggcatggc  18660
```

```
cattttgcca ctatgttgca actttgcgtg ggaattcgtc tacactgtca tctatccttc  18720
tcaaaatccc ttcgagagag ctgtcctcac aacatggatg gtcctgaacc tctacctcat  18780
gtacactacc atcaaattcg ctcccaacga atggcagcac gccccgctcg tccagcgaat  18840
tcttccagtg atattccctg tggcaatcgc ggcatttacg gcggggcatc tcgccttggc  18900
tgcgacagtg ggagtggcca aggcagtcaa ctggagcgcc tttctgtgct ttgagctatt  18960
gactgccggt gccgtgtgcc agctcatgag tcggggatct agcagagggg cgtcgtatac  19020
aatctggtat gttctttttg ccttgtggat cttgcttggg tttattggct aatgtgaatt  19080
gtggttggca gggtctcaag atttctgggc tcgtatatcg gtagtatctt tatgcatgtt  19140
cgagagaccc actggccgca ggagtttgac tggatcagct accctttcgt ggcgtggcat  19200
ggcatcatgt gcttctcgct ggatatttct tatgtgggct tactgtggta cattcgtcgg  19260
caggagcgcc agggccaatt gaagaaagct atgtgatcga caggaccatg catgatggag  19320
gtccgcacta acctcaactg tactttgtac aggtctgagt gctatatgac gatagtcaca  19380
aaacagagtt ggaggttatt tgcgcacatt gactaaaaat gggagagctg atggatatat  19440
gcaaggggga tcaggtctcg atctgatcgt gccgatcgac aagaacaatg ctttgtctgg  19500
gcgggtccaa ttgtctagcc tagaagtcta aatttcaatt ttcttcggac tttttacata  19560
gtaactactg cctaggactc gggatatgaa gtataatggc gagaaatggc tggctgcagg  19620
ggacatacag gtgataattt gccctcgatc tggcagctag ttacgtcaat atcttgttag  19680
taaacaccag ttgtagatct ttgcgtatat atgaaactca aaagcatttg tgtctactcc  19740
gtaattacct tcccaacccc tccagtgcca ttgaaaccat gaaggtcatc attgtcggag  19800
ggtccatcgc gggtctcgcc ctcgcccatt gcttggacaa ggccaacatt gactatgtca  19860
ttctagaaaa gaagaaagaa attgcccccc aggaaggtgc ttccattggt atcatgccta  19920
atggtggtcg gatcctggaa cagcttgggt tatacgacca gatcgaggag ctgatcgagc  19980
ctttggtgag ggcgcatgta acttaccccg acggcttcaa ctatacaagt cgataccctg  20040
cactcataca gcagcggtgc gtcaatataa gctttctact ttctgatttg aaactaatgc  20100
gagaggtctt aggtttggct atccacttgc attcttggat cgacagaagt tactgcaaat  20160
tctggcaact cagccggtcc aatccagccg agtgaaacta gaccacaagg ttgagagcat  20220
tgaggtctcc ccatgtggcg tcacggtgat aacaagcaac ggacacacct atcagggcga  20280
tcttgtcgtc ggggctgatg gagtgcatag tcgggtacga gcggagatgt ggcgactggc  20340
agatgcctcg caggggaacg tatgtggaaa tggagacaaa ggtaacatta ttcctactgt  20400
tttgtcctat cctcgctttt ttttttcttg gccaagtgtt ttgactttga gctggaaagc  20460
taatatattg atttatagca tttacgatca actatgcctg catctttgga atttcgtcac  20520
acgtcgatca attggaccct ggcgagcaaa taacctgtta caatgatggg tggagtatcc  20580
ttagtgtgat cggacagaat ggcaggatct actggttcct ctttatcaag ctggaaaaag  20640
aattcgttta tgatggatca cacaaaaccc agctccactt tagccgtgaa gacgcccgag  20700
ctcattgcga gaggctggcg caggagcctc tctggaaaga tgtgacattt ggtcaggtct  20760
gggctcgatg tgaggtcttt caaatgacac ccttggaaga aggggtgctt ggcaaatggc  20820
actggagaaa cattatctgc atcggagaca gcatgcataa ggtcagcagc tcattatcac  20880
tcctggctta ctgacttttg taattaattg acattctcat gcagttcgca ccgcatattg  20940
gacagggtgc taattgcgct atcgaggatg cagctcagct cagcaatagt ttgcacactt  21000
```

```
ggctgagcgg atctggaaag gagcatcaac taaaaaccga tgatttgaca gagattctgg  21060
ctcaatttgc acaaactcgc ctccagaggc taggtccgac ggccatggcc gctcgatctg  21120
ctatgcgtct gcatgcgcgg gaagggctca aaaactggat actgggacgc tacttcttgc  21180
cctacgctgg tgacaagccg gccgactggg cctcccgagg aatcgcaggt gggaatactt  21240
tggacttcgt agagcctccc acgcgggctg gtcctggctg gattcagttc agccagtcgg  21300
gtaaaaggac ttcgtttccc atggcagtgg caggtctgtg cctagtgagc attgtggccc  21360
gaatcatgta tttgaaatta gttgcataga gaggcccacc atatctggag tacttcatac  21420
agagtgtttt atgggacaat ataaacttta gggcaattta gcgctttgat atagatcatc  21480
tgcatactag taaggcaacc ctgaaggtga tcgacacgat ctgcaaaaat caatatcgtg  21540
cttcgttacg gagtattgtt ttctacatgt catagtgcgc gctgccccag tggggctatg  21600
cagaaagtga tttcgatgta ttgctactta cagtgatgtg gtccagcatg tcagccattg  21660
ctctagtgcg tgcgtgtact gaccacatcg cggccattgc catttatcta gggtcctgtc  21720
gcctcaaaag cttgtggtca caaatcgttt gatccttcga gatcatactg aatttttgtt  21780
caatctgtca tcatggctgg ctctcagtct acggcgcagt tggctcgcct tctcattgat  21840
atctcccgat ttgacaaata caactgttta tttgctatat tccctggagg tacggagtag  21900
tgcagaccac ttcaacatta taccaccgcg ctcacaattt catatagtct ggtctatctt  21960
ccttgcagca gcctcacgac acgctgatgg cgaccccgtc cctctggact ttgtattggg  22020
ccgcgcagga ctggccttca tgtacacgta tatgctgagc ggcgcaggaa tggtatggaa  22080
cgactggatc gaccgcgata tcgatgccca ggtggcccgt accaagaatc ggcccctcgc  22140
ctccggtcgg ctttccacca gagctgccct catttggatg cttgtccagt acgcagcctc  22200
ggtctggctg atggaccgca tggtgagcgg gcaggatgtg tacgtctttt ttcctcctcg  22260
taccccaaac aattattctg ttgattgaaa actgacccta atcattctcc agatggacat  22320
acatgcttcc tctcacaacc gggattatct tgtatccctt cggcaagcga ccgacaagtc  22380
gcaagctggg cgtctatccg caatacatcc tcggtgcaag cagcgccctt actatcctcc  22440
cagcctgggc ctccgtctac acaggccgta tatctttgaa ggatctgggt atgcggtgtc  22500
tcccgctttg tctcttcctg tttctgtgga ccatctactt caacaccgcc tacagctatc  22560
aggatattaa ggatgactgt aagctgaatg tgaattcgtc gtacgtcctc gcggggagcc  22620
atgtgcgtgg aatgcttctg ttacaggcta ttgctgtggt gctggtgatc ccctggattc  22680
tctacaccag cgcctccact tggctctggg tctcatggct gggggtatgg acggcatctc  22740
tcggcgagca gctttatctc tttgatgtga aggatccgag tagcggtgga aaggttcatc  22800
ggcggaattt cgcactgggg atttggaatg tgctggcctg ctttgttgag ctgctatatg  22860
cttcaggctc tctgtgaatg atgttaatac gatgtggtcc ggatgagact tggggagtag  22920
agtctgagag gcttaaaatg ggtaaatggt gcgatgttgg cacagtgtga actattcata  22980
aatctttgct acgaagttgg gcttcacctt tcaattgaga agttgttact ggaatttttc  23040
gacactcaaa attcgaagag acttgtatta ttagagggat atagcctatg tcttccaatt  23100
ggtgtagaat cccaactacg agaccgcttc agaacgttgg agcacaagga tagaaagttc  23160
acctattcga aattctctac tgtcgtacat atgctatgta catgttactc ctttgcttgc  23220
gcacctatag cccagcaaaa caagggatcc tttgctaaca ggagctgatc atcacggttc  23280
agagtcagat gcaaatccca cggctccgta ctcgccacat catcctgacc ctttggaagg  23340
ataaagcaca tccccctaa gacaggcaaa tgtagttgga accctcgagg ttgcgctcca  23400
```

```
aggctctccc caaagtccag tccgaagatt tcaaaattcc taaagctgct cagagggata  23460
ggaactcccc gaaatccgat atccgcccag tcaggctgcg agtggagatg ggatagagcg  23520
tcttgaatat attctgcgtc aaccgccaaa agactctggc gtatacgagc tgcaatttgt  23580
gtgagatcct ccagacactc ctggcgcaat tccaccgaag gatctgtgcc atcaactagg  23640
gcctcgtttc tcccagcttg aattggcgta tatgtcaata gcaccatgtt tcccagatag  23700
tcatcaaagg ctggagtttt gaaattccca cgcatatcca ccgcgattga cagttcggta  23760
gatttaccag ccaattgtcc cgcttgccga agtatcatgg ccaaaagggc gctcacgatg  23820
tcgttactgg acaggaaccc tggactcggc ctaccatcag cctggaaaga cgtttgccct  23880
ttgatcaacg tattgcaagc ctccttcaaa tactcgatct taggaccggg gattttcagt  23940
cgccaggtga caagctcggt ggctctcgcc cggacgaagc ccgaccaatt ctttgcaagt  24000
agtgctgccc agtctccgag gccacagtag tgcttgctaa aatccatcct ggaaagaccg  24060
gagctgcttt ctgggacaag acgctcaatc tccgatcgta actgccgatc tggcgacaca  24120
cttgcagaag acatcgccgt cgggtctctg cagcaatcgg ctagaaggcc caagactcgc  24180
gcagcgcctg caccatccat tgcggaatga tgaaacgtca tggcgagaat gatcccatcg  24240
cgcatgacat ttgcttgaaa tcgtaggatc ggccttcgtg gcaacgaaat atccatgtcg  24300
ataggcaatg gcgccagccg acttatgatt tcctgctcct cagtgcccgt taggaggcat  24360
tttgattgga tttccttgaa tgactcggcc tggtagtgcc gtatccggag tatagggaac  24420
tggacaagcg actctgaggc ttctggttcg atttgccagg tgtacttcgt ttggctggac  24480
tctgtccgcc gagtcacgtc ccctgcgagg aaggggtgta ccttcaatag cagctcgatg  24540
ccattctcga gaacaccaat gctcttctca ggttgcgtgg tctggaaaaa cagcagaaag  24600
gtgacgttca ttccgagggg attgtggtcg agagaagata aagggtaagc agagcggtcg  24660
ccagttcttc gggcatcgca cattccatct tcacatagac cgtggagtct cacaggtccc  24720
tctttgacct gatctctttg actgactggg agacatactt cctgggtgct catgatttct  24780
gggtgttatc ctattgagtt gagttgtgtc ttgatctttt tttttatttt ttttggattt  24840
ctgaccttgt ttcgcttata ttggactttg cttttctttg tatattgtat tgcattaccg  24900
tacaacaaag catgggattc tctgtgttct gcatgattgt ggagcgtatt ttcctcgatt  24960
tggtatacaa tcaggtcgat ccctggcgga ttccggatct gatgcatgta tacaggtcat  25020
atatctgctt tcctcggtat ttttgagctg aatatcacta tatatgcttt ggagacgatc  25080
aatcgcaaga gagggttagt gattaaatca gttagtctca tccatagtgg gcattagagc  25140
caataaaaga tggtttccac cttgagatgt gatcgccaca agaagatttt gtaaatagta  25200
tgtattttcc aggccctgat ttctatctgc atatttgtca gcttgatcta cggagtacat  25260
cttactgctt ttagatactg acagcagcaa aactccgcgt tgaaggacga gctttgacac  25320
aaggtcaggc acttctctag tacacaaatc ctaatcatcc gacgacatac tactccgtat  25380
gctgtacata gagatccatg tccaattctt gagtctgccc ctctttgatc cacagtccag  25440
ctcagccagg cgcaatctgc atgcattggc atggaagcta ggagctgaca ttggctggaa  25500
ctacgccatc tggggcacaa tgcaagctag gcaactgacc atgtactggg tcagttttga  25560
ttgagtatgc tatacggaag aaagcgacta gtactccgta ggtttgtgta ctacctgcaa  25620
gtggaaagag atacctagat aggtgacatt agtgtccgaa ccaatgacca atggccctta  25680
tgcacccata tcccttacat ctttcagaaa gagaaaagcc acaagtatat catgtactcc  25740
```

```
gtactccgta caacggaatt acttgatctc tatattacct tcttcctgaa gaccgtttct  25800
cgctattgtc agttacacac acaatggatt ccctattgac gagcccgtta tggctcaaaa  25860
ttgcacatga gctagcactt tacctctctt ttattgtgcc aaccgccttt ctcatcataa  25920
caactcaaaa atcatccatt attcgatggg cctggacacc atgtctgctt tatatcctgt  25980
accaattctc tcttcgggta ccctctctgt cgacaagtca attcttgaag ggcgttgcag  26040
cgggtcaagc aaccgtggct gctttgcaat gccttaatct tcttctgatc acgaagctgg  26100
accaaacgga tctgctacgg gcaaatctat acagtccgtc tgcaggactg ctttctcgcc  26160
ttgctcaatc ctgcgcattg ctggtcaact tccgcggaat cggcacaatc tgggaggtta  26220
gaaacattcc ccagcacgca gcgtttgtcc aaccaaaagg caaggatcaa tcaatgagcc  26280
ggaagcggtt tgtcttgcgg gaaattgcaa tcattgtatg gcagtacctg ctccttgatt  26340
tcatttacga gtcaaccaag ggcacgtcag ccgaggattt gatgcgtctc tttggccctg  26400
gtatggaaat caagtatctc gatgcaacgt tcgaacaatg gatggggcgc ctctccgtgg  26460
gaatattctc ttggcttgta ccttcccgag tctgtcttaa tatcacttcc cgcctgtact  26520
ttctcatctt ggtagtattg ggcatttctt cgcccgagtc ttgtcgaccg ggcttcggca  26580
gagtgcggga tgtatgcacc atccgtggag tctgggggta agtgaactat tccgactgct  26640
ttcattcatt cactaacgcc accacagcaa gttctggcat caatcctttc gttggccact  26700
cacctctgtc ggaaactata tcgcaagaga cgtcctcgga cttgctcatc cctctctttt  26760
ggaacgctac accaatatct tctttacctt tttcacatcc ggcgtattgc accttgtctg  26820
tgatgctatt ctcggcgtcc cgccatctgc gtccggcgcc atgcagttct tctgctcgtt  26880
tccgcttgct attatgattg aggatggggt tcaagaaatc tggcggagag cgacgggcca  26940
aaccaaggac agtgatcgtg cagtaccgtt ctggcagagg ctcgtgggat atctttgggt  27000
ggctgtctgg atgtgtgtca catctccgtt ctacttgtac ccagctgcgc ggcaacatgc  27060
ggagaagaac tggatagtgc cattcagtat agtggaagaa attggccttg gaactgcgca  27120
aaagattttg ctgggttatg gcttgtttgt gtactgggcg gttggtgggg agatttaaat  27180
tcatgtgtcg ggattgttca tcgtggtcaa cactgtttag attgtgatat atattttcac  27240
cgaacacccc agaaacaaaa gatttaagcc ccaattaact accttgaagg gctcatgaga  27300
tttgatcaat gtagcaaccg tcagtatcct aggtcgtgat tcccccagcc agagcgagat  27360
aattttccag acatcatctt atctacatgc aaccaaaaac tccctggcat atattaacag  27420
agcaaaacta gaggagcaaa aaagaaatct caggtttggt ttttaggaat agccgaacgc  27480
gggggtcgaa cccgcagcct taagattaag agtcttacgc tctaccgatt gagctagccc  27540
ggccgggctg ttgaagagag ttgccatata gcgctacata atcctaaagc ggtcagggcc  27600
tgggggcga acacgctgac ataatgctag cgcgtcgagc ggcgaatcct ctggaaccaa  27660
aattgttagg tggaaggtgg cttcatctac gaatctgggt gtttcctcga ttggatctta  27720
tcattgcttc cctgattcgt atgagtcttt aattttctgg ttgcttgact ctgaccgcgg  27780
tcactagatt gcccaccatg tgcgttacta gaacctttcc ccgattcttt gctgcagcta  27840
acactataca gggcaaagct cgtggacgac catcagatcc atactgcctc gttgcataac  27900
ccgattcctt ggcaattgca tacatacgtc tggcctttcc tgatcatctg gcccgtgttc  27960
tttgcctttt acctctctcc cgagcgctat gatacctaca ttcagggaca ggagtggacc  28020
tttgtgtttg cggggtctat catcacagtc cagtcgctct tctggctgat gaccaagtgg  28080
aacatcgata ttaacaccct attcacaact actcgatcca aatccatcga cactgcccgg  28140
```

```
cttatcaaag tggttccgat caccaatgcc ggctctgccg agatctgtaa cctgattaga  28200
gagcacattg gcccgaagaa gaccctttcg ttcctcttcc agaagcgccg cttcctcttt  28260
taccccgaga ctcgctcctt cgcacccctt tcttacgccc tcgacgccga gccgaagccg  28320
gccctcaaga ctttccagca gagcgagggc ttcacgtcga aggccgagat tgagcgcgtc  28380
caaaaccact atggtgacaa taccttcgat attcccgttc ccggtttcat tgagctcttc  28440
caggagcatg ccgtcgcgcc gttcttcgtc ttccagatct tctgtgttgg attgtggatg  28500
ttggatgaat actggtacta ctcgctcttc accctcttca tgctcgtgat gtttgagagt  28560
accgttgtgt ggcagcgcca gaggacattg agcgagttcc gtgggatgag catcaagcct  28620
tacgatgtct gggtataccg tgaacggaaa tggcaggaga tcaccagtga taagcttctt  28680
cccggtgatc tcatgtcggt gaaccgcacc aaggaggaca gcggtgttgc ttgtgatatt  28740
cttctggttg aaggcagtgt cattgtcaac gaggctatgc tttctggcga gagcacccct  28800
cttctgaaag actctatcca gctccgtcct ggcgatgact tgattgagcc agatggattg  28860
gataagctct cgtttgtgca tggaggtacc aaagtcctcc aggttactca ccctaatctg  28920
actggcgacg cgggcttgaa gaacttggcc agcaacgtta ccatgcctcc agacaatggt  28980
gccttgggtg tggttgtgaa gaccggtttc gaaaccagcc agggtagcct cgtccgtact  29040
atgatctact cgactgaacg tgtctctgcc aacaatgttg aagctctgct gttcattctc  29100
ttccttttga ttttcgccat tgccgcttcg tggtacgtgt ggcaagaagg tgtgattcgg  29160
gatcgcaaac gctccaagct tctgctcgac tgcgtcctta ttatcaccag tgttgttcct  29220
cccgaattgc ctatggaact cagcttggcc gtcaacacta gtcttgctgc tctgagcaag  29280
tatgccattt tctgcactga gccattccgt atcccctttg ctggtcgtgt tgatatcgct  29340
tgcttcgata agactggtac cctgaccgga gaggatcttg tcgttgatgg tattgctgga  29400
ctcactttgg gtgaggctgg ttcaaaggtc gaagctgatg gtgctcacac cgagttggcc  29460
aattcttctg ctgctggacc cgacaccact ctcgttctcg ccagtgctca tgccttggtg  29520
aaattggatg agggtgaagt cgtcggtgac cccatggaga aggctacttt ggaatggctt  29580
ggctggactc tgggcaagaa cgacactttg tcttccaagg gcaacgctcc cgttgtttct  29640
ggtcgcagcg ttgagtctgt tcaaatcaag agaagattcc agttctcctc ggccctgaag  29700
cgtcagagca ctatcgcgac cattacgacc aatgaccgca atgcttccaa gaagaccaag  29760
tctactttg tgggtgtcaa gggtgccccc gagaccatca acactatgct ggtcaacaca  29820
cctcccaact acgaggagac ctacaagcac ttcacccgta acggtgctcg tgtgcttgct  29880
cttgcttaca agtacctttc ttcggagacc gagctttccc agagccgtgt gaacaattat  29940
gtccgcgaag agatcgaatc cgaactgatt tttgccggtt tccttgtcct gcagtgcccg  30000
ctgaaggacg atgccatcaa gtctgtccaa atgttaaatg aaagcagtca ccgtgttgtc  30060
atgatcaccg gtgataaccc attgactgct gtccacgtcg cacgcaaggt tgaaattgtt  30120
gaccgtgagg ttctcattct tgatgccccc gaacatgaca actctggaac caagattgtc  30180
tggcgtacca ttgacgataa gctcaacctt gaagtcgacc ccactaagcc tcttgatcct  30240
gaaatcttga agactaagga tatttgtatc actggatatg ccttggcaaa gttcaagggc  30300
cagaaggctc tccctgatct gctccgtcac acctgggttt acgctcgtgt ctctcccaag  30360
cagaaggaag agattctcct tggtcttaaa gatgctggat acaccactct gatgtgcggt  30420
gatggaacca acgatgttgg tgctctgaag caggcccacg tcggtgtcgc gcttctgaac  30480
```

```
ggctcgcaag aggatctcac caagatcgct gaacactacc ggaacactaa gatgaaggag  30540
ctgtacgaga agcaggtcag catgatgcaa agatttaacc agcccgcccc tccagtacct  30600
gttctgatcg ctcacctgta tccccccggc cctaccaacc cacactacga gaaagcgatg  30660
gagagagagt cgcagcgcaa gggtgctgcg atcaccgctc ccggcagcac tcccgaagct  30720
attccgacta tcacatcccc tggcgcacag gccctgcagc aatcgaactt gaacccccag  30780
cagcagaaaa agcagcaggc ccaggcagct gcagctggcc ttgcagacaa gctcacatcg  30840
tctatgatgg aacaggagct ggatgacagc gagcccccca ctatcaagct gggtgatgca  30900
tccgtcgctg ctcccttcac tagcaagttg gccaacgtta ttgctatccc gaatattatc  30960
cgtcaaggtc gttgcaccct ggtcgcgact attcagatgt ataaaatcct cgctttgaac  31020
tgcttgatca gtgcctacag tcttagtgtc atctacctgg atggtatcaa gtttggtgat  31080
ggacaggtca ctatcagcgg tatgctgatg agtgtctgct tcctttcaat ttcccgcgcc  31140
aaggtatgtc gtatttccca tgtcgaccaa atgatttgct aatatgttac tgtgtgaagt  31200
ctgtcgaggg tctgtccaag gaacgcccgc aacccaatat tttcaacgtc tacatcattg  31260
gatctgttct tggacagttt gccatccaca ttgcgactct gatctacctt tccaactatg  31320
tctataagca cgagccgtac gtgatgaaaa cttccccttt catttgtcct acttcatagc  31380
taacataatc aacaggagag attctgatat tgatctcgag ggcgagtttg agccttccct  31440
tctgaacagt gccatctacc tcctccagct gattcagcaa atctccacct tctcgattaa  31500
ctaccaaggc cgtcccttcc gtgagtcaat ccgcgagaac aagggcatgt actggggcct  31560
cattgccgcg tccggtgtcg cattctcctg cgccactgaa ttcattcccg agctgaatga  31620
gaagttgcgc ctcgtcccct tcaccaacga atttaaggtg acattgactg tgctgatgat  31680
cttcgactac ggtggctgtt ggttgattga gaacgtcctc aagcacctgt tcagtgactt  31740
ccgtcccaag gacattgcca ttcgtcgccc tgaccagctc aagcgggagg cggaacggaa  31800
gttgcaagag caagtcgacg ctgaggccca gaaggagctg caaaggaagg tctagaggtt  31860
ggtggtttga agatttgtat ctgtaaacat agagaggagg ttgttgaatt ttagaaatgt  31920
tcaagtggtg tgtgacattt aatacattta tttttggctt ttattgaagc attcttggaa  31980
actatatgta gaaacaaatt cgtatagttg aatggctcct actctgtact gtccaatcgt  32040
cgtgaggcca ggtattgcct tggtagagaa cagtgtagac tcaaatgtgg cgatcgtccg  32100
atcagcttgt tacgaggtta gggctcgaaa tgatcggccc accataactt cttgtagctc  32160
cttgtttgag aggatgcagt ctacccgtta tgtagaccta attatccagg atggtcgaga  32220
atacttctca atacacaggg ttagacccca gatatatgat atgtcacctc agagaggggc  32280
aaagactggg taattccaaa aaatgtgatt ttgcagaggg tcaaagctat atcggatact  32340
gcttcttttc tctgcctcat agtgaaggaa acactatatt cttcatggta ggcaaagagg  32400
taaaagtgta cgtgccccaa ttcggtagaa ggataggccc tgtttgaaaa ttccacattt  32460
tgaccgatat atctatagaa acatatgaag tagccgcttg gcccttctcc atttgaagct  32520
tcgagctgac gtggacttca aatgcaggat gctttgttcc tttgtactgc catgcaatat  32580
aatgttgcct tgaactcgag attataatgc gaaaacctcg tagagccgat cgcagcccga  32640
gccaacattt ttctataata cataggtaaa cgatctgtga attcagaaag ctcccacatt  32700
gtattataag catgaatcat tcaacgcgag acttcaagct tcatgaaatc cttcaggaac  32760
ccaacagttg aaagaccacc aattccctag atcccactga tttcgattac gacattccgg  32820
attgtagtag ggcatatggc gatgccgggt ttgattgcaa agaatatatt cccatacatt  32880
```

```
gcagtaccca cctttgacaa tccaggattc aggtgcgtcg acgccgccgt gattacaact  32940
agtgctggag gcgccgttgt catagaacca tttgcaggag ttaccgtcaa ttgattcggt  33000
gggtagactt cggtctggtc gcaggcattt gaggtccttc gtccagccca cattatgtcc  33060
tttcatttgg atgtagttgc ccttgcagtt cttcttggtg tacatttcca ctgtccatgg  33120
atggacatat ggcgcatcgc tggttgtggt gcttggtttc gtgttggatg ttttggttga  33180
cttgaccgat gtagttttgc tagtggtggt ggccttggtg gttgtggtgc ttgacgcagc  33240
actggccgat atcgttttat tggatgggga caaggcaagt ctctgaatag tcataaattt  33300
tgcaaaagca ttaaccgcat tagtaggcat ggcagtcttt tttgaggtgg tcgctccaat  33360
ggtgcggttg gtagaagtac agaattccga agtgcttcca caataaccat acgaagagca  33420
ctatgaattt attagatgtt gaagagcagg atttagagcc tcttgactca cacattcatt  33480
agctgcacat ggattcaaag aacccagatc agaccagttg ctagggcgct ttgtcccagg  33540
cacccggggg ccacaaacag cattggaaag cgtagctggc atcatgggtt ctccagaact  33600
gaggcatata acagcaccct gcactaaatg gtcacatcca agccattccc aggtttgagc  33660
attgtaggtc tcgatatcag ccaaggcgag agagtgttct tgagcaatcg tggtgcaggt  33720
ttcgcccgcc tggacaacat atttgtgaca aagaccatca ctacctgctt gaggtgcacc  33780
tgatattgct gtcggactgg ccaaaaggac gcctatgaga gtcacgaagt tgcttggtcg  33840
gaagcaccac atcatattga ctgatggaga gtagttgctt tgcttgtctt tattttgcaa  33900
ggcaggtttc atctttatct gttcaaagag gaaaacatgt gccaaactgc caaggataga  33960
tgcacgcatg aatatgacat tgccggggag gggcaaatgt ttgtgaaaga actaggatac  34020
tgtgccaggg ccattagcat agtattgaag caaattatag aatggcactg catcaaaatg  34080
tggaatcctc gaatttttttc tttgtcttct aacgcctagt gcatgtcttt ccaggttgtc  34140
cttgaaggct ttgtctggtc tcccagaaat ggaaggactc aagggtatgt atacagcttc  34200
taaaacgtaa atgattcacc cgagaaagga attcataatc cgaggaaggt cagacacata  34260
aggctgtctc gaaacccctt gaatgcccaa ggaagaaagg aaattcctac ggctgggtca  34320
gactagcaag aaaacgtcac ttgacttctg agatccactc agatagcaga agaacgtgtt  34380
tggtgatttt cgttctttgt aaatgcatag gaccagatga ttcgaggaat cttcttgtta  34440
gcacccttaa tccaaatctt ctgtagacca agcactcggc tattgatact gtttcgagag  34500
tctgtaagat atgacattac tctgatacag atacgtggaa tggaaacatt gcgggctttc  34560
gaatgacatt gggttgacta acgaaggccc cttcacgcag tgacgaggcc ccaaagttca  34620
aggccaacgc gcaaagcggg accaacatcg aactccccat tctcggggag ctgagggccc  34680
gccttgattt tgacatcttc ccatttgtca aagtcattat tgaacgcctg cgtcatttcc  34740
gaagcattca gaatgcgggc caaccggaag tgacaatcta ggagatcagc acttggcaga  34800
cttcgtacat tgtctgcgtc cttgttgctg aaaaccacct ctatcggaaa aaagaccttg  34860
taatttgaag aaattccttc gaacgtgtga actttgtatt tattgtccac atcctttgaa  34920
atttcggtta gcaaggtaat aaagtaaaat cattccacaa atgggagcgc actcactgtg  34980
ggttcaaagg caagacggaa cgcgccgaag tgttcatgta cccagctagt aagggtgaga  35040
ccgttggata agctgttgat ctcttggtgc ctgaaattca tttcccggat cctgggaaaa  35100
cagcgccaga ggacctccca agctcgtgac gcatttggta tgagatcgtt cttgagcccg  35160
tgagtcattg atcttaatga ggatccgaga acttactcgc cggggatccc agactgcata  35220
```

```
tgacaaggga attatgtgtg cgctttctgt attcccgagt tttcaatat cctctgattt  35280
gcctagactg tcccaccgat cgagatccat gtcaccagtg acaacacagc agtaaccgtc  35340
gcgttttagt aaaccttcct tgaactcccc tgtccgggac ataggctggt ccaaagtgga  35400
atttttcttc gcatgggaat cctgccgttc ggttgacgag atagttactg atgggggctt  35460
agaccgagaa cgcactattt cgagtgaacg tataagtcag ggctttgtac ttttttgtta  35520
acttactacg ggttcttaga ccagtgtaca ggttgcgaaa gtattgataa attccatcat  35580
cgtcttccag gctgatgata tccttcgcaa tggagctttt gccgcgatct gggaggaaat  35640
tcaaaaaagc ttgtaatgat ttttgcagga tgtcttcgcg ttctccacgg ctcttgggtt  35700
tgtaactttc tattcttaag cgtgcggttt caatatcctg cttttgttcg gtttccgatg  35760
cttcagtaga ttgtgaaaac agcgattgtg cgcgggggata ggcacgtgct ggaccagaaa  35820
cttcgctctc ttgggtttgc tgtttacgtt tttgagaccg ggtggtgggt cgatctgatt  35880
caggcaattc agaacggcgc cttttaagat tagttttgga tggtggcgac gaggaagttg  35940
gagggatgtt ttggttcggg gcatcggctt gtagtgaagg gggcggtcgc tttgctggtt  36000
tctttttctt ccccatgatg tctgctagta gtagtatatt tcttgctttc cttttccaat  36060
actgagatgg tagtttcagt ggatgaaaat gagaacaatg ggataattca gtggatggaa  36120
atgagaacaa tgtgatgatg ggggagaaaa gtgatgtggg ggtgtcgggg gatagctccg  36180
agatattcct ccggcagaat cgctccaccg aaaaacagtc cgccggacgg gtcatccccc  36240
ttttggagaa aatgtatttg tagttacaga aaggcattag cccacagaac aagaattcat  36300
ccatatttca ttgttttcca tcaagcaatt actcgtccaa tcgtctctcg gagggtgcag  36360
agaataggct ctctctggaa ggccgctgga aaaagtggga aaaggataca ttctgtggcc  36420
acaggcgtgg gacagggttt ccccctgaca ctgggggaga aatgtggaaa tgtgggggaa  36480
ctctgcggag acggaagaac aaaaggcggt caactgctgc ctccacgtga tgtcacgtgg  36540
agcttagccg tccagcttgg aagataaccc tagaggaata tgagcatatt ctacggagaa  36600
ctactccgta caacatacgg agtactcata caactctgta gcaacccctg atgtgatctg  36660
tatttgaagt gtggacctga taccgactgc tcctcaaacc ccttaaaccc gtatcgagta  36720
ctccgtaata tgtacaccgt tcactgactc acattgatta atcacattag atctctcgtt  36780
ttcatgtacg tggatcatta tgagttcgag cattgaatat aagctaaaac catacccccct  36840
gaccctaagg ggccttctgg aaagaaaaat cttgtctttt gcaaatcaaa atatatatag  36900
agttgtttac ccgaactgtc gggttatgca tcttcaggcc tgtggagctg tgtcatcatt  36960
ttgttactcc cccttatcta ccgcaggatc gccaaaatgc ctagcgagac tgctacaggt  37020
gactttggtc cagcgccgcc tgggatagac ttgacagaga accaaactgg cgacttgcta  37080
ggagcagtga ttcctgtagc ggtggtcgcg acgactgcgg tgatattgcg gacgattgcg  37140
ccgacgagga tcaaagagat ccgacaaaca gctattgatg actatctcat tgttgcggcg  37200
cttttattct cttggggaac ggcaatatca tgcttcatca gtgagttgac catgaggcca  37260
aagccgatgg gcccagtact cacaacagac tctttaggca ttccatatgg caacggttat  37320
catttgcaat ctgtgacaaa agcagagttt aacactgttt ggaaagtaag gaatccaata  37380
ttaaatgaga tgcctgggat agacgttgac cagacattca gatccttttc gcctatgtca  37440
tgatttacgc tacagccgtt acctgcacca aagcctcgat cgtcttattt tacggccgca  37500
tcttccactt tcgctggtca ctggccatct gcctgtttct ggtcgttgga tattgggttg  37560
ccattattgt cacggttggg atggcctgtc gaccactgcc acatttctgg ttggtctaca  37620
```

```
cagatccatc agcccttggt gtctgcattg atattcccac gttctttttc gcaaatggca  37680

ttgctgccat ggcgattgat gtgatcatac tgtgcatgcc gatgccagca atataccagt  37740

ctcagatgca gttgtcgcaa aaggtagcgg tcgtgggtat cctactcttg ggaagtttgt  37800

atgtacctct gcccgggccc tcctacgaga aggactgtag ctaattattc tcagtgtttg  37860

cgtggcaagt atctgccgga tcatcgcact tcagaatatc accgacggga cagatacgac  37920

gtgggctatc gccccagtct ttatttggtc gtccgtggaa ccatttgttg ggattatttg  37980

cgcatgcctc ccaacatttg ggcctttctt tcggcaatgg cggtccatcg ctcggacgcg  38040

ctcatcaact gatggcagta ccgatccaag ctctgagcta ccatctgaga caacgacctg  38100

gctccgaaga tcccgaacca aaaaacctgc caaggactca atattcagta tcaatgattt  38160

ttgctgtgtc gatgaggtcc aactaatgaa cgatatcaat gccactcggt cgctggggga  38220

cgaggctgcg agtgaccatc aggacgtgga gggaggctgt atcacagtcc aaaaagatgt  38280

ggaagtgaca tgggccaagt acaagtcagg aaaaaaaaat gatctggcct tcaagtatca  38340

taaaggggct tgatcagctt tgcaaatatt tcgacttgac acggactata tttgcgtttt  38400

gtgtatattt aataaaaata gacgccactg gcaatttgta attgataaag gtaagtctta  38460

ttccgtaatc catacccgt actctataca aagtactctg tgctccgtac ggagtacacg  38520

gaaacaaacg gggatatagt cgtggcacct ttcccgtgtt ggcggacttg cccgtaacgt  38580

aaacactccg cagatccctt ccaacacagt acataatcct gcagcgaaga gcgatctgat  38640

agacgctatg tgccgtcgtg acttgttatg ccaattaacg gtggcagaat tgtggagcaa  38700

tctagcagag gaaagtttcg atgtgcatgc cgagccctaa aaagtcccag tgcggagaat  38760

gtagtaatcg actggacatt ccatgtactt tgcacgctat aacatatttc tatgccatat  38820

acccctctgg taatcatgta gatcctcttg cttactgcgt tggctccttt gtatcgtact  38880

ttccgcgtcg cagcattata agaggataga gagaccgcat gagagaatac acaagagaaa  38940

tcactaattc actacctgat cccccaattc actcaacatg tctcacattc acacttccag  39000

attgcaaa                                                           39008
```

<210> SEQ ID NO 267
<211> LENGTH: 556
<212> TYPE: PRT
<213> ORGANISM: Penicillium coprobium PF1169

<400> SEQUENCE: 267

```
Met Glu His Glu Thr Asp Leu Val Ser Phe Ala Phe Ser Gly Pro Ala
1               5                   10                  15

Phe Asp Gln Ser Lys Pro Ile Tyr Ile Asp Ala Arg Asn Pro Ser Arg
            20                  25                  30

Ala Phe Asn Ala Ile Gln Phe Arg Arg Leu Val Arg Ser Leu Ile Ala
        35                  40                  45

Gly Leu Lys Ala Arg Gly Val Glu Arg Gly Asp Cys Val Leu Val Gln
    50                  55                  60

Leu Glu Asn Ser Val Leu His Ser Ala Leu Phe Phe Ala Ile Val Gly
65                  70                  75                  80

Ala Gly Gly Val Tyr Met Gly Phe Asp Val Ala Ser Arg Pro His Glu
                85                  90                  95

Val Ala His Leu Leu Arg Val Ala Glu Pro Arg Leu Ile Ile Thr Ala
            100                 105                 110

Pro Ser Ala Leu Thr Arg Val Leu Glu Val Cys Asn Asn Gln Gly Met
```

```
        115                 120                 125

Ser Ser Asn Gln Val Leu Leu Met Asp Glu Lys Ser Ile Glu Ser Val
    130                 135                 140

Val Gln Phe Ala His Gly Gln Ala Glu Gln Thr Glu Asp Leu Asp Thr
145                 150                 155                 160

Gln Thr Val Asp Gln Pro Ile Arg Leu Glu Ser Leu Leu Gln Tyr Gly
                165                 170                 175

Glu Leu Asp Trp Leu Arg Phe Glu Asp Ser Glu Glu Ser Lys Ile Thr
            180                 185                 190

Pro Ala Ala Met Phe Leu Thr Ser Gly Thr Ser Gly Leu Pro Lys Ala
        195                 200                 205

Ala Ile Arg Thr His His Thr Ile Ile Ser His His Leu Ser Val Tyr
    210                 215                 220

Tyr Glu Val Pro Tyr Pro Val Val Arg Leu Met Ala Leu Pro Leu Tyr
225                 230                 235                 240

His Ser Phe Gly Asp Phe Trp Gly Asn Ile Phe Pro Ile Arg Tyr Gly
                245                 250                 255

Gln Pro Leu Tyr Ile Ile Pro Arg Phe Glu Ile Thr Ala Leu Leu Asp
            260                 265                 270

Gly Ile Arg Gln His His Ile Thr Glu Thr Tyr Met Val Pro Ala Met
        275                 280                 285

Ile His Ile Leu Asn Arg Ser Ser Leu Asn Val Ala Glu Ser Leu Ser
    290                 295                 300

Ser Leu Arg Tyr Ile Gly Ile Ser Gly Ala Pro Ile Asp Gly Tyr Ser
305                 310                 315                 320

Met Gln Gln Phe Gln Ser Leu Leu Ser Pro Asp Ala Ile Ala Gly Asn
                325                 330                 335

Leu Trp Gly Met Ser Glu Val Gly Val Val Phe Gln Asn Arg Tyr Gly
            340                 345                 350

Ile Gln Pro Gln Phe Gly Ser Val Gly Thr Leu Leu Pro Arg Tyr Glu
        355                 360                 365

Leu Arg Phe Val Asn Pro Asp Thr Gly Glu Asp Val Ala Gly Thr Pro
    370                 375                 380

Asp Ser Pro Gly Glu Leu Tyr Val Arg Gly Pro Gly Leu Leu Leu Ala
385                 390                 395                 400

Tyr Lys Gly Arg Thr Asp Ala Lys Asp Glu Gln Gly Trp Phe Arg Thr
                405                 410                 415

Gly Asp Met Phe His Val Glu Asp Gly Asn Tyr His Val Ile Gly Arg
            420                 425                 430

Thr Lys Asp Leu Ile Lys Val Arg Gly Gln Val Thr Gln Tyr Ser Val
        435                 440                 445

Ala Pro Ala Glu Ile Glu Gly Ile Leu Arg Lys Asp Pro Ser Ile Lys
    450                 455                 460

Asp Ala Ala Val Ile Gly Val Met Leu Pro Asp Gly Ser Ser Glu Val
465                 470                 475                 480

Pro Arg Ala Tyr Val Val Arg Asn Asp Thr Ser Pro Glu Thr Thr Ala
                485                 490                 495

Asp Gln Val Ala Gly Leu Ile Gln Ser Gln Leu Ala Ser Tyr Lys Ala
            500                 505                 510

Leu Asp Gly Gly Val Val Phe Val Asp Asp Ile Pro Arg Ile Gly Ile
        515                 520                 525

Gly Lys His His Arg Ala Lys Leu Ser Gln Leu Asp His Gln Arg Glu
    530                 535                 540
```

Thr Ile Ala Ser Ile Leu Ala Glu Pro Val Ala Val
545 550 555

<210> SEQ ID NO 268
<211> LENGTH: 2447
<212> TYPE: PRT
<213> ORGANISM: Penicillium coprobium PF1169

<400> SEQUENCE: 268

Met Lys Ala Thr Glu Pro Val Ala Ile Ile Gly Thr Gly Cys Arg Phe
1 5 10 15

Pro Gly Gly Ala Ser Ser Pro Ser Lys Leu Trp Glu Leu Leu Gln Ser
20 25 30

Pro Arg Asp Ile Ala Arg Lys Val Pro Ala Asp Arg Phe Asn Ile Asp
35 40 45

Ala Phe Tyr His Pro Asp Gly Asp His His Gly Thr Thr Asn Val Lys
50 55 60

Glu Ser Tyr Phe Leu Asp Glu Asp Ile Lys Ala Phe Asp Ala Ala Phe
65 70 75 80

Phe Asn Ile Ser Pro Thr Glu Ala Val Ala Met Asp Pro Gln Gln Arg
85 90 95

Leu Leu Leu Glu Thr Val Tyr Glu Ser Leu Asp Ala Ala Gly Leu Arg
100 105 110

Met Asp Ala Leu Gln Arg Ser Lys Thr Gly Val Phe Cys Gly Thr Leu
115 120 125

Arg Asn Asp Tyr Asn Gln Ile Gln Ala Met Asp Pro Gln Ala Phe Pro
130 135 140

Ala Tyr Val Val Thr Gly Asn Ser Pro Ser Ile Met Ala Asn Arg Ile
145 150 155 160

Ser Tyr Tyr Phe Asp Trp Gln Gly Pro Ser Met Ala Val Asp Thr Gly
165 170 175

Cys Ser Ser Ser Leu Leu Ala Val His Leu Gly Val Glu Ala Leu Gln
180 185 190

Asn Asp Asp Cys Ser Met Ala Val Ala Val Gly Ser Asn Leu Ile Leu
195 200 205

Ser Pro Asn Ala Tyr Ile Ala Asp Ser Lys Thr Arg Met Leu Ser Pro
210 215 220

Thr Gly Arg Ser Arg Met Trp Asp Ser Lys Ala Asp Gly Tyr Gly Arg
225 230 235 240

Gly Glu Gly Val Ala Ser Val Val Leu Lys Arg Leu Gln Asp Ala Ile
245 250 255

Asn Asp Gly Asp Pro Ile Glu Cys Val Ile Arg Ala Ser Gly Ala Asn
260 265 270

Ser Asp Gly Arg Thr Met Gly Ile Thr Met Pro Asn Pro Lys Ala Gln
275 280 285

Gln Ser Leu Ile Leu Ala Thr Tyr Ala Arg Ala Gly Leu Ser Pro Gln
290 295 300

Asn Asn Pro Glu Asp Arg Cys Gln Tyr Phe Glu Ala His Gly Thr Gly
305 310 315 320

Thr Gln Ala Gly Asp Pro Gln Glu Ala Ala Ala Ile Asn Ser Ser Phe
325 330 335

Phe Gly Pro Glu Ser Val Pro Asp Ser Thr Asp Arg Leu Tyr Val Gly
340 345 350

Ser Ile Lys Thr Ile Ile Gly His Thr Glu Ala Thr Ala Gly Leu Ala

```
        355                 360                 365

Gly Leu Ile Lys Ala Ser Leu Ser Leu Gln His Gly Met Ile Ala Pro
    370                 375                 380

Asn Leu Leu Met Gln His Leu Asn Pro Lys Ile Lys Pro Phe Ala Ala
385                 390                 395                 400

Lys Leu Ser Val Pro Thr Glu Cys Ile Pro Trp Pro Ala Val Pro Asp
                405                 410                 415

Gly Cys Pro Arg Arg Ala Ser Val Asn Ser Phe Gly Phe Gly Gly Ala
            420                 425                 430

Asn Val His Val Val Leu Glu Ser Tyr Thr Arg Ser Glu Leu Ser Pro
        435                 440                 445

Ser Asn Asn Ile Pro Ser Ser Leu Pro Phe Val Phe Ser Ala Ala Ser
    450                 455                 460

Glu Arg Thr Leu Thr Cys Val Met Glu Ser Tyr Ala Thr Phe Leu Gln
465                 470                 475                 480

Glu His Ala Thr Val Ser Leu Val Gly Leu Ala Leu Ser Leu Trp Asp
                485                 490                 495

Arg Arg Ser Thr His Arg His Arg Leu Thr Leu Met Ala His Ser Ile
            500                 505                 510

Gln Glu Leu Lys Asp Gln Ile Asn Thr Glu Ile Ser Arg Arg Val Thr
        515                 520                 525

Gly Lys Pro Ala Ser Val Val Ser Arg Ser Asn Thr Arg Pro Arg Arg
    530                 535                 540

Val Met Gly Ile Phe Thr Gly Gln Gly Val Gln Trp Pro Gln Met Gly
545                 550                 555                 560

Leu Asp Leu Ile Glu Ala Ser Pro Ser Ile Arg Lys Trp Ile Met Asn
                565                 570                 575

Leu Glu Glu Ala Leu Asp Glu Leu Pro Leu Asp Leu Arg Pro Gln Phe
            580                 585                 590

Ser Leu Leu Asp Glu Leu Ser Gln Pro Ala Ser Ser Ser Arg Val Asn
        595                 600                 605

Glu Gly Leu Leu Ser Leu Pro Leu Arg Thr Ala Leu Gln Ile Met Gln
    610                 615                 620

Val Asn Met Leu Arg Ala Val Gly Ile Glu Leu Thr Ile Val Val Gly
625                 630                 635                 640

His Ser Ser Gly Glu Ile Val Ala Ala Tyr Ala Ala Gly Val Leu Thr
                645                 650                 655

Ala Ser Asp Ala Ile Arg Ile Ala Tyr Leu Arg Gly Met Thr Ile Asp
            660                 665                 670

Lys Ser Arg Asp Pro Thr Gly Arg Met Met Ala Val Asn Leu Thr Trp
        675                 680                 685

Gln Gln Ala Gln Asn Ile Cys Ala Leu Glu Ala Tyr Ser Gly Arg Ile
    690                 695                 700

Ser Val Ala Ala Ala Asn Ser Pro Ser Ser Val Thr Leu Ser Gly Asp
705                 710                 715                 720

Ala Glu Cys Leu Arg Glu Leu Glu Trp Leu Leu Lys Ser Leu Gly Leu
                725                 730                 735

Thr Pro Arg Met Leu Arg Val Asp Thr Ala Tyr His Ser Pro His Met
            740                 745                 750

Lys Pro Cys Ala Asp Pro Tyr Arg Asp Ala Met Lys Ala Tyr Pro Val
        755                 760                 765

Ala Leu Ser Ala Ser Ala Ser Arg Trp Tyr Ser Ser Val Tyr Pro Gly
    770                 775                 780
```

```
Glu Val Met Thr Gly Tyr Asp Gln Gln Glu Leu Thr Gly Glu Tyr Trp
785                 790                 795                 800

Val Glu Asn Met Leu Arg Pro Val Gln Phe Ser Gln Ala Leu Glu Ala
                805                 810                 815

Ala Ala Arg Asp Ala Gly Pro Pro Asp Leu Ile Ile Glu Ile Gly Pro
            820                 825                 830

His Pro Thr Leu Arg Gly Pro Val Leu Gln Thr Leu Ser Lys Met His
        835                 840                 845

Ser Ala His Ser Ala Ile Pro Tyr Leu Ala Leu Ala Glu Arg Gly Lys
    850                 855                 860

Pro Gly Leu Asp Thr Trp Ala Thr Ala Leu Gly Ser Ser Trp Ala His
865                 870                 875                 880

Leu Gly Pro Asn Val Val Arg Leu Thr Asp Tyr Val Ser Leu Phe Asp
                885                 890                 895

Pro Asn His Trp Pro Val Leu Val Glu Ser Leu Pro Phe Tyr Pro Phe
            900                 905                 910

Asp His Thr Gln Thr Tyr Trp Thr Gln Ser Arg Met Ser Ser Asn His
        915                 920                 925

Asn His Arg Ala Thr Ser Pro Asn Ala Leu Leu Gly Ser Leu Ser Pro
    930                 935                 940

Glu Thr Gly Ala Glu Lys Phe Arg Trp Arg Asn Tyr Leu Arg Pro Glu
945                 950                 955                 960

Glu Leu Pro Trp Leu Ala Asp Arg Arg Ala Asp Ser Gly Ser Val Phe
                965                 970                 975

Pro Glu Thr Gly Tyr Ile Ser Met Ala Leu Glu Ala Gly Met Ile Met
            980                 985                 990

Ala Gln Thr Gln Gly Leu Arg Leu  Leu Asn Val Lys Asp  Leu Thr Ile
        995                 1000                1005

His Thr  Gln Leu Pro Ile Gln  Asn Asp Pro Ile Gly  Thr Glu Val
    1010                1015                1020

Leu Val  Thr Val Gly Ser Ile  His Ser His Asp Gly  Ala Ile Thr
    1025                1030                1035

Ala Trp  Phe Cys Cys Glu Ala  Val Val Ser Gly Glu  Leu Val Gln
    1040                1045                1050

Cys Ala  Thr Ala Lys Met Ile  Met His Pro Gly Asp  Ser Asp Arg
    1055                1060                1065

Ala Leu  Leu Pro Pro Gln Gly  Gln Leu Pro Gln Ala  Leu Glu Pro
    1070                1075                1080

Val Asp  Ser Thr Glu Phe Tyr  Asp Ser Leu Arg Arg  Ala Asp Tyr
    1085                1090                1095

His Cys  Thr Gly Pro Phe Ser  Thr Leu Thr Gly Leu  Arg Lys Arg
    1100                1105                1110

Arg Asp  Leu Ala Thr Gly Ser  Val Pro Val Pro Ser  Asn Asp Ser
    1115                1120                1125

Asp Glu  Pro Met Ala Leu His  Pro Ala Ile Leu Asp  Leu Gly Val
    1130                1135                1140

Gln Thr  Met Ile Ala Ala Ile  Gly Gly Leu Glu Glu  Thr Leu Leu
    1145                1150                1155

Thr Gly  Pro Phe Leu Ser Arg  Asn Val Asp Ser Thr  Trp Ile Asn
    1160                1165                1170

Pro Val  Leu Cys Ala Ser Asp  Trp Gln Gly Lys Glu  Leu Thr Val
    1175                1180                1185
```

```
Ala Ser  Tyr Leu Thr Cys Val  Asn Gly Asp Arg Ile  Arg Gly Asp
    1190                 1195                 1200

Ile Asp  Ile Phe Thr Met Asn  Gly Glu Lys Ala Val  Gln Leu Glu
    1205                 1210                 1215

Gly Val  Ser Leu Ile Cys Gln  Pro Ser Gly Thr Ala  Pro Asn Asn
    1220                 1225                 1230

Leu Gln  Val Leu Ser Gln Thr  Ala Trp Gly Pro Leu  Glu Pro Thr
    1235                 1240                 1245

Leu Lys  Lys Gly Ser Arg Lys  Leu Pro Ala Thr Met  Leu Gln Leu
    1250                 1255                 1260

His Ser  Leu Arg Glu Glu Leu  Ala Leu Leu Tyr Leu  Lys Gln Ala
    1265                 1270                 1275

Arg Asn  Gly Leu Thr Asp Leu  Glu Arg Ser Gly Leu  Asp Phe Asp
    1280                 1285                 1290

Gly Ala  Arg Leu Leu Ala Trp  Met Asn Gln Cys Ile  Ala Asn Ala
    1295                 1300                 1305

Ser Gln  Glu Pro Asp Pro Val  Gly Glu Ser Glu Cys  Leu Asp Gln
    1310                 1315                 1320

Lys Ile  Glu Asp Phe Thr Ala  Gly Val Ser Pro Ser  Leu Leu Asn
    1325                 1330                 1335

Asp Pro  Gly Leu Thr Ala Ile  Ala Ala Val Gly Gln  Arg Leu Pro
    1340                 1345                 1350

Arg Val  Leu Arg Asp Ser Gly  Leu Gln Ile Glu Ala  Trp Pro Ala
    1355                 1360                 1365

Ile Asp  Glu Glu Ser Gln Tyr  Leu Lys Glu Asp Leu  Gln Val Leu
    1370                 1375                 1380

Asp Leu  Glu Asp Glu Leu Val  Ser Val Val Ser Gln  Ala Cys Phe
    1385                 1390                 1395

Arg Phe  Pro Gln Met Asn Ile  Leu Gln Ile Gly Gln  Phe Gly Gly
    1400                 1405                 1410

His Val  His Ser Gly Leu Lys  Lys Met Gly Arg Thr  Tyr Arg Ser
    1415                 1420                 1425

Phe Thr  Tyr Ala Gly Leu Ser  Val Ser Gly Leu Gln  Ala Ile Glu
    1430                 1435                 1440

Glu Asp  Leu Glu Gln Pro Gly  Glu Val Ser His Lys  Thr Leu Asp
    1445                 1450                 1455

Ile Asn  Glu Asp Pro Val Glu  Gln Gly Cys Arg Glu  Gln Phe Tyr
    1460                 1465                 1470

Asp Met  Val Leu Ile Thr Ala  Ala Val Phe Leu Gln  Glu Val Ala
    1475                 1480                 1485

Val Ala  His Val Arg Arg Leu  Leu Lys Pro Gly Gly  Phe Leu Val
    1490                 1495                 1500

Leu Leu  Val Arg Thr Asn Pro  Ser Thr Thr Tyr Leu  Asn Leu Leu
    1505                 1510                 1515

Phe Gly  Pro Pro Met Arg Cys  Thr Glu Thr Gly Lys  Gly Tyr Cys
    1520                 1525                 1530

Ser Gly  Glu Pro Ile Thr Thr  Arg Arg Asp Trp Val  Glu Leu Leu
    1535                 1540                 1545

Ser Asn  Gly Gly Phe Tyr Gly  Leu Asp Ser Phe Asp  Ala Ser Gln
    1550                 1555                 1560

Glu Ser  Glu Ser Leu Gly Asp  Phe Ser Leu Leu Leu  Cys Arg Thr
    1565                 1570                 1575

Pro Asp  Ser Pro Ala Glu Pro  Gln Ser Arg Gly Asp  Leu Leu Leu
```

```
    1580                1585                1590

Leu Gly  Gly Asp Ala Glu Glu  Ala Asp Cys Leu Thr  Ser Glu Leu
    1595                1600                1605

Phe Glu  Leu Val Gln Asp Asp  Phe Val Lys Val Ala  His Ala Pro
    1610                1615                1620

Asp Leu  Asp Leu Ile Glu Asp  Arg Asp Leu Ser Lys  Leu Thr Val
    1625                1630                1635

Leu Tyr  Leu Val Asp Asp Arg  Asp Leu Thr Asn Ala  Thr Leu Ser
    1640                1645                1650

Glu Leu  Cys Arg Leu Met Thr  Val Ser Lys Arg Met  Leu Val Val
    1655                1660                1665

Thr Cys  Glu Lys Val Asp His  Pro Asp Ala Gly Leu  Val Lys Gly
    1670                1675                1680

Leu Leu  Ser Thr Phe Leu Ala  Ser Glu Arg Ser Ser  Ser Leu Leu
    1685                1690                1695

Gln Leu  Leu His Ile Thr Asp  Pro Val Gly Val Thr  Thr Glu Ile
    1700                1705                1710

Leu Ala  Thr Ala Leu Gly His  Phe Val Gln Ala Ser  Ala Ala Gln
    1715                1720                1725

Glu Asn  Pro His Ser Cys Gly  Leu Thr Asn Ile Glu  Pro Glu Ile
    1730                1735                1740

Gln Tyr  Asp Gly Ser Met Phe  Arg Val Pro Arg Gln  Tyr His Asp
    1745                1750                1755

His Ala  Thr Gly Leu Arg His  Leu Ala Arg Arg Gln  Lys Val Thr
    1760                1765                1770

Asp Cys  Val Asp Leu Asp Lys  Gly Val Val Gln Ile  Leu Pro Ala
    1775                1780                1785

Thr Thr  Asp Lys Thr Cys Glu  Gly Phe Arg Leu Leu  Ser Met Ala
    1790                1795                1800

Asp Pro  Pro Ile Thr Ala Ser  Tyr Gly Pro Thr Leu  His Leu Arg
    1805                1810                1815

Val Arg  His Ser Ser Ile Ala  Ala Val Arg Val Ala  Gly Ala Ile
    1820                1825                1830

Phe Leu  Arg Leu Val Ile Gly  Leu Asp Val Lys Ser  Asn Lys Arg
    1835                1840                1845

Met Ile  Ala Leu Ser Ser His  Ile Ala Ser His Val  Ile Val Pro
    1850                1855                1860

Asp Ser  Trp Ala Trp Ser Val  Pro Asp Thr Val Leu  Glu Ala His
    1865                1870                1875

Glu Gln  Ser Tyr Leu Arg Ala  Thr Ala Ala Ala Leu  Leu Ala Gly
    1880                1885                1890

Tyr Leu  Val Glu Gln Val Pro  Gln Ser Gly Thr Leu  Val Val His
    1895                1900                1905

Glu Ala  Asp Gly Val Leu Gln  Ser Val Phe His Gln  Met Leu Thr
    1910                1915                1920

Arg Arg  Asp Gly Lys Val Ile  Phe Ser Thr Ser Lys  Ser Asn Pro
    1925                1930                1935

Asp Lys  Glu Arg Pro Met Leu  Leu Leu His Glu His  Ser Thr Ala
    1940                1945                1950

Arg Gln  Leu Ser Gln Val Leu  Pro Ser Asp Val Ser  Ala Ile Ala
    1955                1960                1965

Ile Leu  His Arg Arg Gly Gln  Gly Val Tyr Asp Arg  Met Leu Ser
    1970                1975                1980
```

```
Leu Leu  Pro Asp Asn Ala Thr  Arg Ile His Leu Gln  Asp Phe Tyr
    1985                 1990                 1995

Leu Thr  Ser Ala Ser Thr Gly  Pro Ile Asn Ala Asp  Asp Ser Ser
    2000                 2005                 2010

Leu Ile  Ala Lys Ala Phe Leu  Thr Ala Cys Leu Val  Ala Tyr Thr
    2015                 2020                 2025

Gly Arg  Glu Gly Leu Pro Pro  Asn Ser Val Asp Ser  Leu Pro Ile
    2030                 2035                 2040

Ser Arg  Ile Ser Glu Tyr Pro  Ile Leu Asp Ser Gln  Asp Ala Val
    2045                 2050                 2055

Val Asp  Trp Asp Ser Thr Thr  Pro Val Leu Ala Gln  Ile Pro Thr
    2060                 2065                 2070

Ala Gly  Ser Gln Val Gln Leu  Ser Glu Lys Lys Thr  Tyr Ile Leu
    2075                 2080                 2085

Val Gly  Leu Gly Ser Glu Leu  Ala His Ala Ile Cys  Leu Trp Leu
    2090                 2095                 2100

Ala Thr  His Gly Ala Lys Trp  Ile Leu Leu Ala Gly  Ser Arg Leu
    2105                 2110                 2115

Asp Ser  Asp Ala Trp Trp Leu  Glu Glu Val Ser Arg  Arg Gly Thr
    2120                 2125                 2130

Arg Ile  Ala Val Ser Lys Ile  Asn Leu Ile Asp Gly  Ile Ser Ala
    2135                 2140                 2145

Thr Ser  Leu His Gln Thr Ile  Pro Tyr Ala Phe Pro  Pro Val Val
    2150                 2155                 2160

Gly Gly  Val Leu Ile Gln Pro  Pro Pro Leu Pro Asp  Cys Ser Leu
    2165                 2170                 2175

Ser Gln  Leu Thr Ile Asp Ser  Leu Arg Asn His Leu  His Pro Val
    2180                 2185                 2190

Leu Lys  Gly Leu Gln Gln Leu  Asp Glu Leu Tyr Lys  Thr Pro Thr
    2195                 2200                 2205

Leu Asp  Phe Trp Val Leu Ile  Gly Ser Ile Ala Gly  Val Leu Gly
    2210                 2215                 2220

His Ala  Asp Gln Ala Met Thr  Ala Ala Met Ser Glu  Lys Met Ala
    2225                 2230                 2235

Leu Leu  Val Arg His Arg Arg  Ala Gln Gly Arg Pro  Ala Ser Leu
    2240                 2245                 2250

Val His  Leu Gly Glu Ile His  Gly Ile Ser Ser Pro  Ser Pro Ser
    2255                 2260                 2265

Gln Pro  Leu Trp Cys Gly Pro  Val Ala Val Ser Gln  Arg Asp Val
    2270                 2275                 2280

Asp Glu  Ile Leu Ala Glu Ala  Ile Leu Cys Gly Arg  Ser Asp Ser
    2285                 2290                 2295

Asn Ser  Asn Ala Glu Leu Ile  Gly Gly Leu Arg His  Gln Ser Leu
    2300                 2305                 2310

Lys Cys  Gly Tyr Gly Glu Cys  Pro Ile Pro Lys Leu  Trp Pro Phe
    2315                 2320                 2325

Tyr Ser  Tyr Thr Ala Thr Ala  Ser Gln Asp Gln Ile  Leu Ala Leu
    2330                 2335                 2340

Ile Glu  Thr Arg Ser Thr Lys  Asp Leu Val Thr Ala  Ala Thr Ser
    2345                 2350                 2355

Leu Glu  Glu Lys Ala Glu Ala  Val Val Arg Pro Leu  Met Glu Lys
    2360                 2365                 2370
```

```
Ile Arg  Ala Ser Leu Asn Leu  Ala Glu Asp Ala Pro  Leu Ser Ala
    2375                2380                2385

Asp Thr  Leu Ile Pro Glu Leu  Gly Ile Asp Ser Leu  Ile Ala Ile
    2390                2395                2400

Gly Leu  Ser Gln Trp Phe Thr  Lys Glu Leu Ser Val  Asp Ile Gly
    2405                2410                2415

Val Ile  Leu Ile Leu Ser Gly  Val Ser Val Gly Glu  Leu Ala His
    2420                2425                2430

Ala Ala  Ala Ser Lys Leu Cys  Asn Val Ser Val Gly  Lys Pro
    2435                2440                2445


<210> SEQ ID NO 269
<211> LENGTH: 509
<212> TYPE: PRT
<213> ORGANISM: Penicillium coprobium PF1169

<400> SEQUENCE: 269

Met Asp Asn Met Asp Asn Met Asn Asn Thr Pro Leu Gly Phe Asn Trp
1               5                   10                  15

Ala Trp Ala Val Ile Ile Ser Phe Leu Gly Leu Leu Thr Phe Ser Phe
            20                  25                  30

Val Ser Pro His Leu Phe Pro Ser Arg Leu Thr Val Ile Asn Gly Gly
        35                  40                  45

Arg Ala Trp Asp Ile Phe Arg Thr Lys Ala Lys Lys Arg Phe Arg Ser
    50                  55                  60

Asp Ala Ala Arg Leu Ile Lys Asn Gly Phe Glu Glu Ser Pro Asp Ala
65                  70                  75                  80

Phe Arg Ile Ile Thr Asp Asn Gly Pro Leu Leu Val Leu Ser Pro Gln
                85                  90                  95

Tyr Ala Arg Glu Val Arg Ser Asp Asp Arg Leu Ser Leu Asp His Phe
            100                 105                 110

Ile Ala Ser Glu Phe His Pro Asn Ile Pro Gly Phe Glu Pro Phe Lys
        115                 120                 125

Leu Ile Leu Asp Pro Lys Asn Pro Leu Asn Thr Ile Leu Lys Ser Asn
    130                 135                 140

Leu Thr Gln Ala Leu Glu Asp Leu Ser Ala Glu Val Thr Glu Ala Leu
145                 150                 155                 160

Ser Ala Thr Cys Thr Asp Asp Pro Glu Trp His Glu Val Ser Val Ser
                165                 170                 175

Gln Thr Ala Leu Lys Ile Ile Ala Gln Met Ala Ser Lys Ala Phe Ile
            180                 185                 190

Gly Gln Glu Arg Cys Arg Asp Ala Lys Trp His Asn Ile Ile Ile Thr
        195                 200                 205

Tyr Thr His Asn Val Tyr Gly Ala Ala Gln Ala Leu His Phe Trp Pro
    210                 215                 220

Ser Phe Leu Arg Pro Ile Val Ala Gln Phe Leu Pro Ala Cys Arg Thr
225                 230                 235                 240

Leu Gln Ala Gln Ile Ala Glu Ala Arg Glu Ile Leu Glu Pro Leu Val
                245                 250                 255

Ala Gln Arg Arg Ala Glu Arg Ala Thr Arg Ala Ala Gln Glu Lys Pro
            260                 265                 270

His Pro Ser Gly Gly Asp Ile Ile Asp Trp Leu Glu Gln Phe Tyr Gly
        275                 280                 285

Asp Gln Pro Tyr Asp Pro Val Ala Ala Gln Leu Leu Leu Ser Phe Ala
    290                 295                 300
```

```
Ala Ile His Gly Thr Ser Asn Leu Leu Ala Gln Ala Leu Ile Asp Leu
305                 310                 315                 320

Cys Gly Gln Pro Glu Leu Val Gln Asp Leu Arg Glu Glu Ala Val Ser
                325                 330                 335

Val Leu Gly Lys Glu Gly Trp Thr Arg Ala Ala Leu Tyr Gln Leu Lys
            340                 345                 350

Leu Met Asp Ser Ala Leu Lys Glu Ser Gln Arg Leu Ala Pro Asn Arg
        355                 360                 365

Leu Leu Ser Met Gly Arg Ile Ala Gln Gly Asp Met Asp Leu Ser Asp
    370                 375                 380

Gly Leu Arg Ile His Arg Gly Thr Thr Leu Met Val Ser Ala His Asn
385                 390                 395                 400

Met Trp Asp Pro Glu Ile Tyr Pro Asp Pro Arg Lys Tyr Asp Gly Tyr
                405                 410                 415

Arg Phe His Lys Leu Arg Gln Thr Ser Gly Gln Glu Gly Gln His Gln
            420                 425                 430

Leu Val Ser Ser Thr Pro Asp His Met Gly Phe Gly Tyr Gly Lys His
        435                 440                 445

Ala Cys Pro Gly Arg Phe Phe Ala Ala Ala Gln Ile Lys Val Ala Leu
    450                 455                 460

Cys Asn Ile Leu Leu Lys Tyr Asp Ile Glu Tyr Arg Gly Gly Lys Ser
465                 470                 475                 480

Pro Gly Val Trp Gly Gln Gly Ile His Leu Phe Pro Asp Pro Thr Ser
                485                 490                 495

Arg Ile His Val Arg Arg Arg Lys Glu Glu Ile Asn Leu
            500                 505


<210> SEQ ID NO 270
<211> LENGTH: 505
<212> TYPE: PRT
<213> ORGANISM: Penicillium coprobium PF1169

<400> SEQUENCE: 270

Met Ile Glu Leu Lys Asp Ala Ser Met Gly Ala Val Leu Leu Thr Cys
1               5                   10                  15

Val Leu Val Leu Ala Gly Leu Tyr Leu Ile Arg Leu Thr Leu Ser Ser
            20                  25                  30

Asp Gln Leu Asp Lys Phe Pro Ser Ile Asn Pro Arg Lys Pro Trp Glu
        35                  40                  45

Ile Val Asn Val Phe Ala Gln Arg Arg Phe Gln Gln Asp Gly Pro Arg
    50                  55                  60

Tyr Leu Glu Ala Gly Tyr Ala Lys Ser Pro Ile Phe Ser Val Val Thr
65                  70                  75                  80

Asp Leu Gly Pro Lys Leu Val Val Ser Gly Ala Phe Ile Glu Glu Phe
                85                  90                  95

Lys Asp Glu Lys Leu Leu Asp His Tyr Arg Ser Met Ile Glu Asp Phe
            100                 105                 110

Met Ala Glu Val Pro Gly Phe Glu Ser Met Phe Leu Gly Asn Leu His
        115                 120                 125

Asn Thr Val Leu Arg Asp Val Ile Ser Val Ile Thr Arg Glu Leu Glu
    130                 135                 140

Gln Leu Leu Ala Pro Leu Ser Asp Glu Val Ser Ala Ala Leu Val Asp
145                 150                 155                 160

Thr Trp Thr Asp Ser Pro Asp Trp His Glu Val Ala Leu Leu Pro Ser
```

```
                165                 170                 175

Met Leu Gly Leu Ile Ala Lys Val Ser Ser Leu Val Phe Val Gly Glu
            180                 185                 190

Pro Leu Cys Arg His Pro Val Trp Leu Glu Thr Val Ile Asn Phe Thr
        195                 200                 205

Leu Ile Arg His Asn Ala Ile Leu Ala Leu His Gln Cys Pro Ala Val
    210                 215                 220

Leu Arg Pro Val Leu His Trp Val Leu Pro Pro Cys Gln Lys Leu Arg
225                 230                 235                 240

Arg Glu Ile Arg Thr Ala Arg Thr Leu Ile Asp Ser Ala Leu Glu Lys
                245                 250                 255

Ser Arg Lys Asn Pro Gln Thr Glu Lys Phe Ser Ser Val Ala Trp Val
            260                 265                 270

Asp Ala Phe Ala Lys Gly Asn Lys Tyr Asn Ala Ala Met Val Gln Leu
        275                 280                 285

Arg Leu Ala Asn Ala Ser Ile His Ser Ser Ala Asp Leu Leu Val Lys
    290                 295                 300

Ile Leu Ile Asn Leu Cys Glu Gln Pro Glu Leu Ile Arg Asp Leu Arg
305                 310                 315                 320

Asp Glu Ile Ile Ser Val Leu Gly Glu Asn Gly Trp Arg Ser Ser Thr
                325                 330                 335

Leu Asn Gln Leu Lys Leu Leu Asp Ser Val Leu Lys Glu Ser Gln Arg
            340                 345                 350

Leu His Pro Val Thr Thr Gly Ala Phe Ser Arg Phe Thr Arg Gln Asp
        355                 360                 365

Ile Lys Leu Thr Asn Gly Thr Glu Ile Pro Ser Gly Thr Pro Ile Met
    370                 375                 380

Val Thr Asn Asp Val Ala Gly Asp Ala Ser Ile Tyr Asp Asp Pro Asp
385                 390                 395                 400

Val Phe Asp Gly Tyr Arg Tyr Phe Arg Met Arg Glu Gly Ala Asp Lys
                405                 410                 415

Ala Arg Ala Pro Phe Thr Thr Thr Gly Gln Asn His Leu Gly Phe Gly
            420                 425                 430

Tyr Gly Lys Tyr Ala Cys Pro Gly Arg Phe Phe Ala Ala Thr Glu Ile
        435                 440                 445

Lys Ile Ala Leu Cys His Met Leu Leu Lys Tyr Glu Trp Arg Leu Val
    450                 455                 460

Lys Asp Arg Pro His Gly Ile Val Thr Ser Gly Phe Ala Ala Phe Arg
465                 470                 475                 480

Asp Pro Arg Ala Ser Ile Glu Val Arg Arg Arg Ala Val Ala Gly Glu
                485                 490                 495

Glu Leu Glu Val Leu Thr Gly Lys Lys
            500                 505


<210> SEQ ID NO 271
<211> LENGTH: 241
<212> TYPE: PRT
<213> ORGANISM: Penicillium coprobium PF1169

<400> SEQUENCE: 271

Met Asp Gly Trp Ser Asp Ile Ser Ser Ala Pro Ala Gly Tyr Lys Asp
1               5                   10                  15

Val Val Trp Ile Ala Asp Arg Ala Leu Leu Ala Gln Gly Leu Gly Trp
            20                  25                  30
```

```
Ser Ile Asn Tyr Leu Ala Met Ile Tyr Gln Ser Arg Lys Asp Arg Thr
        35                  40                  45

Tyr Gly Met Ala Ile Leu Pro Leu Cys Cys Asn Phe Ala Trp Glu Phe
    50                  55                  60

Val Tyr Thr Val Ile Tyr Pro Ser Gln Asn Pro Phe Glu Arg Ala Val
65                  70                  75                  80

Leu Thr Thr Trp Met Val Leu Asn Leu Tyr Leu Met Tyr Thr Thr Ile
                85                  90                  95

Lys Phe Ala Pro Asn Glu Trp Gln His Ala Pro Leu Val Gln Arg Ile
            100                 105                 110

Leu Pro Val Ile Phe Pro Val Ala Ile Ala Ala Phe Thr Ala Gly His
        115                 120                 125

Leu Ala Leu Ala Ala Thr Val Gly Val Ala Lys Ala Val Asn Trp Ser
    130                 135                 140

Ala Phe Leu Cys Phe Glu Leu Leu Thr Ala Gly Ala Val Cys Gln Leu
145                 150                 155                 160

Met Ser Arg Gly Ser Ser Arg Gly Ala Ser Tyr Thr Ile Trp Val Ser
                165                 170                 175

Arg Phe Leu Gly Ser Tyr Ile Gly Ser Ile Phe Met His Val Arg Glu
            180                 185                 190

Thr His Trp Pro Gln Glu Phe Asp Trp Ile Ser Tyr Pro Phe Val Ala
        195                 200                 205

Trp His Gly Ile Met Cys Phe Ser Leu Asp Ile Ser Tyr Val Gly Leu
    210                 215                 220

Leu Trp Tyr Ile Arg Arg Gln Glu Arg Gln Gly Gln Leu Lys Lys Ala
225                 230                 235                 240

Met


<210> SEQ ID NO 272
<211> LENGTH: 464
<212> TYPE: PRT
<213> ORGANISM: Penicillium coprobium PF1169

<400> SEQUENCE: 272

Met Lys Val Ile Ile Val Gly Gly Ser Ile Ala Gly Leu Ala Leu Ala
1               5                   10                  15

His Cys Leu Asp Lys Ala Asn Ile Asp Tyr Val Ile Leu Glu Lys Lys
            20                  25                  30

Lys Glu Ile Ala Pro Gln Glu Gly Ala Ser Ile Gly Ile Met Pro Asn
        35                  40                  45

Gly Gly Arg Ile Leu Glu Gln Leu Gly Leu Tyr Asp Gln Ile Glu Glu
    50                  55                  60

Leu Ile Glu Pro Leu Val Arg Ala His Val Thr Tyr Pro Asp Gly Phe
65                  70                  75                  80

Asn Tyr Thr Ser Arg Tyr Pro Ala Leu Ile Gln Gln Arg Phe Gly Tyr
                85                  90                  95

Pro Leu Ala Phe Leu Asp Arg Gln Lys Leu Leu Gln Ile Leu Ala Thr
            100                 105                 110

Gln Pro Val Gln Ser Ser Arg Val Lys Leu Asp His Lys Val Glu Ser
        115                 120                 125

Ile Glu Val Ser Pro Cys Gly Val Thr Val Ile Thr Ser Asn Gly His
    130                 135                 140

Thr Tyr Gln Gly Asp Leu Val Val Gly Ala Asp Gly Val His Ser Arg
145                 150                 155                 160
```

```
Val Arg Ala Glu Met Trp Arg Leu Ala Asp Ala Ser Gln Gly Asn Val
                165                 170                 175

Cys Gly Asn Gly Asp Lys Ala Phe Thr Ile Asn Tyr Ala Cys Ile Phe
            180                 185                 190

Gly Ile Ser Ser His Val Asp Gln Leu Asp Pro Gly Glu Gln Ile Thr
        195                 200                 205

Cys Tyr Asn Asp Gly Trp Ser Ile Leu Ser Val Ile Gly Gln Asn Gly
    210                 215                 220

Arg Ile Tyr Trp Phe Leu Phe Ile Lys Leu Glu Lys Glu Phe Val Tyr
225                 230                 235                 240

Asp Gly Ser His Lys Thr Gln Leu His Phe Ser Arg Glu Asp Ala Arg
                245                 250                 255

Ala His Cys Glu Arg Leu Ala Gln Glu Pro Leu Trp Lys Asp Val Thr
            260                 265                 270

Phe Gly Gln Val Trp Ala Arg Cys Glu Val Phe Gln Met Thr Pro Leu
        275                 280                 285

Glu Glu Gly Val Leu Gly Lys Trp His Trp Arg Asn Ile Ile Cys Ile
    290                 295                 300

Gly Asp Ser Met His Lys Phe Ala Pro His Ile Gly Gln Gly Ala Asn
305                 310                 315                 320

Cys Ala Ile Glu Asp Ala Ala Gln Leu Ser Asn Ser Leu His Thr Trp
                325                 330                 335

Leu Ser Gly Ser Gly Lys Glu His Gln Leu Lys Thr Asp Asp Leu Thr
            340                 345                 350

Glu Ile Leu Ala Gln Phe Ala Gln Thr Arg Leu Gln Arg Leu Gly Pro
        355                 360                 365

Thr Ala Met Ala Ala Arg Ser Ala Met Arg Leu His Ala Arg Glu Gly
    370                 375                 380

Leu Lys Asn Trp Ile Leu Gly Arg Tyr Phe Leu Pro Tyr Ala Gly Asp
385                 390                 395                 400

Lys Pro Ala Asp Trp Ala Ser Arg Gly Ile Ala Gly Gly Asn Thr Leu
                405                 410                 415

Asp Phe Val Glu Pro Pro Thr Arg Ala Gly Pro Gly Trp Ile Gln Phe
            420                 425                 430

Ser Gln Ser Gly Lys Arg Thr Ser Phe Pro Met Ala Val Ala Gly Leu
        435                 440                 445

Cys Leu Val Ser Ile Val Ala Arg Ile Met Tyr Leu Lys Leu Val Ala
    450                 455                 460


<210> SEQ ID NO 273
<211> LENGTH: 317
<212> TYPE: PRT
<213> ORGANISM: Penicillium coprobium PF1169

<400> SEQUENCE: 273

Met Ala Gly Ser Gln Ser Thr Ala Gln Leu Ala Arg Leu Leu Ile Asp
1               5                   10                  15

Ile Ser Arg Phe Asp Lys Tyr Asn Cys Leu Phe Ala Ile Phe Pro Gly
            20                  25                  30

Val Trp Ser Ile Phe Leu Ala Ala Ala Ser Arg His Ala Asp Gly Asp
        35                  40                  45

Pro Val Pro Leu Asp Phe Val Leu Gly Arg Ala Gly Leu Ala Phe Met
    50                  55                  60

Tyr Thr Tyr Met Leu Ser Gly Ala Gly Met Val Trp Asn Asp Trp Ile
65                  70                  75                  80
```

```
Asp Arg Asp Ile Asp Ala Gln Val Ala Arg Thr Lys Asn Arg Pro Leu
                85                  90                  95

Ala Ser Gly Arg Leu Ser Thr Arg Ala Ala Leu Ile Trp Met Leu Val
            100                 105                 110

Gln Tyr Ala Ala Ser Val Trp Leu Met Asp Arg Met Val Ser Gly Gln
        115                 120                 125

Asp Val Trp Thr Tyr Met Leu Pro Leu Thr Thr Gly Ile Ile Leu Tyr
    130                 135                 140

Pro Phe Gly Lys Arg Pro Thr Ser Arg Lys Leu Gly Val Tyr Pro Gln
145                 150                 155                 160

Tyr Ile Leu Gly Ala Ser Ser Ala Leu Thr Ile Leu Pro Ala Trp Ala
                165                 170                 175

Ser Val Tyr Thr Gly Arg Ile Ser Leu Lys Asp Leu Gly Met Arg Cys
            180                 185                 190

Leu Pro Leu Cys Leu Phe Leu Phe Leu Trp Thr Ile Tyr Phe Asn Thr
        195                 200                 205

Ala Tyr Ser Tyr Gln Asp Ile Lys Asp Asp Cys Lys Leu Asn Val Asn
    210                 215                 220

Ser Ser Tyr Val Leu Ala Gly Ser His Val Arg Gly Met Leu Leu Leu
225                 230                 235                 240

Gln Ala Ile Ala Val Val Leu Val Ile Pro Trp Ile Leu Tyr Thr Ser
                245                 250                 255

Ala Ser Thr Trp Leu Trp Val Ser Trp Leu Gly Val Trp Thr Ala Ser
            260                 265                 270

Leu Gly Glu Gln Leu Tyr Leu Phe Asp Val Lys Asp Pro Ser Ser Gly
        275                 280                 285

Gly Lys Val His Arg Arg Asn Phe Ala Leu Gly Ile Trp Asn Val Leu
    290                 295                 300

Ala Cys Phe Val Glu Leu Leu Tyr Ala Ser Gly Ser Leu
305                 310                 315


<210> SEQ ID NO 274
<211> LENGTH: 522
<212> TYPE: PRT
<213> ORGANISM: Penicillium coprobium PF1169

<400> SEQUENCE: 274

Met Ser Thr Gln Glu Val Cys Leu Pro Val Ser Gln Arg Asp Gln Val
1               5                   10                  15

Lys Glu Gly Pro Val Arg Leu His Gly Leu Cys Glu Asp Gly Met Cys
            20                  25                  30

Asp Ala Arg Arg Thr Gly Asp Arg Ser Ala Tyr Pro Leu Ser Ser Leu
        35                  40                  45

Asp His Asn Pro Leu Gly Met Asn Val Thr Phe Leu Leu Phe Phe Gln
    50                  55                  60

Thr Thr Gln Pro Glu Lys Ser Ile Gly Val Leu Glu Asn Gly Ile Glu
65                  70                  75                  80

Leu Leu Leu Lys Val His Pro Phe Leu Ala Gly Asp Val Thr Arg Arg
                85                  90                  95

Thr Glu Ser Ser Gln Thr Lys Tyr Thr Trp Gln Ile Glu Pro Glu Ala
            100                 105                 110

Ser Glu Ser Leu Val Gln Phe Pro Ile Leu Arg Ile Arg His Tyr Gln
        115                 120                 125

Ala Glu Ser Phe Lys Glu Ile Gln Ser Lys Cys Leu Leu Thr Gly Thr
```

```
    130                 135                 140

Glu Glu Gln Glu Ile Ile Ser Arg Leu Ala Pro Leu Pro Ile Asp Met
145                 150                 155                 160

Asp Ile Ser Leu Pro Arg Arg Pro Ile Leu Arg Phe Gln Ala Asn Val
                165                 170                 175

Met Arg Asp Gly Ile Ile Leu Ala Met Thr Phe His His Ser Ala Met
            180                 185                 190

Asp Gly Ala Gly Ala Ala Arg Val Leu Gly Leu Leu Ala Asp Cys Cys
        195                 200                 205

Arg Asp Pro Thr Ala Met Ser Ser Ala Ser Val Ser Pro Asp Arg Gln
    210                 215                 220

Leu Arg Ser Glu Ile Glu Arg Leu Val Pro Glu Ser Ser Ser Gly Leu
225                 230                 235                 240

Ser Arg Met Asp Phe Ser Lys His Tyr Cys Gly Leu Gly Asp Trp Ala
                245                 250                 255

Ala Leu Leu Ala Lys Asn Trp Ser Gly Phe Val Arg Ala Arg Ala Thr
            260                 265                 270

Glu Leu Val Thr Trp Arg Leu Lys Ile Pro Gly Pro Lys Ile Glu Tyr
        275                 280                 285

Leu Lys Glu Ala Cys Asn Thr Leu Ile Lys Gly Gln Thr Ser Phe Gln
    290                 295                 300

Ala Asp Gly Arg Pro Ser Pro Gly Phe Leu Ser Ser Asn Asp Ile Val
305                 310                 315                 320

Ser Ala Leu Leu Ala Met Ile Leu Arg Gln Ala Gly Gln Leu Ala Gly
                325                 330                 335

Lys Ser Thr Glu Leu Ser Ile Ala Val Asp Met Arg Gly Asn Phe Lys
            340                 345                 350

Thr Pro Ala Phe Asp Asp Tyr Leu Gly Asn Met Val Leu Leu Thr Tyr
        355                 360                 365

Thr Pro Ile Gln Ala Gly Arg Asn Glu Ala Leu Val Asp Gly Thr Asp
    370                 375                 380

Pro Ser Val Glu Leu Arg Gln Glu Cys Leu Glu Asp Leu Thr Gln Ile
385                 390                 395                 400

Ala Ala Arg Ile Arg Gln Ser Leu Leu Ala Val Asp Ala Glu Tyr Ile
                405                 410                 415

Gln Asp Ala Leu Ser His Leu His Ser Gln Pro Asp Trp Ala Asp Ile
            420                 425                 430

Gly Phe Arg Gly Val Pro Ile Pro Leu Ser Ser Phe Arg Asn Phe Glu
        435                 440                 445

Ile Phe Gly Leu Asp Phe Gly Glu Ser Leu Gly Ala Gln Pro Arg Gly
    450                 455                 460

Phe Gln Leu His Leu Pro Val Leu Gly Gly Met Cys Phe Ile Leu Pro
465                 470                 475                 480

Lys Gly Gln Asp Asp Val Ala Ser Thr Glu Pro Trp Asp Leu His Leu
                485                 490                 495

Thr Leu Asn Arg Asp Asp Gln Leu Leu Leu Ala Lys Asp Pro Leu Phe
            500                 505                 510

Cys Trp Ala Ile Gly Ala Gln Ala Lys Glu
        515                 520
```

```
<210> SEQ ID NO 275
<211> LENGTH: 434
<212> TYPE: PRT
<213> ORGANISM: Penicillium coprobium PF1169
```

<400> SEQUENCE: 275

```
Met Asp Ser Leu Leu Thr Ser Pro Leu Trp Leu Lys Ile Ala His Glu
1               5                   10                  15

Leu Ala Leu Tyr Leu Ser Phe Ile Val Pro Thr Ala Phe Leu Ile Ile
            20                  25                  30

Thr Thr Gln Lys Ser Ser Ile Ile Arg Trp Ala Trp Thr Pro Cys Leu
        35                  40                  45

Leu Tyr Ile Leu Tyr Gln Phe Ser Leu Arg Val Pro Ser Leu Ser Thr
    50                  55                  60

Ser Gln Phe Leu Lys Gly Val Ala Ala Gly Gln Ala Thr Val Ala Ala
65                  70                  75                  80

Leu Gln Cys Leu Asn Leu Leu Leu Ile Thr Lys Leu Asp Gln Thr Asp
                85                  90                  95

Leu Leu Arg Ala Asn Leu Tyr Ser Pro Ser Ala Gly Leu Leu Ser Arg
            100                 105                 110

Leu Ala Gln Ser Cys Ala Leu Leu Val Asn Phe Arg Gly Ile Gly Thr
        115                 120                 125

Ile Trp Glu Val Arg Asn Ile Pro Gln His Ala Ala Phe Val Gln Pro
    130                 135                 140

Lys Gly Lys Asp Gln Ser Met Ser Arg Lys Arg Phe Val Leu Arg Glu
145                 150                 155                 160

Ile Ala Ile Ile Val Trp Gln Tyr Leu Leu Leu Asp Phe Ile Tyr Glu
                165                 170                 175

Ser Thr Lys Gly Thr Ser Ala Glu Asp Leu Met Arg Leu Phe Gly Pro
            180                 185                 190

Gly Met Glu Ile Lys Tyr Leu Asp Ala Thr Phe Glu Gln Trp Met Gly
        195                 200                 205

Arg Leu Ser Val Gly Ile Phe Ser Trp Leu Val Pro Ser Arg Val Cys
    210                 215                 220

Leu Asn Ile Thr Ser Arg Leu Tyr Phe Leu Ile Leu Val Val Leu Gly
225                 230                 235                 240

Ile Ser Ser Pro Glu Ser Cys Arg Pro Gly Phe Gly Arg Val Arg Asp
                245                 250                 255

Val Cys Thr Ile Arg Gly Val Trp Gly Lys Phe Trp His Gln Ser Phe
            260                 265                 270

Arg Trp Pro Leu Thr Ser Val Gly Asn Tyr Ile Ala Arg Asp Val Leu
        275                 280                 285

Gly Leu Ala His Pro Ser Leu Leu Glu Arg Tyr Thr Asn Ile Phe Phe
    290                 295                 300

Thr Phe Phe Thr Ser Gly Val Leu His Leu Val Cys Asp Ala Ile Leu
305                 310                 315                 320

Gly Val Pro Pro Ser Ala Ser Gly Ala Met Gln Phe Phe Cys Ser Phe
                325                 330                 335

Pro Leu Ala Ile Met Ile Glu Asp Gly Val Gln Glu Ile Trp Arg Arg
            340                 345                 350

Ala Thr Gly Gln Thr Lys Asp Ser Asp Arg Ala Val Pro Phe Trp Gln
        355                 360                 365

Arg Leu Val Gly Tyr Leu Trp Val Ala Val Trp Met Cys Val Thr Ser
    370                 375                 380

Pro Phe Tyr Leu Tyr Pro Ala Ala Arg Gln His Ala Glu Lys Asn Trp
385                 390                 395                 400

Ile Val Pro Phe Ser Ile Val Glu Glu Ile Gly Leu Gly Thr Ala Gln
```

```
                405                 410                 415

Lys Ile Leu Leu Gly Tyr Gly Leu Phe Val Tyr Trp Ala Val Gly Gly
            420                 425                 430

Glu Ile


<210> SEQ ID NO 276
<211> LENGTH: 1299
<212> TYPE: PRT
<213> ORGANISM: Penicillium coprobium PF1169

<400> SEQUENCE: 276

Met Leu Tyr Arg Ala Lys Leu Val Asp Asp His Gln Ile His Thr Ala
1               5                   10                  15

Ser Leu His Asn Pro Ile Pro Trp Gln Leu His Thr Tyr Val Trp Pro
            20                  25                  30

Phe Leu Ile Ile Trp Pro Val Phe Phe Ala Phe Tyr Leu Ser Pro Glu
        35                  40                  45

Arg Tyr Asp Thr Tyr Ile Gln Gly Gln Glu Trp Thr Phe Val Phe Ala
    50                  55                  60

Gly Ser Ile Ile Thr Val Gln Ser Leu Phe Trp Leu Met Thr Lys Trp
65                  70                  75                  80

Asn Ile Asp Ile Asn Thr Leu Phe Thr Thr Thr Arg Ser Lys Ser Ile
                85                  90                  95

Asp Thr Ala Arg Leu Ile Lys Val Val Pro Ile Thr Asn Ala Gly Ser
            100                 105                 110

Ala Glu Ile Cys Asn Leu Ile Arg Glu His Ile Gly Pro Lys Lys Thr
        115                 120                 125

Leu Ser Phe Leu Phe Gln Lys Arg Arg Phe Leu Phe Tyr Pro Glu Thr
    130                 135                 140

Arg Ser Phe Ala Pro Leu Ser Tyr Ala Leu Asp Ala Glu Pro Lys Pro
145                 150                 155                 160

Ala Leu Lys Thr Phe Gln Gln Ser Glu Gly Phe Thr Ser Lys Ala Glu
                165                 170                 175

Ile Glu Arg Val Gln Asn His Tyr Gly Asp Asn Thr Phe Asp Ile Pro
            180                 185                 190

Val Pro Gly Phe Ile Glu Leu Phe Gln Glu His Ala Val Ala Pro Phe
        195                 200                 205

Phe Val Phe Gln Ile Phe Cys Val Gly Leu Trp Met Leu Asp Glu Tyr
    210                 215                 220

Trp Tyr Tyr Ser Leu Phe Thr Leu Phe Met Leu Val Met Phe Glu Ser
225                 230                 235                 240

Thr Val Val Trp Gln Arg Gln Arg Thr Leu Ser Glu Phe Arg Gly Met
                245                 250                 255

Ser Ile Lys Pro Tyr Asp Val Trp Val Tyr Arg Glu Arg Lys Trp Gln
            260                 265                 270

Glu Ile Thr Ser Asp Lys Leu Leu Pro Gly Asp Leu Met Ser Val Asn
        275                 280                 285

Arg Thr Lys Glu Asp Ser Gly Val Ala Cys Asp Ile Leu Leu Val Glu
    290                 295                 300

Gly Ser Val Ile Val Asn Glu Ala Met Leu Ser Gly Glu Ser Thr Pro
305                 310                 315                 320

Leu Leu Lys Asp Ser Ile Gln Leu Arg Pro Gly Asp Asp Leu Ile Glu
                325                 330                 335

Pro Asp Gly Leu Asp Lys Leu Ser Phe Val His Gly Gly Thr Lys Val
```

```
            340                 345                 350

Leu Gln Val Thr His Pro Asn Leu Thr Gly Asp Ala Gly Leu Lys Asn
        355                 360                 365

Leu Ala Ser Asn Val Thr Met Pro Pro Asp Asn Gly Ala Leu Gly Val
    370                 375                 380

Val Val Lys Thr Gly Phe Glu Thr Ser Gln Gly Ser Leu Val Arg Thr
385                 390                 395                 400

Met Ile Tyr Ser Thr Glu Arg Val Ser Ala Asn Asn Val Glu Ala Leu
                405                 410                 415

Leu Phe Ile Leu Phe Leu Leu Ile Phe Ala Ile Ala Ala Ser Trp Tyr
            420                 425                 430

Val Trp Gln Glu Gly Val Ile Arg Asp Arg Lys Arg Ser Lys Leu Leu
        435                 440                 445

Leu Asp Cys Val Leu Ile Ile Thr Ser Val Val Pro Pro Glu Leu Pro
    450                 455                 460

Met Glu Leu Ser Leu Ala Val Asn Thr Ser Leu Ala Ala Leu Ser Lys
465                 470                 475                 480

Tyr Ala Ile Phe Cys Thr Glu Pro Phe Arg Ile Pro Phe Ala Gly Arg
                485                 490                 495

Val Asp Ile Ala Cys Phe Asp Lys Thr Gly Thr Leu Thr Gly Glu Asp
            500                 505                 510

Leu Val Val Asp Gly Ile Ala Gly Leu Thr Leu Gly Glu Ala Gly Ser
        515                 520                 525

Lys Val Glu Ala Asp Gly Ala His Thr Glu Leu Ala Asn Ser Ser Ala
    530                 535                 540

Ala Gly Pro Asp Thr Thr Leu Val Leu Ala Ser Ala His Ala Leu Val
545                 550                 555                 560

Lys Leu Asp Glu Gly Glu Val Val Gly Asp Pro Met Glu Lys Ala Thr
                565                 570                 575

Leu Glu Trp Leu Gly Trp Thr Leu Gly Lys Asn Asp Thr Leu Ser Ser
            580                 585                 590

Lys Gly Asn Ala Pro Val Val Ser Gly Arg Ser Val Glu Ser Val Gln
        595                 600                 605

Ile Lys Arg Arg Phe Gln Phe Ser Ser Ala Leu Lys Arg Gln Ser Thr
    610                 615                 620

Ile Ala Thr Ile Thr Thr Asn Asp Arg Asn Ala Ser Lys Lys Thr Lys
625                 630                 635                 640

Ser Thr Phe Val Gly Val Lys Gly Ala Pro Glu Thr Ile Asn Thr Met
                645                 650                 655

Leu Val Asn Thr Pro Pro Asn Tyr Glu Glu Thr Tyr Lys His Phe Thr
            660                 665                 670

Arg Asn Gly Ala Arg Val Leu Ala Leu Ala Tyr Lys Tyr Leu Ser Ser
        675                 680                 685

Glu Thr Glu Leu Ser Gln Ser Arg Val Asn Asn Tyr Val Arg Glu Glu
    690                 695                 700

Ile Glu Ser Glu Leu Ile Phe Ala Gly Phe Leu Val Leu Gln Cys Pro
705                 710                 715                 720

Leu Lys Asp Asp Ala Ile Lys Ser Val Gln Met Leu Asn Glu Ser Ser
                725                 730                 735

His Arg Val Val Met Ile Thr Gly Asp Asn Pro Leu Thr Ala Val His
            740                 745                 750

Val Ala Arg Lys Val Glu Ile Val Asp Arg Glu Val Leu Ile Leu Asp
        755                 760                 765
```

```
Ala Pro Glu His Asp Asn Ser Gly Thr Lys Ile Val Trp Arg Thr Ile
    770                 775                 780

Asp Asp Lys Leu Asn Leu Glu Val Asp Pro Thr Lys Pro Leu Asp Pro
785                 790                 795                 800

Glu Ile Leu Lys Thr Lys Asp Ile Cys Ile Thr Gly Tyr Ala Leu Ala
                805                 810                 815

Lys Phe Lys Gly Gln Lys Ala Leu Pro Asp Leu Leu Arg His Thr Trp
            820                 825                 830

Val Tyr Ala Arg Val Ser Pro Lys Gln Lys Glu Glu Ile Leu Leu Gly
        835                 840                 845

Leu Lys Asp Ala Gly Tyr Thr Thr Leu Met Cys Gly Asp Gly Thr Asn
    850                 855                 860

Asp Val Gly Ala Leu Lys Gln Ala His Val Gly Val Ala Leu Leu Asn
865                 870                 875                 880

Gly Ser Gln Glu Asp Leu Thr Lys Ile Ala Glu His Tyr Arg Asn Thr
                885                 890                 895

Lys Met Lys Glu Leu Tyr Glu Lys Gln Val Ser Met Met Gln Arg Phe
            900                 905                 910

Asn Gln Pro Ala Pro Pro Val Pro Val Leu Ile Ala His Leu Tyr Pro
        915                 920                 925

Pro Gly Pro Thr Asn Pro His Tyr Glu Lys Ala Met Glu Arg Glu Ser
    930                 935                 940

Gln Arg Lys Gly Ala Ala Ile Thr Ala Pro Gly Ser Thr Pro Glu Ala
945                 950                 955                 960

Ile Pro Thr Ile Thr Ser Pro Gly Ala Gln Ala Leu Gln Gln Ser Asn
                965                 970                 975

Leu Asn Pro Gln Gln Gln Lys Lys Gln Gln Ala Gln Ala Ala Ala Ala
            980                 985                 990

Gly Leu Ala Asp Lys Leu Thr Ser  Ser Met Met Glu Gln  Glu Leu Asp
        995                 1000                 1005

Asp Ser  Glu Pro Pro Thr Ile  Lys Leu Gly Asp Ala  Ser Val Ala
    1010                 1015                 1020

Ala Pro  Phe Thr Ser Lys Leu  Ala Asn Val Ile Ala  Ile Pro Asn
    1025                 1030                 1035

Ile Ile  Arg Gln Gly Arg Cys  Thr Leu Val Ala Thr  Ile Gln Met
    1040                 1045                 1050

Tyr Lys  Ile Leu Ala Leu Asn  Cys Leu Ile Ser Ala  Tyr Ser Leu
    1055                 1060                 1065

Ser Val  Ile Tyr Leu Asp Gly  Ile Lys Phe Gly Asp  Gly Gln Val
    1070                 1075                 1080

Thr Ile  Ser Gly Met Leu Met  Ser Val Cys Phe Leu  Ser Ile Ser
    1085                 1090                 1095

Arg Ala  Lys Ser Val Glu Gly  Leu Ser Lys Glu Arg  Pro Gln Pro
    1100                 1105                 1110

Asn Ile  Phe Asn Val Tyr Ile  Ile Gly Ser Val Leu  Gly Gln Phe
    1115                 1120                 1125

Ala Ile  His Ile Ala Thr Leu  Ile Tyr Leu Ser Asn  Tyr Val Tyr
    1130                 1135                 1140

Lys His  Glu Pro Arg Asp Ser  Asp Ile Asp Leu Glu  Gly Glu Phe
    1145                 1150                 1155

Glu Pro  Ser Leu Leu Asn Ser  Ala Ile Tyr Leu Leu  Gln Leu Ile
    1160                 1165                 1170
```

```
Gln Gln  Ile Ser Thr Phe Ser  Ile Asn Tyr Gln Gly  Arg Pro Phe
    1175                 1180                 1185

Arg Glu  Ser Ile Arg Glu Asn  Lys Gly Met Tyr Trp  Gly Leu Ile
    1190                 1195                 1200

Ala Ala  Ser Gly Val Ala Phe  Ser Cys Ala Thr Glu  Phe Ile Pro
    1205                 1210                 1215

Glu Leu  Asn Glu Lys Leu Arg  Leu Val Pro Phe Thr  Asn Glu Phe
    1220                 1225                 1230

Lys Val  Thr Leu Thr Val Leu  Met Ile Phe Asp Tyr  Gly Gly Cys
    1235                 1240                 1245

Trp Leu  Ile Glu Asn Val Leu  Lys His Leu Phe Ser  Asp Phe Arg
    1250                 1255                 1260

Pro Lys  Asp Ile Ala Ile Arg  Arg Pro Asp Gln Leu  Lys Arg Glu
    1265                 1270                 1275

Ala Glu  Arg Lys Leu Gln Glu  Gln Val Asp Ala Glu  Ala Gln Lys
    1280                 1285                 1290

Glu Leu  Gln Arg Lys Val
    1295
```

<210> SEQ ID NO 277
<211> LENGTH: 27
<212> TYPE: DNA
<213> ORGANISM: Artificial Sequence
<220> FEATURE:
<223> OTHER INFORMATION: Synthetic construct; a primer sequence for PCR

<400> SEQUENCE: 277
gcgcggtacc attgagacaa catggat 27

<210> SEQ ID NO 278
<211> LENGTH: 26
<212> TYPE: DNA
<213> ORGANISM: Artificial Sequence
<220> FEATURE:
<223> OTHER INFORMATION: Synthetic construct; a primer sequence for PCR

<400> SEQUENCE: 278
atttaaatag ttagacaata gtatca 26

<210> SEQ ID NO 279
<211> LENGTH: 35
<212> TYPE: DNA
<213> ORGANISM: Artificial Sequence
<220> FEATURE:
<223> OTHER INFORMATION: Synthetic construct; a primer sequence for PCR

<400> SEQUENCE: 279
gcgcggggta ccatgttgtc ttagcatttt catta 35

<210> SEQ ID NO 280
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 280
accacgctaa agatgggga ctttgcatac ccagcttcca 40

<210> SEQ ID NO 281
<211> LENGTH: 40
<212> TYPE: DNA

<213> ORGANISM: Artificial Sequence
<220> FEATURE:
<223> OTHER INFORMATION: Synthetic construct; a primer sequence for PCR

<400> SEQUENCE: 281
tggaagctgg gtatgcaaag tcccccatct ttagcgtggt 40

<210> SEQ ID NO 282
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 282
ggtacctctg ccatgaagtc ctcgatcatt gaccgataat 40

<210> SEQ ID NO 283
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 283
attatcggtc aatgatcgag gacttcatgg cagaggtacc 40

<210> SEQ ID NO 284
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 284
gagaggtgct agcagttgtt ctagttcgcg agtgatgaca 40

<210> SEQ ID NO 285
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 285
tgtcatcact cgcgaactag aacaactgct agcacctctc 40

<210> SEQ ID NO 286
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 286
cagtgctacc tcatgccagt ctggtgagtc cgtccaagta 40

<210> SEQ ID NO 287
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 287
tacttggacg gactcaccag actggcatga ggtagcactg 40

```
<210> SEQ ID NO 288
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 288

agtaaagcgc gaaaatgctc cggttgtgac tggatgcaac                           40


<210> SEQ ID NO 289
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 289

gttgcatcca gtcacaaccg gagcattttc gcgctttact                           40


<210> SEQ ID NO 290
<211> LENGTH: 20
<212> TYPE: DNA
<213> ORGANISM: Artificial Sequence
<220> FEATURE:
<223> OTHER INFORMATION: Synthetic construct; a primer sequence for PCR

<400> SEQUENCE: 290

attttcccta gatcacttct                                                 20


<210> SEQ ID NO 291
<211> LENGTH: 40
<212> TYPE: DNA
<213> ORGANISM: Artificial Sequence
<220> FEATURE:
<223> OTHER INFORMATION: Synthetic construct; a primer sequence for PCR

<400> SEQUENCE: 291

ccgaattcga gctcggtacc ttgtcttagc attttcatta                           40


<210> SEQ ID NO 292
<211> LENGTH: 38
<212> TYPE: DNA
<213> ORGANISM: Artificial Sequence
<220> FEATURE:
<223> OTHER INFORMATION: Synthetic construct; a primer sequence for PCR

<400> SEQUENCE: 292

ctactacaga tccccgggtc gtaattttcc ctagatca                             38
```